US012655420B2

(12) United States Patent
Watts

(10) Patent No.: US 12,655,420 B2
(45) Date of Patent: *Jun. 16, 2026

(54) OLIGONUCLEOTIDE DIRECTED AND RECORDED COMBINITORIAL SYNTHESIS OF ENCODED PROBE MOLECULES

(71) Applicant: Insitro, Inc., South San Francisco, CA (US)

(72) Inventor: Richard Edward Watts, San Carlos, CA (US)

(73) Assignee: Insitro, Inc., South San Franisco, CA (US)

( * ) Notice: Subject to any disclaimer, the term of this patent is extended or adjusted under 35 U.S.C. 154(b) by 1185 days.

This patent is subject to a terminal disclaimer.

(21) Appl. No.: 17/511,467

(22) Filed: Oct. 26, 2021

(65) Prior Publication Data

US 2022/0154179 A1     May 19, 2022

Related U.S. Application Data

(63) Continuation of application No. 16/306,356, filed as application No. PCT/US2017/036582 on Jun. 8, 2017, now Pat. No. 11,186,836.

(60) Provisional application No. 62/351,046, filed on Jun. 16, 2016.

(51) Int. Cl.

| | |
|---|---|
| *C12N 15/10* | (2006.01) |
| *C12Q 1/68* | (2018.01) |
| *C12Q 1/6811* | (2018.01) |
| *C12Q 1/6813* | (2018.01) |
| *C40B 10/00* | (2006.01) |
| *C40B 30/04* | (2006.01) |

(52) U.S. Cl.
CPC ........... *C12N 15/1093* (2013.01); *C12Q 1/68* (2013.01); *C12Q 1/6811* (2013.01); *C12Q 1/6813* (2013.01); *C40B 10/00* (2013.01); *C12Q 2525/161* (2013.01); *C12Q 2525/301* (2013.01); *C12Q 2565/514* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 5,573,905 | A | 11/1996 | Lerner et al. |
| 5,723,598 | A | 3/1998 | Lerner et al. |
| 5,759,779 | A | 6/1998 | Dehlinger |
| 6,060,596 | A | 5/2000 | Lemer et al. |
| 6,440,723 | B1 | 8/2002 | Dale |
| 7,070,928 | B2 | 7/2006 | Liu et al. |
| 7,223,545 | B2 | 5/2007 | Liu et al. |
| 7,413,854 | B2 | 8/2008 | Pedersen et al. |
| 7,442,160 | B2 | 10/2008 | Liu et al. |
| 7,479,472 | B1 | 1/2009 | Harbury et al. |
| 7,491,494 | B2 | 2/2009 | Liu et al. |
| 7,557,068 | B2 | 7/2009 | Liu et al. |
| 7,622,279 | B2 | 11/2009 | Ju |
| 7,704,925 | B2 | 4/2010 | Gouliaev et al. |
| 7,727,713 | B2 | 6/2010 | Pedersen et al. |
| 7,771,935 | B2 | 8/2010 | Liu et al. |
| 7,795,424 | B2 | 9/2010 | Liu et al. |
| 7,883,869 | B2 | 2/2011 | Liu et al. |
| 7,915,201 | B2 | 3/2011 | Franch et al. |
| 7,928,211 | B2 | 4/2011 | Hansen et al. |
| 7,935,658 | B2 | 5/2011 | Morgan et al. |
| 7,972,992 | B2 | 7/2011 | Morgan et al. |
| 7,972,994 | B2 | 7/2011 | Morgan et al. |
| 7,989,395 | B2 | 8/2011 | Morgan et al. |
| 7,998,904 | B2 | 8/2011 | Liu et al. |
| 8,017,323 | B2 | 9/2011 | Liu et al. |
| 8,071,739 | B2 | 12/2011 | Milton et al. |
| 8,114,636 | B2 | 2/2012 | Agnew et al. |
| 8,168,381 | B2 | 5/2012 | Rasmussen |
| 8,183,178 | B2 | 5/2012 | Liu et al. |
| 8,193,335 | B2 | 6/2012 | Carell et al. |
| 8,202,823 | B2 | 6/2012 | Hansen et al. |
| 8,206,901 | B2 | 6/2012 | Freskgard et al. |
| 8,206,914 | B2 | 6/2012 | Liu et al. |
| 8,298,792 | B2 | 10/2012 | Ju et al. |
| 8,410,028 | B2 | 4/2013 | Morgan et al. |
| 8,541,570 | B2 | 9/2013 | Gee et al. |

(Continued)

FOREIGN PATENT DOCUMENTS

| | | |
|---|---|---|
| RU | 2223319 C1 | 2/2004 |
| WO | WO-2000023458 A1 | 4/2000 |

(Continued)

OTHER PUBLICATIONS

Abdel-Magid et al., (1996). "Reductive amination of aldehydes and ketones with sodium triacetoxyborohydride," J. Org. Chem., 61:3849-3862.

Artuso et al., (2007). "Preparation of mono-, di-, and trisubstituted ureas by carbonylation of aliphatic amines with 5,5-dimethyl dithiocarbonate," Synthesis, 22:3497-3506.

Balcom et al., (1953). "Reductions with hydrazine hydrate catalyzed by Raney nickel," J. Am. Chem. Soc., 76:4334.

Barrow et al., (2007). "Design and synthesis of 2,3,5-substituted imidazolidin-4-one inhibitors of BACE-I," Chem. Med. Chem., 2:995-999.

Beugelmans et al., (1995). "Palladium catalyzed reductive deprotection of Alloc: Transprotection and peptide bond formation," Tetrahedron Lett., 36:3129-3132.

Bikard et al., (2010). "Folded DNA in Action: Hairpin Formation and Biological Functions in Prokaryotes," Microbiology And Molecular Biology Reviews, 74:570-588.

(Continued)

*Primary Examiner* — Kaijiang Zhang

(57) ABSTRACT

The present disclosure relates to multifunctional molecules, including molecules according to formula (I):

$$([(B_1)_M\text{-}D\text{-}L_1]_Y\text{—}H_1)_O\text{-}G\text{-}(H_2\text{-}[L_2\text{-}E\text{-}(B_2)_K]_W)_P, \qquad (I)$$

wherein G, $H_1$, $H_2$, D, E, $B_1$, $B_2$, M, K, $L_1$, $L_2$, O, P, Y, and W are defined herein. The present disclosure also relates to methods of preparing and using such multifunctional molecules to identify encoded molecules capable of binding target molecules.

18 Claims, 4 Drawing Sheets

(56) References Cited

U.S. PATENT DOCUMENTS

| | | | |
|---|---|---|---|
| 8,552,173 | B2 | 10/2013 | Skrzypczynski et al. |
| 8,642,514 | B2 | 2/2014 | Neri et al. |
| 8,673,824 | B2 | 3/2014 | Neri et al. |
| 8,691,729 | B2 | 4/2014 | Liu et al. |
| 8,808,984 | B2 | 8/2014 | Pedersen et al. |
| 8,846,883 | B2 | 9/2014 | Brown et al. |
| 8,932,992 | B2 | 1/2015 | Pedersen et al. |
| 8,951,728 | B2 | 2/2015 | Rasmussen |
| 8,951,782 | B2 | 2/2015 | Rasmussen |
| 9,006,150 | B2 | 4/2015 | Hansen et al. |
| 9,096,951 | B2 | 8/2015 | Freskgard et al. |
| 9,109,248 | B2 | 8/2015 | Freskgard et al. |
| 9,121,110 | B2 | 9/2015 | Gouliaev et al. |
| 9,175,340 | B2 | 11/2015 | Liu et al. |
| 10,011,868 | B2 | 7/2018 | Liu et al. |
| 10,036,013 | B2 | 7/2018 | Kim |
| 10,053,725 | B2 | 8/2018 | Liu et al. |
| 10,240,147 | B2 | 3/2019 | Decurtins et al. |
| 10,513,700 | B2 | 12/2019 | Hansen et al. |
| 10,669,538 | B2 | 6/2020 | Pederson et al. |
| 11,186,836 | B2 * | 11/2021 | Watts ..................... C40B 10/00 |
| 2005/0032081 | A1 | 2/2005 | Ju et al. |
| 2005/0247001 | A1 | 11/2005 | Carell et al. |
| 2006/0121470 | A1 | 6/2006 | Pedersen |
| 2006/0269920 | A1 | 11/2006 | Freskgard et al. |
| 2007/0026397 | A1 | 2/2007 | Freskgard et al. |
| 2007/0213519 | A1 | 9/2007 | Gouliaev et al. |
| 2008/0305957 | A1 | 12/2008 | Thisted et al. |
| 2009/0011957 | A1 | 1/2009 | Gouliaev et al. |
| 2009/0143232 | A1 | 6/2009 | Pedersen et al. |
| 2009/0239211 | A1 | 9/2009 | Freskgard et al. |
| 2009/0240030 | A1 | 9/2009 | Ju et al. |
| 2009/0264300 | A1 | 10/2009 | Franch et al. |
| 2010/0261181 | A1 | 10/2010 | Agnew et al. |
| 2011/0020799 | A1 | 1/2011 | Ogi et al. |
| 2012/0053091 | A1 | 3/2012 | Wagner |
| 2012/0071329 | A1 | 3/2012 | Morgan et al. |
| 2012/0142060 | A1 | 6/2012 | Makarov et al. |
| 2012/0245040 | A1 | 9/2012 | Morgan et al. |
| 2012/0252010 | A1 | 10/2012 | Balasubramanian et al. |
| 2013/0005581 | A1 | 1/2013 | Hansen et al. |
| 2013/0040823 | A1 | 2/2013 | Freskgard et al. |
| 2013/0046083 | A1 | 2/2013 | Brown et al. |
| 2013/0231473 | A1 | 9/2013 | Brown et al. |
| 2013/0237459 | A1 | 9/2013 | Rasmussen |
| 2013/0280700 | A1 | 10/2013 | Ju et al. |
| 2013/0281324 | A1 | 10/2013 | Gouliaev et al. |
| 2014/0235509 | A1 | 8/2014 | Rasmussen |
| 2014/0295414 | A1 | 10/2014 | Salic et al. |
| 2014/0315762 | A1 | 10/2014 | Keefe et al. |
| 2014/0336079 | A1 | 11/2014 | Agnew et al. |
| 2015/0050697 | A1 | 2/2015 | Kim |
| 2015/0051088 | A1 | 2/2015 | Kim |
| 2015/0051116 | A1 | 2/2015 | Kim |
| 2015/0126381 | A1 | 5/2015 | Rasmussen |
| 2015/0203841 | A1 | 7/2015 | Rasmussen |
| 2015/0211002 | A1 | 7/2015 | Keefe et al. |
| 2015/0232957 | A1 | 8/2015 | Fournier-Wirth et al. |
| 2015/0315569 | A1 | 11/2015 | Weisinger et al. |
| 2015/0321164 | A1 | 11/2015 | Li et al. |
| 2015/0344872 | A1 | 12/2015 | Harbury et al. |
| 2016/0040158 | A1 | 2/2016 | Wagner et al. |
| 2016/0222054 | A1 | 8/2016 | Brown et al. |
| 2016/0314242 | A1 | 10/2016 | Schnall-Levin et al. |
| 2016/0369267 | A1 | 12/2016 | Wagner |
| 2017/0009225 | A1 | 1/2017 | Franch et al. |
| 2017/0198336 | A1 | 7/2017 | Reddavide et al. |
| 2018/0002688 | A1 | 1/2018 | Keefe et al. |
| 2018/0135043 | A1 | 5/2018 | Wong et al. |
| 2019/0112730 | A1 | 4/2019 | He et al. |
| 2019/0136227 | A1 | 5/2019 | Freskgard et al. |
| 2019/0169607 | A1 | 6/2019 | Watts |
| 2020/0216836 | A1 | 7/2020 | Franch et al. |
| 2020/0263163 | A1 | 8/2020 | Watts et al. |
| 2020/0332441 | A1 | 10/2020 | Watts et al. |

FOREIGN PATENT DOCUMENTS

| | | |
|---|---|---|
| WO | WO-2001096335 A1 | 12/2001 |
| WO | WO-2003078446 A2 | 9/2003 |
| WO | WO-2004110964 A2 | 12/2004 |
| WO | WO-2005003778 A2 | 1/2005 |
| WO | WO-2006047791 A2 | 5/2006 |
| WO | WO-2006079061 A2 | 7/2006 |
| WO | WO-2007062664 A3 | 6/2007 |
| WO | WO-2009077173 A2 | 6/2009 |
| WO | WO-2009079624 A1 | 6/2009 |
| WO | WO-2011127933 A1 | 10/2011 |
| WO | WO-2012004204 A1 | 1/2012 |
| WO | WO-2015021080 A2 | 2/2015 |
| WO | WO-2015135856 A1 | 9/2015 |
| WO | WO-2016025804 A1 | 2/2016 |
| WO | WO-2016165621 A1 | 10/2016 |
| WO | WO-2017062973 A2 | 4/2017 |
| WO | WO-2017189631 A2 | 11/2017 |
| WO | WO-2017218293 A1 | 12/2017 |
| WO | WO-2018118897 A1 | 6/2018 |
| WO | WO-2018166532 A1 | 9/2018 |
| WO | WO-2018204420 A1 | 11/2018 |
| WO | WO-2019060856 A1 | 3/2019 |

OTHER PUBLICATIONS

Brazda et al., (2011). "Cruciform structures are a common DNA feature important for regulating biological processes," BMC Molecular Biology, 12:33, 16 pages.

Brenner et al., (1992). "Encoded combinatorial chemistry," Proc Natl Acad Sci USA, 89(12):5381-5383.

Buller et al., (2008). "Design and synthesis of a novel DNA-encoded chemical library using Diels-Alder cycloadditions," Biorganic & Medicinal Chemistry Letters, 18:5926-5931.

Carriero et al., (2003). "Template-Mediated Synthesis of Lariat RNA and DNA," Journal of Organic Chemistry, 68:8328-8338.

Chauleta et al., (2011). "Design, synthesis and biological evaluation of new thalidomide analogues as TNF-a and IL-6 production inhibitors," Bioorg. Med. Chem. Lett., 21:1019-1022.

Deprez-Poulain et al., (2007). "Convenient synthesis of 4H-1,2,4-triazole-3-thiols using di-2-pyridylthionocarbonate," Tetrahedron Lett., 48:8157-8162.

Domaratzki, (2009). "Hairpin Structures Defined by DNA Trajectories," Theory Comput Syst., 44:432-454.

Durand et al., (1990). "Circular dichroism studies of an oligodeoxyribonucleotide containing a hairpin loop made of a hexaethylene glycol chain: conformation and stability," Nucleic acids research, 18:6353-6359.

Elia, (2010). "Protein Biotinylation," Current Protocols in Protein Science, 3.6.1-3.6.21.

Fedorova et al., (1996). "Cyanogen Bromide-Induced Chemical Ligation: Mechanism and Optimization of the Reaction Conditions," Nucleosides and Nucleotides, 15:1137-1147.

Franzini et al., (2014). "Systematic Evaluation and Optimization of Modification Reactions of Oligonucleotides with Amines and Carboxylic Acids for the Synthesis of DNA-Encoded Chemical Libraries," Bioconjugate Chemistry, 25(8):1453-1461.

Giaever et al., (2002). "Functional profiling of the *Saccharomyces cerevisiae* genome," Nature, 418:387-391.

Gryaznov et al., (1993). "Chemical ligation of oligonucleotides in the presence and absence of a template," J. Am. Chem. Soc., 115:3808-3809.

Gurevich et al., (1991). "Preparative in vitro mRNA synthesis using SP6 and T7 RNA polymerases," Analytical Biochemistry, 195:207-213.

Halpin et al., (2004). "DNA Display III. Solid Phase Organic Synthesis on Unprotected DNA," PLoS Biology, 2(7):1031-1038.

Hong et al., (2009). "Analysis and Optimization of Copper-Catalyzed Azide-Alkyne Cycloaddition for Bioconjugation," Angewandte Chem Int Ed Engl., 48:9879-9883, 13 pages.

Inglis et al., (2006). "Synthesis of N-benzylated-2-aminoquinolines as ligands for the Tec SH3 domain," Bioorg. Med. Chem. Lett., 16:387-390.

(56)                  References Cited

OTHER PUBLICATIONS

Kanan et al., (2004). "Reaction discovery enabled by DNA-templated synthesis and in vitro selection," Nature, 431:545-549.

Li et al., (2011). "Copper-free Sonogashira cross-coupling for functionalization of alkyne encoded proteins in aqueous medium and in bacterial cells," J. Am. Chem. Soc., 133:15316-15319, 10 pages.

Liang et al., (2005). "Cooper-free 15 sonogashira coupling reaction with PdC12 in water under aerobic conditions," J. Org. Chem., 70:391-393.

Lubbad et al., (2002). "Micropreparative fractionation of DNA fragments on metathesis-based monoliths: influence of stoichiometry on separation," J Chromatogr A., 959(1-2):121-9.

Lubbad et al., (2011). "Ring-opening metathesis polymerization-derived monolithic anion exchangers for the fast separation of double-stranded DNA fragments," J Chromatogr A., 1218(17):2362-7.

Lubbad et al., (2011). "Ring-opening metathesis polymerization-derived monolithic strong anion exchangers for the separation of 5'-phosphorylated oligodeoxythymidylic acids fragments," J Chromatogr A., 1218(49):8897-902.

Mandal et al., (2014). "RIP3 induces apoptosis independent of pronecrotic kinase activity," Mol. Cell, 56:481-495.

Manocci et al., (2011). "20 years of DNA-encoded chemical libraries," Chem. Commun., 47:12747-12753.

Marziale et al., (2011). "An efficient protocol for copper-free 20 palladium-catalyzed Sonogashira crosscoupling in aqueous media at low temperatures," Tetrahedron Lett., 52:6355-6358.

Mukhopadhyay et al., (2008). "Dowex 50W: A highly efficient and recyclable green catalyst for the construction of the 2-substituted benzimidazole moiety in aqueous medium," Catal. Commun., 9:2392-2394.

Plieva et al., (2004). "Characterization of polyacrylamide based monolithic columns," J. Sep. Sci., 27:828-836.

Plieva et al., (2006). "Macroporous polyacrylamide monolithic gels with immobilized metal affinity ligands: the effect of porous structure and ligand coupling chemistry on protein binding," J. Mol. Recognit., 19:305-312.

Plieva et al., (2008). "Cryogel applications in microbiology," Trends in Microbiology, 16(11):543-551.

Pokrovskaya et al., (1994). "In Vitro Transcription: Preparative RNA Yields in Analytical Scale Reactions," Analytical Biochemistry, 220:420-423.

Potewar et al., (2008). "Catalyst-free efficient synthesis of 2-aminothiazoles in water at ambient temperature," Tetrahedron 64:5019-5022.

Roughley et al., (2011). "The medicinal chemist's toolbox: an analysis of reactions used in the pursuit of drug candidates," J. Med. Chem., 54:3451-3479.

Satz et al., (2015). "DNA Compatible Multistep Synthesis and Applications to DNA Encoded Libraries," Bioconjugate Chemistry, 26(8):1623-1632.

Shabarova et al., (1991). "Chemical ligation of DNA: the first non-enzymatic assembly of a biologically active gene," Nucleic Acids Research, 19:4247-4251.

Svoboda et al., (2006). "Hairpin RNA: a secondary structure of primary importance," Cellular and Molecular Life Sciences, 63(7):901-908.

Wang et al., (2011). "Asymmetric synthesis of LFA-1 inhibitor B1RT2584 on metric ton scale," Org. Process Res. Dev., 15:1185-1191.

Witt et al., (2000). "Synthesis and reactions of some 2-vinyl-3H-quinazolin-4-ones," Tetrahedron, 56:7245-7253.

Xie et al., (1996). "Preparation of porous hydrophilic monoliths: Effect of the polymerization conditions on the porous properties of poly (acrylamide-co-N,N'-methylenebisacrylamide) monolithic rods," J. Polym. Sci. A Polym. Chem., 35:1013-1021.

* cited by examiner $$([(B_1)_{(M-1)}\!-\!D\!-\!L_1]_Y\!-\!H_1) + G' + (H_2\!-\![L_2\!-\!E\!-\!(B_2)_{(K-1)}]_W)$$

$$\downarrow$$

$$([(B_1)_{(M-1)}\!-\!D\!-\!L_1]_Y\!-\!H_1)_O\!-\!G\!-\!(H_2\!-\![L_2\!-\!E\!-\!(B_2)_{(K-1)}]_W)_P$$

$$\Big\downarrow B_1 \text{ and/or } B_2$$

Figure 4:
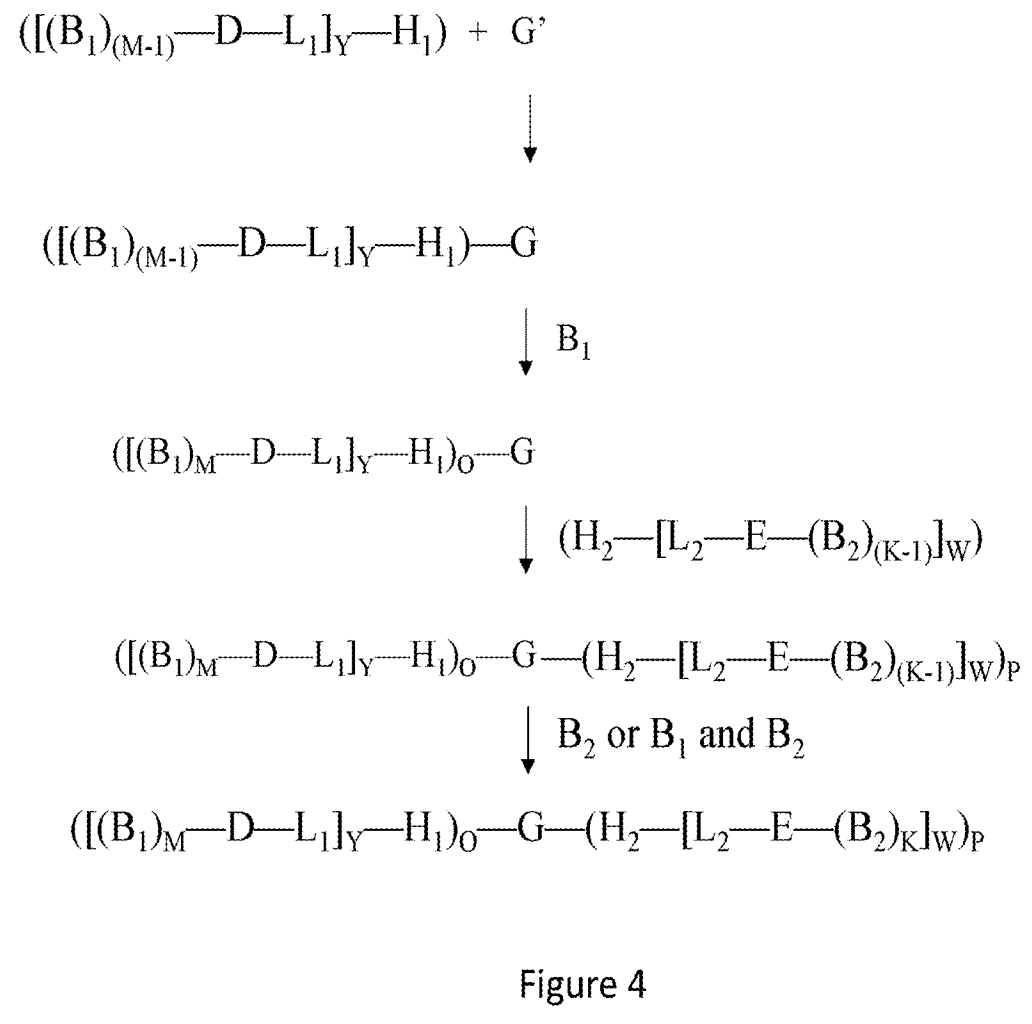

$$\downarrow$$

$$([(B_1)_{(M-1)} - D - L_1]_Y - H_1) - G$$

$$\downarrow B_1$$

$$([(B_1)_M - D - L_1]_Y - H_1)_O - G$$

$$\downarrow (H_2 - [L_2 - E - (B_2)_{(K-1)}]_W)$$

$$([(B_1)_M - D - L_1]_Y - H_1)_O - G - (H_2 - [L_2 - E - (B_2)_{(K-1)}]_W)_P$$

$$\downarrow B_2 \text{ or } B_1 \text{ and } B_2$$

OLIGONUCLEOTIDE DIRECTED AND RECORDED COMBINITORIAL SYNTHESIS OF ENCODED PROBE MOLECULES

CROSS-REFERENCE TO RELATED APPLICATIONS

This application is a continuation application of U.S. application Ser. No. 16/306,356, filed Jun. 8, 2017, which is a U.S. national stage application of PCT/US2017/036582, filed internationally on Jun. 8, 2017, which claims priority to U.S. provisional application Ser. No. 62/351,046, filed Jun. 16, 2016, each of which is hereby incorporated by reference in its entirety.

TECHNICAL FIELD

The present invention relates to multifunctional molecules, and methods of preparing and using such multifunctional molecules. The present invention further provides methods of using the multifunctional molecules to identify encoded molecules capable of binding target molecules or possessing other desirable properties like target molecule selectivity or cell permeability.

BACKGROUND

There are basically three ways that molecules with desired functions, like drugs for example, are discovered. They are discovered in nature, they are rationally designed, and they are found by trial and error. In many cases, the trial and error method arguably holds the most promise, but it can be stunningly inefficient. The key to making the trial and error method more efficient has been to create combinatorial libraries of molecules that can be synthesized in vast numbers and tested for possession of desired properties. The need to efficiently discover new molecules through trial and error gave rise to the field of combinatorial chemistry.

There are three major problems with synthesizing and testing combinatorial libraries. First, many of the methods for preparing probe molecules from combinatorial libraries are limited by the types and number of successive chemical subunits or building blocks that can be assembled. Second, many of the methods for assembling successive building blocks are limited by the reaction efficiency of each step. Third, it is understood that to preserve efficiency, vast numbers of probe molecules should be simultaneously tested for possession of desired properties. It is also understood that libraries with a sufficient diversity of molecular shapes may possess only a few copies of any given molecule. The low number of copies frustrates identification of probe molecules possessing the desired properties. Therefore, each probe molecule should be labeled with a unique identifier so that researchers can identify the desired probe molecules.

Researchers have developed DNA encoded probe molecules to solve some of these problems. Some researchers have used DNA oligonucleotides as templates to direct one or more steps of combinatorial synthesis. Others have used DNA oligonucleotides to record combinatorial synthesis and uniquely label the probe molecules, so that PCR (polymerase chain reaction) amplification can be used to identify molecular probes that remain bound to the target molecule. Still, other researchers have used DNA oligonucleotides to direct one or more steps of combinatorial synthesis and to label the probe molecule with a unique identifier.

Despite the success of many of these methods, some problems still remain. Existing methods still suffer from low efficiency of the successive reaction steps to synthesize probe molecules. Existing methods also have difficulty detecting probe molecules that bind target molecules tightly, but are present in low numbers. This difficulty can result in a false negative. There is a need for a method of producing oligonucleotide probe molecules that increases the reaction efficiency of the successive reaction steps. There is also a need to be able to identify probe molecules binding target molecules, even though those probe molecules may be present in low numbers.

SUMMARY

The present disclosure relates to encoded molecules. In certain embodiments, the encoded molecules are molecules according to formula (I), $$([(B_1)_M\text{-}D\text{-}L_1]_Y\text{—}H_1)_O\text{-}G\text{-}(H_2\text{-}[L_2\text{-}E\text{-}(B_2)_K]_W)_P \qquad (I)$$

wherein

G is an oligonucleotide, the oligonucleotide comprising at least two coding regions and at least one terminal coding region, wherein the at least two coding regions are single stranded and the at least one terminal coding region is single or double stranded;

$H_1$ is a hairpin structure comprising oligonucleotides, wherein $H_1$ terminates in a 5' end and is attached to an end of the oligonucleotide G;

$H_2$ is a hairpin structure comprising oligonucleotides, wherein $H_2$ terminates in a 3' end and is attached to an end of the oligonucleotide G;

D is a first building block;

E is a second building block, wherein D and E are the same or different;

$B_1$ is a positional building block and M represents an integer from 1 to 20;

$B_2$ is a positional building block and K represents an integer from 1 to 20, wherein $B_1$ and $B_2$ are the same or different, wherein M and K are the same or different;

$L_1$ is a linker that operatively links $H_1$ to D;

$L_2$ is a linker that operatively links $H_2$ to E;

O is an integer from zero to 1;

P is an integer from zero to 1;

provided that at least one of O and P is 1;

Y is an integer from 1 to 5;

W is an integer from 1 to 5; and wherein at least one of each positional building block $B_1$ at position M and $B_2$ at position K is identified by one of the coding regions, and wherein at least one of the first building block D and second building block E is identified by the at least one terminal coding region.

In certain embodiments of the molecule of formula (I). G comprises a sequence represented by the formula ($C_N$—($Z_N$—$C_{N+1}$)$_A$), wherein C is a coding region, Z is a non-coding region, N is an integer from 1 to 20, and A is an integer from 1 to 20; wherein each non-coding region contains from 4 to 50 nucleotides and is optionally double stranded. In certain embodiments of the molecule of formula (I), one of O or P is zero. In certain embodiments of the molecule of formula (I), at least one of Y and W is an integer from 1 to 2. In certain embodiments of the molecule of formula (I), each coding region contains from 6 to 50 nucleotides. In certain embodiments of the molecule of formula (I), at least one of $H_1$ and $H_2$ comprises from 20 to 90 nucleotides. In certain embodiments of the molecule of formula (I), each coding region contains from 12 to 40 nucleotides. In certain embodiments of the molecule of formula (I), P is zero, Y is an integer from 1 to 2, and each coding region contains from 12 to 40 nucleotides. In certain embodiments of the molecule of formula (I), O is zero, W is an integer from 1 to 2, and each coding region contains from 12 to 40 nucleotides.

The present disclosure relates to a method of identifying probe molecules capable of binding or selecting for a target molecule including exposing the target molecule to a pool of probe molecules, wherein the probe molecules are according to formula (I) above, removing at least one probe molecule that does not bind the target molecule, amplifying at least one oligonucleotide G from the at least one probe molecule that was not removed from the target molecule to form a copy sequence, sequencing at least one oligonucleotide G of the copy sequence to identify the at least two coding regions of the probe molecule to further identify at least one of each positional building block $B_1$ at position M and $B_2$ at position K, and to identify the at least one terminal coding region of the copy molecule to further identify at least one of the first building block D and the second building block E of the probe molecule.

The present disclosure relates to a method of forming a molecule of formula (I). In certain embodiments, the method of forming a molecule of formula (I) includes:

providing at least one hybridization array, the at least one hybridization array comprising at least one single stranded anti-codon oligomer immobilized on the at least one hybridization array, wherein the at least one single stranded anti-codon oligomer immobilized on the at least one hybridization array is capable of hybridizing to a coding region of a molecule of formula (II):

$$([(B_I)_{(M-I)}\text{-D-L}_1]_Y\text{—H}_I)_O\text{-G-(H}_2\text{-[L}_2\text{-E-(B}_2)_{(K-1)}]_W)_P \qquad (II)$$

wherein

G is an oligonucleotide, the oligonucleotide comprising at least two coding regions and at least one terminal coding region, wherein the at least two coding regions are single stranded and the at least one terminal coding region is single or double stranded;

$H_1$ is a hairpin structure comprising oligonucleotides, wherein $H_1$ terminates in a 5' end and is attached to an end of the oligonucleotide G;

$H_2$ is a hairpin structure comprising oligonucleotides, wherein $H_2$ terminates in a 3' end and is attached to an end of the oligonucleotide G;

D is a first building block;

E is a second building block, wherein D and E are the same or different;

$B_1$ is a positional building block and M represents an integer from 1 to 20;

$B_2$ is a positional building block and K represents an integer from 1 to 20, wherein $B_1$ and $B_2$ are the same or different, wherein M and K are the same or different;

$L_1$ is a linker that operatively links $H_1$ to D;

$L_2$ is a linker that operatively links $H_2$ to E;

O is an integer from zero to 1;

P is an integer from zero to 1;

provided that at least one of O and P is 1;

Y is an integer from 1 to 5;

W is an integer from 1 to 5; and wherein at least one of each positional building block $B_1$ at position M and $B_2$ at position K is identified by one of the coding regions and wherein at least one of the first building block D and second building block E is identified by the at least one terminal coding region;

sorting the pool of molecules of formula (II) into sub-pools by hybridizing a coding region of the sub-pool of molecules of formula (II) to the at least one single stranded anti-codon oligomer immobilized on the at least one hybridization array;

a step of optionally releasing the sub-pool of molecules of formula (II) from the at least one hybridization array into separate containers;

providing at least one of building block $B_1$ and $B_2$; and reacting the at least one of building block $B_1$ and $B_2$ with the molecule of formula (II) to form a sub-pool of molecules of formula (I):

$$([(B_1)_M\text{-D-L}_1]_Y\text{—H}_1)_O\text{-G-(H}_2\text{-[L}_2\text{-E-(B}_2)_K]_W)_P, \qquad (I)$$

wherein

G is an oligonucleotide, the oligonucleotide comprising at least two coding regions and at least one terminal coding region, wherein each coding region is single stranded and the at least one terminal coding region is single or double stranded;

$H_1$ is a hairpin structure comprising oligonucleotides, wherein $H_1$ terminates in a 5' end and is attached to an end of the oligonucleotide G;

$H_2$ is a hairpin structure comprising oligonucleotides, wherein $H_2$ terminates in a 3' end and is attached to an end of the oligonucleotide G;

D is a first building block;

E is a second building block, wherein D and E are the same or different;

$B_1$ is a positional building block and M represents an integer from 1 to 20;

$B_2$ is a positional building block and K represents an integer from 1 to 20, wherein $B_1$ and $B_2$ are the same or different, wherein M and K are the same or different;

$L_1$ is a linker that operatively links $H_1$ to D;

$L_2$ is a linker that operatively links $H_2$ to E;

O is an integer from zero to 1;

P is an integer from zero to 1;

provided that at least one of O and P is 1;

Y is an integer from 1 to 5;

W is an integer from 1 to 5; and wherein at least one of each positional building block $B_1$ at position M and $B_2$ at position K is identified by one of the coding regions, and wherein at least one of the first building block D and second building block E is identified by the at least one terminal coding region.

In certain embodiments of the method of forming a molecule of formula (I), the molecule of formula (II) is prepared by:

providing a pool of oligonucleotides, the oligonucleotides G' comprising at least two coding regions and at least one terminal coding region, wherein the at least two coding regions are single stranded, the at least one terminal coding region is single stranded, and the at least one terminal coding region at a 5' and/or a 3' end of the oligonucleotides G' is different;

providing at least one charged carrier anti-codon, the at least one charged carrier anti-codon having the formula of $([(B_1)_{(M-1)}\text{-D-L}_1]_Y\text{-H}_1)$ and/or $(H_2\text{-[L}_2\text{-E-(B}_2)_{(K-1)}]_W)$;

combining the pool of oligonucleotides G' and the at least one charged carrier anti-codon;

bonding the 5' end of the at least one oligonucleotide G' to the 3' end of $H_1$, and/or bonding the 3' end of the at least one oligonucleotide G' to the 5' end of $H_2$ to form a pool of molecules of formula (II):

$$([(B_1)_{(M-1)}\text{-D-L}_1]_Y\text{-H}_1)_O\text{-G-(H}_2\text{-[L}_2\text{-E-(B}_2)_{(K-1)}]_W)_P, \qquad (II)$$

wherein G, $H_1$, $H_2$, D, E, $B_1$, $B_2$, $L_1$, $L_2$, O, P, Y, and W are as defined in formula (I) above, and M and K are one.

In certain embodiments of the method of forming a molecule of formula (I), the method further includes removing a portion of oligonucleotide from the at least one terminal coding region of a molecule of formula (I) or (II). In certain embodiments of the method of forming a molecule of formula (I), the method further includes ligating at least one of $H_1$ to G and $H_2$ to G. In certain embodiments of the method of forming a molecule of formula (I), G comprises a sequence represented by the formula ($C_N$—$(Z_N$—$C_{N+1})_A$), wherein C is a coding region, Z is a non-coding region, N is an integer from 1 to 20, and A is an integer from 1 to 20; wherein each non-coding region contains from 4 to 50 nucleotides and is optionally double stranded. In certain embodiments of the method of forming a molecule of formula (I), one of O or P is zero. In certain embodiments of the method of forming a molecule of formula (I), at least one of Y and W is an integer from 1 to 2. In certain embodiments of the method of forming a molecule of formula (I), at least one of $H_1$ and $H_2$ comprises from 20 to 90 nucleotides. In certain embodiments of the method of forming a molecule of formula (I), P is zero, Y is an integer from 1 to 2, and each coding region contains from 12 to 40 nucleotides; or O is zero, W is an integer from 1 to 2, and each coding region contains from 12 to 40 nucleotides.

BRIEF DESCRIPTION OF THE DRAWINGS

The foregoing summary, as well as the following detailed description of the embodiments, will be better understood when read in conjunction with the attached drawings. For the purpose of illustration, there are shown in the drawings some embodiments, which may be preferable. It should be understood that the embodiments depicted are not limited to the precise details shown.

FIG. 3 is a flow diagram which illustrates an embodiment of a method for forming a molecule of formula (I).

FIG. 4 is a flow diagram which illustrates an embodiment of a method for forming a molecule of formula (I).

DETAILED DESCRIPTION

Figure 1:
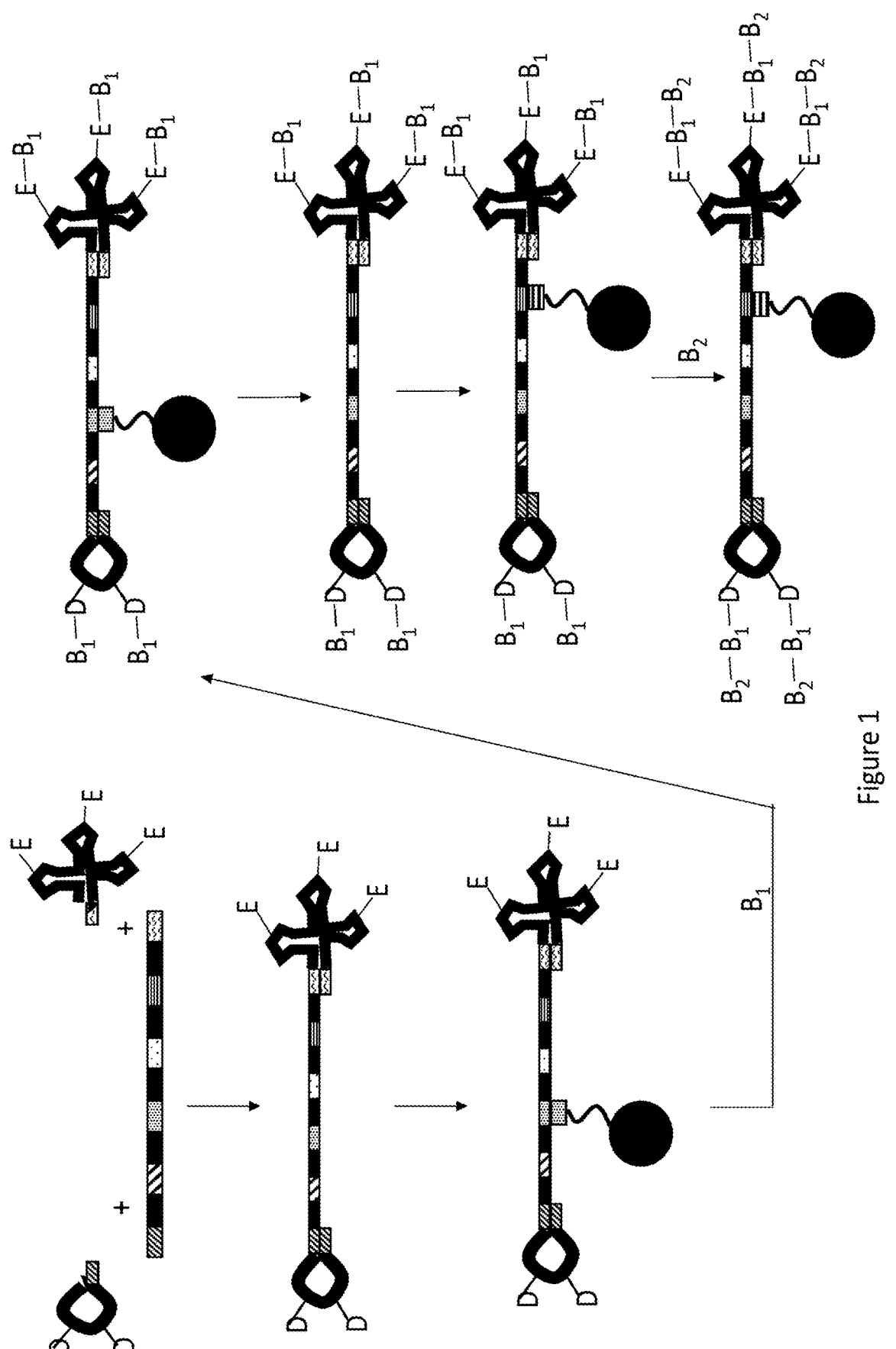
FIG. 1 is an illustration of an embodiment of a method of preparing a multifunctional molecule.

Unless otherwise noted, all measurements are in standard metric units.

Unless otherwise noted, all instances of the words "a," "an," or "the" can refer to one or more than one of the word that they modify.

Unless otherwise noted, the phrase "at least one of" means one or more than one of an object. For example, "at least one of $H_1$ and $H_2$" means $H_1$, $H_2$, or both.

Unless otherwise noted, the term "about" refers to ±10% of the non-percentage number that is described, and rounded to the nearest whole integer. For example, about 100 mm, would include 90 to 110 mm. Unless otherwise noted, the term "about" refers to ±5% of a percentage number. For example, about 20% would include 15 to 25%. When the term "about" is discussed in terms of a range, then the term refers to the appropriate amount less than the lower limit and more than the upper limit. For example, from about 100 to about 200 mm would include from 90 to 220 mm.

Unless otherwise noted, the term "hybridize," "hybridizing," and "hybridized" includes Watson-Crick base pairing, which includes guanine-cytosine and adenine-thymine (G-C and A-T) pairing for DNA and guanine-cytosine and adenine-uracil (G-C and A-U) pairing for RNA. This these terms are used in the context of the selective recognition of a strand of nucleotides for a complementary strand of nucleotides, called an anti-codon or anti-coding region.

The phrases "selectively hybridizing," "selective hybridization" and "selectively sorting" refer to a selectivity of from 5:1 to 100:1 or more of a complementary strand relative to a non-complementary strand.

The term "multifunctional molecule" refers to a molecule of the present disclosure that contains an oligonucleotide and at least one encoded portion.

The term "encoded portion" refers to one or more parts of the multifunctional molecule that only contain building blocks, such as the first building block, the second building block, and positional building blocks $B_1$ and $B_2$. The term "encoded portion" does not include a hairpin structure or linker, even though these structures may be added as part of the process of synthesizing the encoded portion.

The term "encoded molecule" refers to a molecule that would be or is formed if the encoded portion of the multifunctional molecule were removed or separated from the rest of the multifunctional molecule.

The term "probe molecule" refers to a molecule that is used to determine which encoded portion of a multifunctional molecule or encoded molecule is capable of binding a target molecule or selecting for desirable properties like target molecule selectivity or cell permeability.

The term "target molecule" refers to a molecule or structure. For example, structures include multi-macromolecular complexes, such as ribosomes, and liposomes.

The term "probe molecule" can include a multifunctional molecule.

The term "encoded probe molecule" is used interchangeably with the term multifunctional molecule.

The term "polydisplay" refers to a multifunctional molecule having at least two encoded portions.

In the present disclosure, the hyphen or dashes in a molecular formula indicate that the parts of the formula are directly connected to each other through a covalent bond or hybridization.

Unless otherwise noted, all ranges of nucleotides and integer values include all intermediate integer numbers as well as the endpoints. For example, the range of from 5 to 10 oligonucleotides would be understood to include 5, 6, 7, 8, 9, and 10 nucleotides.

In certain embodiments, the present disclosure relates to multifunctional molecules that contain at least one oligonucleotide portion and at least one encoded portion, wherein the oligonucleotide portion directed or encoded the synthesis of the at least one encoded portion using combinatorial chemistry. In certain embodiments, the oligonucleotide portion of the multifunctional molecule can identify the at least one encoded portion of the multifunctional molecule. In certain embodiments, the multifunctional molecules contain hairpin structures attached to at least one end of the multifunctional molecule, wherein a hairpin structure allows for the poly display of multiple encoded portions of the multifunctional molecule. Without wishing to be bound by theory, it is believed that the polydisplay of multiple encoded portions allows a multifunctional molecule of the present disclosure to be more efficiently selected as having a desired property, even though the multifunctional molecule may be present in low numbers, low concentration, low relative concentration to other probe molecules, or have lesser degrees of the desired property. In certain embodiments, a multifunctional molecule of the present disclosure contains at least one oligonucleotide or oligonucleotide portion that contains at least two coding regions and at least one terminal coding region, wherein the at least two coding regions and at least one terminal coding region correspond to and can be used to identify the sequence of building blocks in the encoded portion. In certain embodiments, the at least one oligonucleotide or oligonucleotide portion can be amplified by PCR to produce copies of the at least one oligonucleotide or oligonucleotide portion and the original or copies can be sequenced to determine the identity of the at least two coding regions and at least one terminal coding region of the multifunctional molecule. In certain embodiments, the identity of the at least two coding regions and at least one terminal coding region can be correlated to the series of combinatorial chemistry steps used to synthesize the encoded portion of the multifunctional molecule to which the PCR copy corresponds.

In certain embodiments, the present disclosure also relates to methods of forming multifunctional molecules, and to methods of exposing target molecules to the multifunctional molecules to identify which encoded portion, and therefore which encoded molecule, exhibits a desired property, including but not limited to the capability of binding a target molecule or molecules, of not binding other anti-target molecules, of being resistant to chemical changes made by enzymes, of being readily chemically changed by enzymes, of having degrees of water solubility, and of being cell-permeable.

In certain embodiments, the molecule of formula (I) is a multifunctional molecule. In certain embodiments of the molecule of formula (I), G is an oligonucleotide that directed or selected for the synthesis of the encoded portion. In certain embodiments of the molecule of formula (I), $(B_1)_M$-D and E-$(B_2)_K$ each represent an encoded portion. In certain embodiments of the molecule of formula (I), the molecule contains an oligonucleotide portion and at least one encoded portion. It is understood that many of the structural features of the oligonucleotide G are discussed herein in terms of their having directed or encoded the synthesis of the at least one encoded portion of the molecule of formula (I). It is understood that many of the structural features of the oligonucleotide G of the molecule of formula (I) are discussed in terms of the ability of the oligonucleotide G, or a PCR copy thereof, to identify the synthesis steps used to prepare the molecule of formula (I) and therefore the sequence and/or identity of building blocks and the chemical reactions used to form the encoded portions of the molecule for formula (I).

In certain embodiments of the molecule of formula (I), G includes or is an oligonucleotide. In certain embodiments, the oligonucleotide contains at least two coding regions, wherein from about 1% to about 100%, including from about 50% to about 100%, including from about 90% to about 100%, of the coding regions are single stranded. In certain embodiments, the oligonucleotide G contains at least one terminal coding region, wherein one or two of the terminal coding regions are single stranded. In certain embodiments, the oligonucleotide G contains at least one terminal coding region, wherein one or two of the terminal coding regions are double stranded.

In certain embodiments of the molecule of formula (I), the oligonucleotide G contains at least two coding regions, including from 2 to about 21 coding regions, including from 3 to 10 coding regions, including from 3 to 5 coding regions. In certain embodiments, if the number of coding regions falls below 2, then the number of possible encoded portions that can be synthesized becomes too small to be practical. In certain embodiments, if the number of coding regions exceeds 20, then synthetic inefficiencies interfere with accurate synthesis.

In certain embodiments of the molecule of formula (I), the at least two coding regions contain from about 6 to about 50 nucleotides, including from about 12 to about 40 nucleotides, including from about 8 to about 30 nucleotides. In certain embodiments, if the coding region contains less than about 6 nucleotides then the coding region cannot accurately direct synthesis of the encoded portion. In certain embodiments, if the coding region contains more than about 50 nucleotides then the coding region could become cross reactive. Such cross reactivity would interfere with the ability of the coding regions to accurately direct and identify the synthesis steps used to synthesize the encoded portion of a molecule of formula (I).

In certain embodiments of the molecule of formula (I), a purpose of the oligonucleotide G is to direct the synthesis of at least one encoded portion of the molecule of formula (I) by selectively hybridizing to a complementary anti-coding strand. In certain embodiments, the coding regions are single stranded to facilitate hybridization with a complementary strand. In certain embodiments, from 70% to 100%, including from 80% to 99%, including from 80 to 95%, of the coding regions are single stranded. It is understood that the complementary strand for a coding region, if present, could be added after steps of encoding the encoded portion of the molecule of formula (I) during synthesis.

In certain embodiments, the oligonucleotide can contain natural and unnatural nucleotides. Suitable nucleotides include the natural nucleotides of DNA (deoxyribonucleic acid), including adenine (A), guanine (G), cytosine (C), and thymine (T), and the natural nucleotides of RNA (ribonucleic acid), adenine (A), uracil (U), guanine (G), and cytosine (C). Other suitable bases include natural bases, such as deoxyadenosine, deoxythymidine, deoxyguanosine, deoxycytidine, inosine, diamino purine; base analogs, such as 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, 4-((3-(2-(2-(3-aminopropoxy)ethoxy)ethoxy)propyl)amino)pyrimidin-2(1H)-one, 4-amino-5-(hepta-1,5-diyn-1-yl)pyrimidin-2(1H)-one, 6-methyl-3,7-dihydro-2H-pyrrolo[2,3-d]pyrimidin-2-one, 3H-benzo[b]pyrimido[4,5-e][1,4]oxazin-2(10H)-one, and 2-thiocytidine; modified nucleotides, such as 2'-substituted nucleotides, including 2'-O-methylated bases and 2'-fluoro bases; and modified sugars, such as 2'-fluororibose, ribose, 2'-deoxyribose, arabinose, and hexose; and/or modified phosphate groups, such as phosphorothioates and 5'-N-phosphoramidite linkages. It is understood that an oligonucleotide is a polymer of nucleotides. The terms "polymer" and "oligomer" are used herein interchangeably. In certain embodiments, the oligonucleotide does not have to contain contiguous bases. In certain embodiments, the oligonucleotide can be interspersed with linker moieties or non-nucleotide molecules.

In certain embodiments of the molecule of formula (I), the oligonucleotide G contains from about 60% to 100%, including from about 80% to 99%, including from about 80% to 95% DNA nucleotides. In certain embodiments, the oligonucleotide contains from about 60% to 100%, including from about 80% to 99%, including from about 80% to 95% RNA nucleotides.

In certain embodiments of the molecule of formula (I), the oligonucleotide G contains at least two coding regions, wherein the at least two of the coding regions overlap so as to be coextensive, provided that the overlapping coding regions only share from about 30% to 1% of the same nucleotides, including about 20% to 1%, including from about 10% to 2%. In certain embodiments of the molecule of formula (I), excluding the terminal coding regions, the oligonucleotide G is from about 40% to 100%, including about from 60% to 100%, including about from 80% to 100%, single stranded. In certain embodiments of the molecule of formula (I), the oligonucleotide G contains at least two coding regions, wherein at least two of the coding regions are adjacent. In certain embodiments of the molecule of formula (I), the oligonucleotide G contains at least two coding regions, wherein the at least two coding regions are separated by regions of nucleotides that do not direct or record synthesis of an encoded portion of the molecule of formula (I).

The term "non-coding region," when present, refers to a region of the oligonucleotide that either cannot hybridize with a complementary strand of nucleotides to direct the synthesis of the encoded portion of the molecule of formula (I) or does not correspond to any anti-coding oligonucleotide used to sort the molecules of formula (I) during synthesis. In certain embodiments, non-coding regions are optional. In certain embodiments, the oligonucleotide contains from 1 to about 20 non-coding regions, including from 2 to about 9 non-coding regions, including from 2 to about 4 non-coding regions. In certain embodiments, the non-coding regions contain from about 4 to about 50 nucleotides, including from about 12 to about 40 nucleotides, and including from about 8 to about 30 nucleotides.

In certain embodiments of the molecule of formula (I), one purpose of the non-coding regions is to separate coding regions to avoid or reduce cross-hybridization, because cross-hybridization would interfere with accurate encoding of the encoded portion of the molecule of formula (I). In certain embodiments, one purpose of the non-coding regions is to add functionality, other than just hybridization or encoding, to the molecule formula (I). In certain embodiments, one or more of the non-coding regions can be a region of the oligonucleotide that is modified with a label, such as a fluorescent label or a radioactive label. Such labels can facilitate the visualization or quantification of molecules for formula (I). In certain embodiments, one or more of the non-coding regions are modified with a functional group or tether which facilitates processing. In certain embodiments, one or more of the non-coding regions are double stranded, which reduces cross-hybridization. In certain embodiments, it is understood that non-coding regions are optional. In certain embodiments, suitable non-coding regions do not interfere with PCR amplification of the oligonucleotide.

In certain embodiments, one or more of the coding regions or terminal coding regions can be a region of the oligonucleotide G that is modified with a label, such as a fluorescent label or a radioactive label. Such labels can facilitate the visualization or quantification of molecules for formula (I). In certain embodiments, one or more of the coding regions or terminal coding regions are modified with a functional group or tether which facilitates processing.

In certain embodiments of the molecule of formula (I), G includes a sequence represented by the formula $(C_N—(Z_N—C_{N+1})_A)$, wherein C is a coding region, Z is a non-coding region, N is an integer from 1 to 20, and A is an integer from 1 to 20. In certain embodiments, from about 70% to 100%, including from about 80% to 99%, including from about 80 to 95%, of the non-coding regions contain from 4 to 50 nucleotides. In certain embodiments, G includes from about 70% to 100%, including from about 80% to 99%, including from about 80% to 95%, of the non-coding regions are double stranded.

In certain embodiments of the molecule of formula (I), the oligonucleotide contains at least one, including from one to two, terminal coding regions. In certain embodiments, a terminal coding region is a sequence of nucleotides that is not directly bound to a hairpin structure and terminates in a 5' end or a 3'end. In certain embodiments, a terminal coding region is a sequence of nucleotides that is directly bound to a hairpin structure. It is understood that the oligonucleotide will have a 5' and 3' direction based on the underlying orientation of the nucleotides, even if both ends of the oligonucleotide are bound by hairpin structures.

In certain embodiments, one purpose of the terminal coding region is to facilitate selective hybridization of a hairpin structure containing a complementary sequence to an end of the oligonucleotide during the synthesis of the molecule of formula (I). In certain embodiments, the terminal coding region contains from about 6 to about 50 nucleotides, including from about 12 to about 40 nucleotides, and including from about 8 to about 30 nucleotides. In certain embodiments, if the terminal coding region contains less than about 6 nucleotides, then the number of available, non-cross-reactive sequences would be too low, which would interfere with accurate encoding of the encoded portion of the molecule of formula (I). In certain embodiments, if the terminal coding region contains more than about 50 nucleotides then the terminal coding region could become cross reactive and lose too much specificity to selectively hybridize to only one hairpin structure. Such cross reactivity would interfere with the ability of the coding regions to accurately code for the addition of the first building block D and/or the second building block E. In certain embodiments of the molecule of formula (I), the terminal coding region is single or double stranded.

In certain embodiments of the molecule of formula (I), $H_1$ and $H_2$ are each independently hairpin structures. The term "hairpin structure" as used in the present disclosure refers to a molecular structure that contains from 60% to 100% nucleotides by mass percent, and can hybridize to a terminal coding region of the oligonucleotide G. In certain embodiments of the hairpin structure, the hairpin structure forms a single, continuous polymer chain, and contains at least one overlapping portion (commonly called a "stem"), wherein the overlapping portion contains a sequence of nucleotides that is hybridized to a complementary sequence of the same hairpin structure. In certain embodiments of the hairpin structure, a bridge structure connects two separate oligonucleotide strands; said bridge structure may be comprised of a polyethylene glycol (PEG) polymer of between 2 and 20 PEG units, including between 3 and 15 PEG units, including between 6 and 12 PEG units. In certain embodiments of the hairpin structure, the bridge structure may be comprised of an alkane chain of up to 30 carbons, or a polyglycine chain of up to 20 units, or comprised of some other chain that bears a reactive functional group. In certain embodiments of the molecule of formula (I), an overlapping portion of $H_1$ and/or $H_2$ is bound or attached to a terminal coding region of the oligonucleotide G. In certain embodiments, $H_1$ and $H_2$ each independently contain one, two, three, or four loops.

In certain embodiments of the molecule of formula (I), $H_1$ and $H_2$ each independently include from about 20 to about 90 nucleotides, including from about 32 to about 80 nucleotides, including from about 45 to about 80 nucleotides. In certain embodiments, $H_1$ and $H_2$ each independently contains 1, 2, 3, 4, 5, 6, 7, 8, 9, or 10, including from 1 to 5, including from 2 to 4, including from 2 to 3, nucleotides modified with suitable functional groups for facilitating reaction with a linker molecule, or optionally with a building block, including cases where $H_1$ and $H_2$ each independently have been synthesized using bases like, but not limited to, 5'-Dimethoxytrityl-5-ethynyl-2'-deoxyUridine, 3'-[(2-cyanoethyl)-(N,N-diisopropyl)]-phosphoramidite (also called 5-Ethynyl-dU-CE Phosphoramidite, purchased form Glen Research, Sterling VA). In certain embodiments, $H_1$ and $H_2$ each independently include non-nucleotides that have suitable functional groups for facilitating reaction with a linker molecule, or optionally with a building block, including but not limited to 3-Dimethoxytrityloxy-2-(3-(5-hexynamido) propanamido)propyl-1-O-[(2-cyanoethyl)-(N,N-diisopropyl)]-phosphoramidite (also called Alkyne-Modifier Serinol Phosphoramidite, from Glen Research, Sterling VA), and abasic-alkyne CEP (from IBA GmbH, Goettingen, Germany). In certain embodiments, $H_1$ and $H_2$ each independently include nucleotides with modified bases already bearing a linker, for example $H_1$ and $H_2$ each independently could be synthesized using bases like, but not limited to, 5'-Dimethoxytrityl-N6-benzoyl-N8-[6-(trifluoroacetylamino)-hex-1-yl]-8-amino-2'-deoxyAdenosine-3'-[(2-cyanoethyl)-(N,N-diisopropyl)]-phosphoramidite (also called amino-modifier C6 dA, purchased from Glen Research, Sterling VA), 5'-Dimethoxytrityl-N2-[6-(trifluoroacetylamino)-hex-1-yl]-2'-deoGuanosine-3'-[(2-cyanoethyl)-(N, N-diisopropyl)]-phosphoramidite (also called amino-modifier C6 dG, purchased from Glen Research, Sterling, VA), 5'-Dimethoxytrityl-5-[3-methyl-acrylate]-2'-deoxyUridine, 3'-[(2-cyanoethyl)-(N,N-diisopropyl)]-phosphoramidite (also called Carboxy dT, purchased from Glen Research, Sterling VA), 5'-Dimethoxytrityl-5-[N-((9-fluorenyl-methoxycarbonyl)-aminohexyl)-3-acrylimido]-2'-deoxyUridine, 3'-[(2-cyanoethyl)-(N,N-diisopropyl)]-phosphoramidite (also called Fmoc-amino modifier C6 dT, Glen Research, Sterling, VA), 5'-Dimethoxytrityl-5-(octa-1,7-diynyl)-2'-deoxyuridine, 3'-[(2-cyanoethyl)-(N,N-diisopropyl)]-phosphoramidite (also called CI alkyne dT, Glen Research, Sterling VA), 5'-(4,4'-Dimethoxytrityl)-5-[N-(6-(3-benzoylthiopropanoyl)-aminohexyl)-3-acrylamido]-2'deoxyuridine, 3'-[(2-cyanoethyl)-(N,N-diisopropyl)]-phosphoramidite (also called S-Bz-Thiol-Modifier C6-dT, Glen Research, Sterling VA), and 5-carboxy dC CEP (from IBA GmbH, Goettingen, Germany), N4-TriGl-Amino 2'deoxycytidine (from IBA GmbH, Goettingen, Germany). Suitable functional groups for modified nucleotides and non-nucleotides in $H_1$ and $H_2$ include but are not limited to a primary amine, a secondary amine, a carboxylic acid, a primary alcohol, an ester, a thiol, an isocyanate, a chloroformate, a sulfonyl chloride, a thionocarbonate, a heteroaryl halide, an aldehyde, a chloroacetate, an aryl halide, a halide, a boronic acid, an alkyne, an azide, and an alkene.

In certain embodiments, one or more of the hairpin structures $H_1$ and $H_2$ can be modified with a label, such as a fluorescent label or a radioactive label. Such labels can facilitate the visualization or quantification of molecules for formula (I). In certain embodiments, one or more of the hairpin structures $H_1$ and $H_2$ are modified with a functional group or tether which facilitates processing.

In certain embodiments of the molecule of formula (I), a benefit of the hairpin structure of $H_1$ and $H_2$ is that one or both can allow for the polydisplay of multiple encoded portions at one or both ends of the molecule of formula (I). Without wishing to be bound by theory, it is believed that the polydisplay of multiple encoded portions at one or both ends of a multifunctional molecule of the present disclosures provides improved selection characteristics under certain conditions.

In certain embodiments of the molecule of formula (I), Y and W are each independently 1, 2, 3, 4, or 5. In certain embodiments, if O is zero, then W is an integer from 2-5, including 2, 3, 4, or 5. In certain embodiments, if P is zero, then Y is an integer from 2-5, including 2, 3, 4, or 5. In certain embodiments, if O and P are each 1, then W and Y are each independently an integer from 1-5, including 1, 2, 3, 4, or 5. In certain embodiments, W and Y are each independently a measure or indicator of the polydisplay of the encoded portion of the molecule of formula (I), wherein the encoded portions is understood to be the unit $(B_1)_M$-D and E-$(B_2)_K$. In general, the higher the aggregate value of Y and W, the higher the polydisplay of the molecule of formula (I).

In certain embodiments of the molecule of formula (I), D is a first building block. In certain embodiments, when D is present, D is coded for or selected by a terminal coding region of G that is directly attached to $H_1$. In certain embodiments, the terminal coding region of G located closest to D corresponds to and can be used to identify the first building block D.

In certain embodiments of the molecule of formula (I), E is a second building block. In certain embodiments, when E is present, E is coded for or selected by a terminal coding region of G that is directly attached to $H_2$. In certain embodiments, the terminal coding region of G located closest to E corresponds to and can be used to identify the first building block E. In certain embodiments, the first building block D and the second building block E can be the same or different. It is understood that the first building block and second building block are both building blocks.

In certain embodiments of the molecule for formula (I), B represents a positional building block. The phrase "positional building block" as used in the present disclosure means one unit in a series of individual building block units bound together as subunits forming a larger molecule. In certain embodiments, $(B_1)_M$ and $(B_2)_K$ each independently represents a series of individual building block units bound together to form a polymer chain having M and K number of units, respectively. For example, wherein M is 10, then $(B)_{10}$, refers to a chain of building block units: $B_{10}$-$B_9$—$B_8$-$B_7$-$B_6$—$B_5$-$B_4$—$B_3$-$B_2$—$B_1$. For example, where M is 3 and K is 2, then formula (I) can accurately be represented by the following formula:

$$([((B_1)_3—(B_1)_2—(B_1)_1\text{-}D\text{-}L_1]_Y\text{-}H_1)_O\text{-}G\text{-}(H_2\text{-}[L_2 \quad E\text{-}(B_2)_1—(B_2)_2]_W)_P.$$

It is understood M and K each independently serve as a positional identifier for each individual unit of B.

The precise definition of the term "building block" in the present disclosure depends on its context. A "building block" is a chemical structural unit capable of being chemically linked to other chemical structural units. In certain embodiments, a building block has one, two, or more reactive chemical groups that allow the building block to undergo a chemical reaction that links the building block to other chemical structural units. It is understood that part or all of the reactive chemical group of a building block may be lost when the building block undergoes a reaction to form a chemical linkage. For example, a building block in solution may have two reactive chemical groups. In this example, the building block in solution can be reacted with the reactive chemical group of a building block that is part of a chain of building blocks to increase the length of a chain, or extend a branch from the chain. When a building block is referred to in the context of a solution or as a reactant, then the building block will be understood to contain at least one reactive chemical group, but may contain two or more reactive chemical groups. When a building block is referred to the in the context of a polymer, oligomer, or molecule larger than the building block by itself, then the building block will be understood to have the structure of the building block as a (monomeric) unit of a larger molecule, even though one or more of the chemical reactive groups will have been reacted.

The types of molecule or compound that can be used as a building block are not generally limited, so long as one building block is capable of reacting together with another building block to form a covalent bond. In certain embodiments, a building block has one chemical reactive group to serve as a terminal unit. In certain embodiments, a building block has 1, 2, 3, 4, 5, or 6 suitable reactive chemical groups. In certain embodiments, the first building block D, the second building block E, and the positional building blocks of B each independently have 1, 2, 3, 4, 5, or 6 suitable reactive chemical groups. Suitable reactive chemical groups for building blocks include, a primary amine, a secondary amine, a carboxylic acid, a primary alcohol, an ester, a thiol, an isocyanate, a chloroformate, a sulfonyl chloride, a thionocarbonate, a heteroaryl halide, an aldehyde, a haloacetate, an aryl halide, an azide, a halide, a triflate, a diene, a dienophile, a boronic acid, an alkyne, and an alkene.

Any coupling chemistry can be used to connect building blocks, provided that the coupling chemistry is compatible with the presence of an oligonucleotide. Exemplary coupling chemistry includes, formation of amides by reaction of an amine, such as a DNA-linked amine, with an Fmoc-protected amino acid or other variously substituted carboxylic acids; formation of ureas by reaction of an amine, including a DNA-linked amine, with an isocyanate and another amine (ureation); formation of a carbamate by reaction of amine, including a DNA-linked amine, with a chloroformate (carbamoylation) and an alcohol; formation of a sulfonamide by reaction of an amine, including a DNA-linked amine, with a sulfonyl chloride; formation of a thiourea by reaction of an amine, including a DNA-linked amine, with thionocarbonate and another amine (thioureation); formation of an aniline by reaction of an amine, including a DNA-linked amine, with a heteroaryl halide (SNAr); formation of a secondary amine by reaction of an amine, including a DNA-linked amine, with an aldehyde followed by reduction (reductive amination); formation of a peptoid by acylation of an amine, including a DNA-linked amine, with chloroacetate followed by chloride displacement with another amine (an $SN_2$ reaction); formation of an alkyne containing compound by acylation of an amine, including a DNA-linked amine, with a carboxylic acid substituted with an aryl halide, followed by displacement of the halide by a substituted alkyne (a Sonogashira reaction); formation of a biaryl compound by acylation of an amine, including a DNA-linked amine, with a carboxylic acid substituted with an aryl halide, followed by displacement of the halide by a substituted boronic acid (a Suzuki reaction); formation of a substituted triazine by reaction of an amine, including a DNA-linked amine, with a cyanuric chloride followed by reaction with another amine, a phenol, or a thiol (cyanurylation, Aromatic Substitution); formation of secondary amines by acylation of an amine including a DNA-linked amine, with a carboxylic acid substituted with a suitable leaving group like a halide or triflate, followed by displacement of the leaving group with another amine ($SN_2/SN_1$ reaction); and formation of cyclic compounds by substituting an amine with a compound bearing an alkene or alkyne and reacting the product with an azide, or alkene (Diehls-Alder and Huisgen reactions). In certain embodiments of the reactions, the molecule reacting with the amine group, including a primary amine, a secondary amine, a carboxylic acid, a primary alcohol, an ester, a thiol, an isocyanate, a chloroformate, a sulfonyl chloride, a thionocarbonate, a heteroaryl halide, an aldehyde, a chloroacetate, an aryl halide, an alkene, halides, a boronic acid, an alkyne, and an alkene, has a molecular weight of from about 30 to about 330 Daltons.

In certain embodiments of the coupling reaction, a first building block might be added by substituting an amine, including a DNA-linked amine, using any of the chemistries above with molecules bearing secondary reactive groups like amines, thiols, halides, boronic acids, alkynes, or alkenes. Then the secondary reactive groups can be reacted with building blocks bearing appropriate reactive groups. Exemplary secondary reactive group coupling chemistries include, acylation of the amine, including a DNA-linked amine, with an Fmoc-amino acid followed by removal of the protecting group and reductive amination of the newly deprotected amine with an aldehyde and a borohydride; reductive amination of the amine, including a DNA-linked amine, with an aldehyde and a borohydride followed by reaction of the now-substituted amine with cyanuric chloride, followed by displacement of another chloride from triazine with a thiol, phenol, or another amine; acylation of the amine, including a DNA-linked amine, with a carboxylic acid substituted by a heteroaryl halide followed by an SNAr reaction with another amine or thiol to displace the halide and form an aniline or thioether; and acylation of the amine, including a DNA-linked amine, with a carboxylic acid substituted by a haloaromatic group followed by substitution of the halide by an alkyne in a Sonogashira reaction; or substitution of the halide by an aryl group in a boronic ester-mediated Suzuki reaction.

In certain embodiments, the coupling chemistries are based on suitable bond-forming reactions known in the art. See, for example, March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Coltman et al., Principles and Applications of Organotransition Metal Chemistry, University Science Books, Mill Valley, Calif. (1987), Chapters 13 to 20; each of which is incorporated herein by reference in its entirety.

In certain embodiments, a building block can include one or more functional groups in addition to the reactive group or groups employed to attach a building block. One or more of these additional functional groups can be protected to prevent undesired reactions of these functional groups. Suitable protecting groups are known in the art for a variety of functional groups (Greene and Wuts, Protective Groups in Organic Synthesis, second edition, New York: John Wiley and Sons (1991), incorporated herein by reference in its entirety). Particularly useful protecting groups include t-butyl esters and ethers, acetals, trityl ethers and amines, acetyl esters, trimethylsilyl ethers, trichloroethyl ethers and esters and carbamates.

The type of building block is not generally limited, so long as the building block is compatible with one more reactive groups capable of forming a covalent bond with other building blocks. Suitable building blocks include but are not limited to, a peptide, a saccharide, a glycolipid, a lipid, a proteoglycan, a glycopeptide, a sulfonamide, a nucleoprotein, a urea, a carbamate, a vinylogous polypeptide, an amide, a vinylogous sulfonamide peptide, an ester, a saccharide, a carbonate, a peptidylphosphonate, an azatides, a peptoid (oligo N-substituted glycine), an ether, an ethoxyformacetal oligomer, thioether, an ethylene, an ethylene glycol, disulfide, an arylene sulfide, a nucleotide, a morpholino, an imine, a pyrrolinone, an ethyleneimine, an acetate, a styrene, an acetylene, a vinyl, a phospholipid, a siloxane, an isocyanide, a isocyanate, and a methacrylate. In certain embodiments, the $(B_1)_M$ or $(B_2)_K$ of formula (I) each independently represents a polymer of these building blocks having M or K units, respectively, including a polypeptide, a polysaccharide, a polyglycolipid, a polylipid, a polyproteoglycan, a polyglycopeptide, a polysulfonamide, a polynucleoprotein, a polyurea, a polycarbamate, a polyvinylogous polypeptide, a polyamide, a poly vinylogous sulfonamide peptide, a polyester, a polysaccharide, a polycarbonate, a polypeptidylphosphonate, a polyazatides, a polypeptoid (oligo N-substituted glycine), a polyethers, a polythoxyformacetal oligomer, a polythioether, a polyethylene, a polyethylene glycol, a polydisulfide, a polyatylene sulfide, a polynucleotide, a polymorpholino, a polyimine, a polypyrrolinone, a polyethyleneimine, a polyacetates, a polystyrene, a polyacetylene, a polyvinyl, a polyphospholipids, a polysiloxane, a polyisocyanide, a polyisocyanate, and a polymethacrylate. In certain embodiments of the molecule for formula (I), from about 50 to about 100, including from about 60 to about 95, and including from about 70 to about 90% of the building blocks have a molecular weight of from about 30 to about 500 Daltons, including from about 40 to about 350 Daltons, including from about 50 to about 200 Daltons.

It is understood that building blocks having two reactive groups would form a linear oligomeric or polymeric structure, or a linear non-polymeric molecule, containing each building block as a unit. It is also understood that building blocks having three or more reactive groups could form molecules with branches at each building block having three or more reactive groups.

In certain embodiments of the molecule for formula (I), $L_1$ and $L_2$ each independently represent a linker. The term "linker molecule" refers to a molecule having two or more reactive groups that is capable of reacting to form a linker. The term "linker" refers to a portion of a molecule that operatively links or covalently bonds a hairpin structure to a building block. The term "operatively linked" means that two or more chemical structures are attached or covalently bonded together in such a way as to remain attached throughout the various manipulations the multifunctional molecules are expected to undergo, including PCR amplification.

In certain embodiments of the molecule for formula (I), $L_1$ is a linker that operatively links $H_1$ to D. In certain embodiments of the molecule for formula (I), $L_2$ is a linker that operatively links $H_2$ to E. In certain embodiments, $L_1$ and $L_2$ are each independently bifunctional molecules linking $H_1$ to D by reacting one of the reactive functional groups of $L_1$ to a reactive group of $H_1$ and the other reactive functional group of $L_1$ to a reactive functional group of D, and linking $H_2$ to E by reacting one of the reactive functional groups of $L_2$ to a reactive group of $H_2$ and the other reactive functional group of $L_2$ to a reactive functional group of E. In certain embodiments of the molecule for formula (I), $L_1$ and $L_2$ are each independently linkers formed from reacting the chemical reactive groups of $H_1$ and D or $H_2$ and E with commercially available linker molecules including, PEG (e.g., azido-PEG-NHS, or azido-PEG-amine, or di-azido-PEG), or an alkane acid chain moiety (e.g., 5-azidopentanoic acid, (S)-2-(azidomethyl)-1-Boc-pyrrolidine, 4-azidoaniline, or 4-azido-butan-1-oic acid N-hydroxysuccinimide ester); thiol-reactive linkers, such as those being PEG (e.g., SM(PEG)n NHS-PEG-maleimide), alkane chains (e.g., 3-(pyridin-2-yldisulfanyl)-propionic acid-Osu or sulfosuccinimidyl 6-(3'-[2-pyridyldithio]-propionamido)hexanoate)); and amidites for oligonucleotide synthesis, such as amino modifiers (e.g., 6-(trifluoroacetylamino)-hexyl-(2-cyanoethyl)-(N,N-diisopropyl)-phosphoramidite), thiol modifiers (e.g., 5-trityl-6-mercaptohexyl-1-[(2-cyanoethyl)-(N,N-diisopropyl)]-phosphoramidite, or chemically co-reactive pair modifiers (e.g., 6-hexon-1-yl-(2-cyanoethyl)-(N,N-diisopropyl)-phosphoramidite, 3-dimethoxytrityloxy-2-(3-(3-propargyloxypropanamido)propanamido)propyl-1-O-succinoyl, long chain alkylamino CPG, or 4-azido-butan-1-oic acid N-hydroxysuccinimide ester)); and compatible combinations thereof.

In certain embodiments, the multifunctional molecule is a molecule of formula (I-A), which is a subspecies of the molecule of formula (I):

$$[(B_1)_M\text{-}D\text{-}L_1]_Y\text{-}H_1\text{-}G, \qquad \text{(I-A)}$$

wherein G, $H_1$, D, $B_1$, M, $L_1$, and Y, are as defined above for formula (I). In certain embodiments, the multifunctional molecule is a molecule of formula (I-B), which is a subspecies of the molecule of formula (I):

$$[(B_1)_M\text{-}D\text{-}L_1]_Y\text{-}H_1\text{-}G\text{-}H_2, \qquad \text{(I-B)}$$

wherein G, $H_1$, $H_2$, D, $B_1$, M, $L_1$, and Y are as defined above for formula (I). In certain embodiments, the multifunctional molecule is a molecule of formula (I-C), which is a subspecies of the molecule of formula (I):

$$[(B_1)_M\text{-}D\text{-}L_1]_Y\text{-}H_1\text{-}G\text{-}H_2\text{-}[L_2]_W, \qquad \text{(I-C)}$$

wherein G, $H_1$, $H_2$, D, $B_1$, M, $L_1$, $L_2$. W, and Y are as defined above for formula (I). In certain embodiments, the multifunctional molecule is a molecule of formula (I-D), which is a subspecies of the molecule of formula (I):

$$[(B_1)_M\text{-}D\text{-}L_1]_Y\text{-}H_1\text{-}G\text{-}H_2\text{-}[L_2\text{-}E]_W, \qquad \text{(I-D)}$$

wherein G, $H_1$, $H_2$, D, $B_1$, E, M, $L_1$, $L_2$, W and Y are as defined above for formula (I). In certain embodiments, the multifunctional molecule is a molecule of formula (I-E), which is a subspecies of the molecule of formula (I):

$$G\text{-}H_2\text{-}[L_2\text{-}E\text{-}(B_2)_K]_W, \qquad \text{(I-E)}$$

wherein G, $H_2$, E, $B_2$, K, $L_2$, and W are as defined above for formula (I). In certain embodiments, the multifunctional molecule is a molecule of formula (I-F), which is a subspecies of the molecule of formula (I):

$$H_1\text{-}G\text{-}H_2\text{-}[L_2\text{-}E\text{-}(B_2)_K]_W \qquad \text{(I-F)}$$

G, $H_1$, $H_2$, E, $B_2$, K, $L_2$, P, and W are as defined above for formula (I). In certain embodiments, the multifunctional molecule is a molecule of formula (I-G), which is a subspecies of the molecule of formula (I):

$$[L_1]_Y\text{-}H_1\text{-}G\text{-}H_2\text{-}[L_2\text{-}E\text{-}(B_2)_K]_W, \qquad \text{(I-G)}$$

wherein G, $H_1$, $H_2$, E, $B_2$, K, $L_1$, $L_2$, Y, and W are as defined above for formula (I). In certain embodiments, the multifunctional molecule is a molecule of formula (I-H), which is a subspecies of the molecule of formula (I):

$$[D\text{-}L_1]_Y\text{-}H_1\text{-}G\text{-}H_2\text{-}[L_2\text{-}E\text{-}(B_2)_K]_W, \qquad \text{(I-H)}$$

wherein G, $H_1$, $H_2$, D, E, B, M, $L_1$, $L_2$, P, Y, and W are as defined above for formula (I).

The present disclosure relates to methods of synthesizing multifunctional molecules, including the molecule of formula (I). In certain embodiments of the method, the at least one terminal coding region on an oligonucleotide, such as G', is capable of hybridizing with at least one charged carrier anti-codon, including:

$$[(B_1)_{(M-1)}\text{-}D\text{-}L_1]_Y\text{-}H_1 \text{ and/or } H_2\text{-}[L_2\text{-}E\text{-}(B_2)_{(K-1)}]_W,$$

to form a molecule of formula (II):

$$([(B_1)_{(M-1)}\text{-}D\text{-}L_1]_Y\text{-}H_1)_O\text{-}G\text{-}(H_2\text{-}[L_2\text{-}E\text{-}(B_2)_{(K-1)}]_W)_P, \quad \text{(II)}$$

wherein $B_1$, M, D, $L_1$, Y, $H_1$, O, $H_2$, $L_2$, E, $B_2$, K, W, and P are as defined above for formula (I), and G' is or contains an oligonucleotide comprising at least two coding regions and at least one terminal coding region, wherein the at least two coding regions are single stranded, the at least one terminal coding region is single stranded, and the at least one terminal coding region at a 5' and/or a 3' end of the oligonucleotides G' is different.

It is understood that $[(B_1)_{(M-1)}\text{-}D\text{-}L_1]_Y\text{-}H_1$ is $(D\text{-}L_1)_Y\text{-}H_1$, where M is one. It is understood that $H_2\text{-}[L_2\text{-}E\text{-}(B_2)_{(K-1)}]_W$ is $H_2\text{-}(L_2\text{-}E)_W$, where K is one.

As depicted in FIGS. 1 and 3, in certain embodiments, a benefit of this method of forming a molecule of formula (II) is that the terminal coding region of G' can encode or direct the addition of a first part of the encoded portion of the molecule, including the first building block D and/or the second building block E. For example, each terminal coding region in the molecule of formula (I) would uniquely identify a first building block D and/or a second building block E, because the identity of the first building block D and/or the second building block E of the charged carrier anti-codon capable of selectively hybridizing to the terminal coding region would be known.

Figure 2:
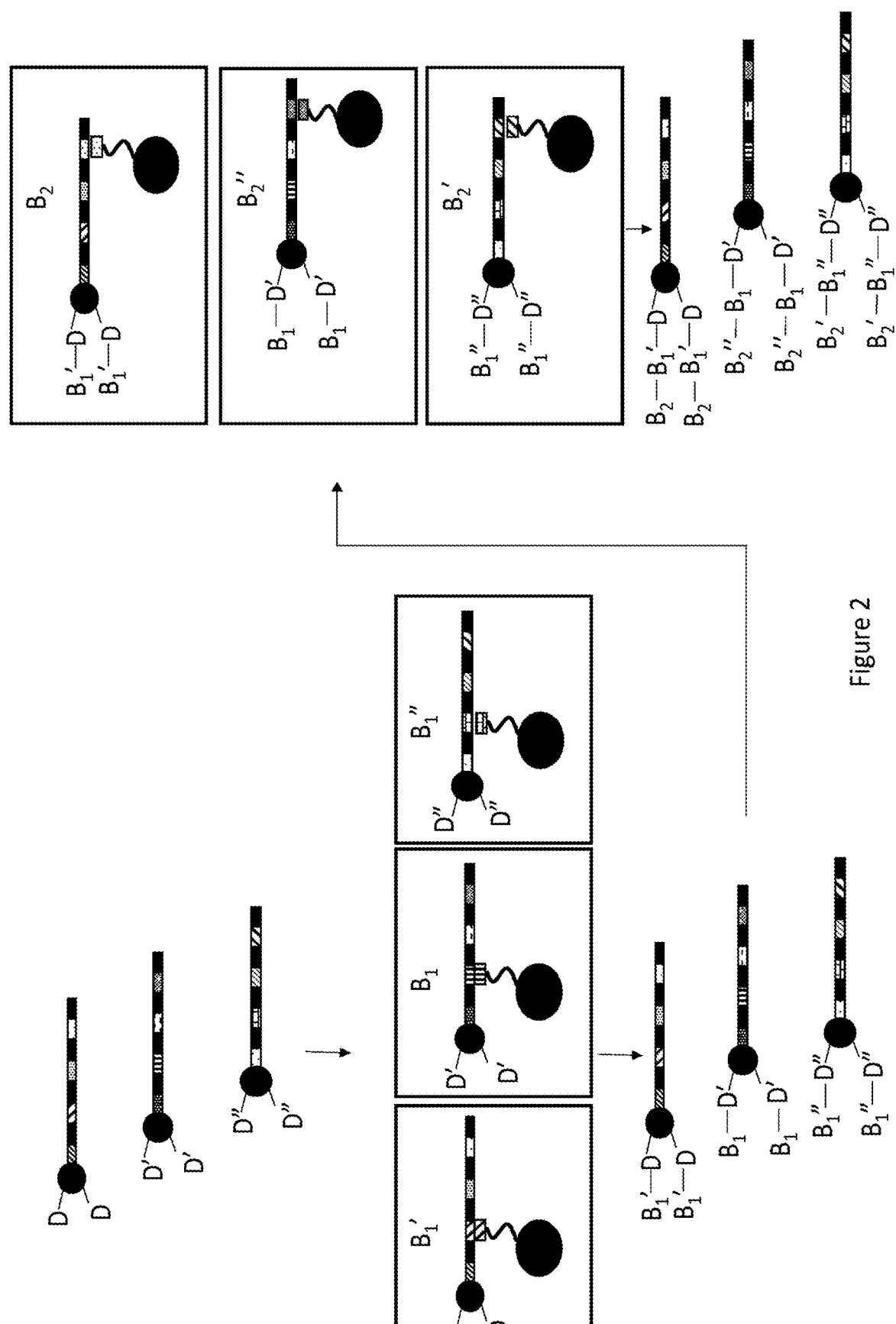
FIG. 2 is an illustration of an embodiment of a method of preparing a plurality of multifunctional molecules.

As depicted in FIG. 2, in certain embodiments of a method of synthesizing a molecule of formula (I), the method uses a series of "sort and react" steps, where a mixture of multifunctional molecules containing different combinations of encoding regions are sorted into sub-pools by selective hybridization of one or more coding regions of the multifunctional molecule with an anti-coding oligomer immobilized on a hybridization array. In certain embodiments of the method, a benefit to sorting the multifunctional molecules into sub-pools is that this separation allows for each sub-pool to be reacted with a positional building block B, including $B_1$ and/or $B_2$, under separate reaction conditions before the sub-pools of multifunctional molecules are combined or mixed for further chemical processing. In certain embodiments of the method, the sort and react process can be repeated to add a series of positional building blocks. In certain embodiments of the method, a benefit of adding building blocks using a sort and react method is that the identity of each positional building block of the encoded portion of the molecule can be correlated to the coding region that is used to selectively separate or sort the multifunctional molecule prior to the addition of a building block. In certain embodiments, each coding region uniquely identifies a building block according to its position, because the identity of the coding region can be correlated to the identity of the reaction process used to add each building block, which would include the identity of the positional building block added. In certain embodiments, the method can synthesize a multifunctional molecule, including a molecule of formula (I), wherein at least one of at least one of the first building block D and second building block E is identified by or corresponds to the at least one terminal coding region, and at least one of each positional building block $B_1$ at position M and $B_2$ at position K is identified by or corresponds to one of the coding regions. It is understood that the molecules of formulas (I) and (II) can include one or more coding regions and terminal coding regions that are identical between or among molecules in a pool, but it is also understood that the vast majority, if not all, of the molecules in the pool would have a different combination of coding regions and terminal coding regions. In certain embodiments of the method, a benefit of a pool of molecules having a different combination of coding region and terminal coding regions is that the different combinations can encode for multifunctional molecules having a multitude of different encoded portions.

In certain embodiments of a method of synthesizing a molecule of formula (I), the method includes a step of providing at least one charged carrier anti-codon, wherein the at least one charged carrier anti-codon has the formula of:

$$([(B_1)_{(M-1)}\text{-}D\text{-}L_1]_Y\text{-}H_1) \text{ and/or } (H_2\text{-}[L_2\text{-}E\text{-}(B_2)_{(K-1)}]_W),$$

wherein $B_1$, M, D, $L_1$, Y, $H_1$, $H_2$, $L_2$, E, $B_2$, K, and W are as defined for the molecule of formula (I). The term "providing" is not generally limited, and can include synthesizing or commercially purchasing such molecules. The term "charged carrier anti-codon" refers to a hairpin structure that is operatively linked to a first building block or a second building block by a linker and has an oligonucleotide anti-coding region that is capable of selectively binding with the at least one terminal coding region of the oligonucleotide G' or G. In certain embodiments of the method, a purpose of the charged carrier anti-codon is to allow the terminal coding region to code for, direct, or select for the addition of the first building block and/or the second building block. In certain embodiments of the method, a purpose of the charged carrier anti-codon is to bind or attach a building block, including a first or second building block, onto at least one end of the oligonucleotide G' to form a molecule of formula (II), which will allow for the oligonucleotide G to encode for or direct the synthesis of positional building blocks $B_1$ and/or $B_2$.

In certain embodiments of a method of synthesizing a molecule of formula (I), the combining step is not generally limited so long as the pool of oligonucleotides G' and the at least one charged carrier anti-codon are allowed to interact or mix under conditions that will allow for selective hybridization.

In certain embodiments of a method of synthesizing a molecule of formula (I), the step of bonding the 5' end of the at least one oligonucleotides G' to the 3' end of $H_1$ includes selectively hybridizing the terminal coding region at the 5' end of G' to anti-codon of $H_1$. In certain embodiments of a method of synthesizing a molecule of formula (I), the step of bonding the 3' end of the at least one oligonucleotide G' to the 5' end of $H_2$ includes selectively hybridizing the terminal coding region at the 3' end of G' to anti-codon of $H_2$.

In certain embodiments of a method of synthesizing a molecule of formula (I), the method includes ligating the 5' end of the at least one oligonucleotide G to the 3' end of $H_1$ to form a covalent bond, and/or ligating the 3' end of at least one oligonucleotide G to the 5' end of $H_2$ This ligation step can occur during or after the formation of the molecule of formula (II). In certain embodiments of the method, a benefit of forming a covalent bond during or after the bonding step includes improved handling during other chemical processing steps.

In certain embodiments of a method of synthesizing a molecule of formula (I), the method can further include a step of removing all of part of an oligonucleotide from the at least one terminal coding region of a molecule of formula (I) or (II) during or after the formation of a molecule of formula (II). In certain embodiments of a method of synthesizing a molecule of formula (I), the method can further include a step of removing all of part of an oligonucleotide from the at least one terminal coding region of a molecule of formula (I) or (II), wherein the at least one terminal coding region is double stranded and the oligonucleotide can be removed from either the hairpin structure of $H_1$ and/or $H_2$, including from the anti-codon of the hairpin structure of $H_1$ and/or $H_2$, or from the terminal coding region of G or G'. In one certain embodiments, a benefit of removing all or part of an oligonucleotide from the at least one terminal coding region of a molecule of formula (I) or (II) can include improve chemical handling during later steps.

As schematically depicted in FIGS. 3 and 4, in certain embodiments of the method for forming the molecule of formula (I), the molecule of formula (I) can be synthesized by multiple synthetic routes by varying the order of the processing steps. For example, in FIG. 3, two charged carrier anti-codons can be added during the same step. Then, subsequent sort and react steps can be performed to add building blocks $B_1$ and $B_2$ under the same reaction conditions. In this embodiment, the encoded regions of $(B_1)_M$ and $(B_2)_K$, would likely be identical, where $B_1=B_2$ and $M=K$.

Alternatively, in FIG. 4, one charged carrier anti-codon, $([(B_1)_{(M-1)}\text{-D-L}_1]_Y\text{-H}_1)$, can be combined and bonded with G" to form a molecule of formula (I), where P is zero. Then, subsequent sort and react steps can be performed to add building blocks $B_1$. Once the formation of the encoded portion of $(B_1)_M$ is complete, then a second charged carrier anti-codon, $(H_2\text{-[L}_2\text{-E-(B}_2)_{(K-1)}]_W)$ can be combined and bonded with G to form a different molecule of formula (I), wherein P is 1. Then, subsequent sort and react steps can be performed to add building blocks $B_2$, using the same or different positional building blocks and reaction conditions. In certain embodiments, $(B_1)_M$ and $(B_2)_K$ are different because the type and order of the reaction used to select and sort the pool of molecules of formula (II) and (I), respectively, were different. It is understood that in certain embodiments, the charged carrier anti-codon $(H_2\text{-[L}_2\text{-E-}(B_2)_{(K-1)}]_W)$ can be added first to form $(B_2)_K$ before the addition of $([(B_1)_{(M-1)}\text{-D-L}_1]_Y\text{-H}_1)$ to form $(B_1)_M$.

It is also understood that the addition of the later added charged carrier anti-codon does not need to be added after the complete formation or encoding of $(B_1)_M$ or $(B_2)_K$. Instead, the later addition of the charged carrier anticodon could take place after at least one of $B_1$ or $B_2$ was added to the previously added charged carrier anti-codon. After the addition of the second charged carrier anti-codon, the subsequent sort and react steps can be performed to add building blocks $B_1$ and $B_2$ to form $(B_1)_M$ or $(B_2)_K$. In these embodiments, the at least part of the first encoded portion would match the later added encoded portion, but the two encoded portions $(B_1)_M$ or $(B_2)_K$ would differ by at least the positional building blocks added before bonding the later added charged carrier anti-codon.

In certain embodiments, the method of forming a molecule of formula (I) includes reacting a molecule of formula (II):

$$([(B_1)_{(M-1)}\text{-D-L}_1]_Y\text{-H}_1)_O\text{-G-(H}_2\text{-[L}_2\text{-E-(B}_2)_{(K-1)}]_W)_P, \tag{II}$$

with one or more of a positional building block $B_1$ and/or $B_2$ to form a molecule of formula (I):

$$([(B_1)_M\text{-D-L}_1]_Y\text{—H}_1)_O\text{-G-(H}_2\text{-[L}_2\text{-E-(B}_2)_K]_W)_P, \tag{I}$$

wherein $H_1$, $H_2$, D, E, $B_1$, M, $B_2$, K, $L_1$, $L_2$, O, P, Y, and W are as defined for formula (I).

In certain embodiments, the method includes providing at least one hybridization array. The step of providing a hybridization array is not generally limited, and includes manufacturing the hybridization array using techniques known in the art or commercially purchasing the hybridization array. In certain embodiments of the method, a hybridization array includes a substrate of at least two separate areas having immobilized anti-codon oligomers on their surface. In certain embodiments, each area of the hybridization array contains a different immobilized anti-codon oligomer, wherein the anti-codon oligomer is an oligonucleotide sequence that is capable of hybridizing with one or more coding regions of a molecule of formulas (I) or (II). In certain embodiments of the method, the hybridization array uses two or more chambers. In certain embodiments of the method, the chambers of the hybridization array contain particles, such as beads, that have immobilized anti-codon oligomers on the surface of the particles. In certain embodiments of the method, a benefit of immobilizing a molecule of formula (I) or (II) on the array, is that this step allows the molecules to be sorted or selectively separated into sub-pools of molecules on the basis of the particular oligonucleotide sequence of each coding region. In certain embodiments, the separated sub-pools of molecules can then be separately released or removed from the array into reaction chambers for further chemical processing. In certain embodiments, the step of releasing is optional, not generally limited, and can include dehybridizing the molecules by heating, using denaturing agents, or exposing the molecules to buffer of pH≥12. In certain embodiments, the chambers or areas of the array containing different immobilized oligonucleotides can be positioned to allow the contents of each chamber or area to flow into an array of wells for further chemical processing.

In certain embodiments, the method includes reacting the at least one building block B, including $B_1$ and/or $B_2$, with a molecule of formula (II) to form a molecule of a sub-pool of molecules of formula (I) or (II), wherein $B_1$ and/or $B_2$ is as defined above for formula (I). In certain embodiments, the building block $B_1$ and/or $B_2$ can be added to the container before, during, or after the molecule of formula (I) or (H). It is understood that the container can contain solvents, and co-reactants under acidic, basic, or neutral conditions, depending on the coupling chemistry that is used to react the building block $B_1$ and/or $B_2$ with a molecule of formula (II) or (I).

A method of identifying probe molecules capable of binding or selecting for a target molecule is disclosed. In certain embodiments, the method includes exposing a target molecule to a pool of multifunctional molecules, such as a molecule of formula (I), to determine if one of the multifunctional molecules is capable of binding the target molecule. In certain embodiments, the term "exposing" includes any manner of bringing the target molecule into contact with a probe molecule, including a molecule of formula (I). In certain embodiments, the probe molecules that do not bind the target molecule are removed by a removal method, including washing the unbound probe molecules away from the target molecule using excess solvent. In certain embodiments, the target molecule is immobilized on a surface. In certain embodiments, the target molecule includes proteins, enzymes, lipids, oligosaccharides, and nucleic acids with tertiary structures.

In certain embodiments of the method, the amplifying step includes using PCR techniques known in the art to create a copy sequence of the oligonucleotide G of formula (I). In certain embodiments of the method, the copy sequence contains a copy of the at least two coding regions of formula (I) and the at least one terminal coding region of (I). In certain embodiments, one benefit of amplifying the oligonucleotide G from the at least one probe molecule includes the ability to detect which encoded portions of a multifunctional molecule are capable of binding a target molecule, even though the multifunctional molecule cannot easily be removed from the target molecule. In certain embodiments, a benefit of amplification is that it allows for libraries of molecules with vast diversity to be generated. This vast diversity comes at the cost of low numbers of any given molecule of formula (I). Amplifying by PCR allows identification of oligonucleotide sequences present in very small numbers by increasing those numbers until an easily detectable number is reached. Then, DNA sequencing and analysis of the copy sequence can identify or be correlated to the encoded portion of the multifunctional molecule of formula (I) that was capable of binding the target.

More Detail Regarding the Challenges

The high cost of drug discovery and the increasing need to discover molecules with unique and desirable properties for use in medicine, research, biotechnology, agriculture, food production, and industry has given rise to the field of combinatorial chemistry.

Discovery of a molecule with highly desirable properties for a particular desired application may not always be straightforward. For instance, molecules that bind a target protein or biological macromolecule or polymolecular structure can be profoundly difficult to rationally design. When faced with the challenge of discovering a molecule for which structural designs ascertained from first principles are impossible or inefficient, combinatorial chemistry has presented itself as a viable tool. Combinatorial chemistry enables discovery through the following general process: (a) the researcher makes the best hypotheses available about the more general properties and structure a molecule may have in order to fit the criteria for the desired application, (b) the researcher designs and synthesizes a very large number of molecules, termed a library, possessing the general properties or structures hypothesized, (c) the library is tested to determine if any of the library members possess the characteristics for the desired application.

Where information is limited, those hypotheses that can be made about the structure of a desirable molecule will be looser and less well-defined, than in cases where there is a large body of knowledge to inform those hypotheses. Where more data informs structural hypotheses, libraries with smaller complexity or diversity, e.g., $1e^4$-$1e^7$ unique members, focuses tightly on regions of chemical shape space hypothesized to be rich in desirable structures may be more successful. In cases where little or no data exists, libraries with far larger complexity and which sample greater regions of shape space and sample it more deeply, e.g., $1e^5$-$1e^{14}$ unique members, may be required for success.

Combinatorial chemistry allows the synthesis of libraries of compounds on this scale by split-and-pool or sort and react chemical synthesis methods. Typical split-and-pool libraries start with a functional group that is incorporated in the chain of a polymeric solid support like a polystyrene bead. A group of several thousand to several million beads are split into a series of vessels and the beads in each vessel are reacted with a different chemical subunit or building block. When the reaction is complete, all the beads are pooled, mixed well, and re-split into a new series of reaction vessels for a second step of chemical synthesis with the same or a different set of building blocks. The split-and-pool reaction process is repeated until synthesis is complete. The number of compounds made by this method is only limited by the number of beads that can be handled in the process, and the number of building blocks used at each step. These two parameters will define the complexity of such a library. For example if there are 5 chemical subunits at each of 4 steps, the $5^4$=625 members will make up the library. Similarly, if there are 52 building blocks at the first step, 3 at the second, 384 at the third, and 96 at the fourth, then $52 \times 5 \times 384 \times 96$=3,833,856 library members will have been produced.

The library of molecules can then be tested to ascertain which of them possesses the desired characteristics for the chosen application. Identification of such molecules can be challenging because the amount of molecules produced on a single bead can be quite small and therefore hard to identify. It is generally understood in the combinatorial chemistry community that for libraries tailored appropriately to the amount of structural data available to guide the design of the library, that larger libraries are expected to meet with a greater probability of possessing highly desirable members. However, for any given amount of library produced, the greater the complexity, or the greater the number of unique molecules in the library, the lower the copy number, or the number of copies of each member there will be. Therefore, as a library increases in complexity and in the probability of having a successful member, the total amount of that successful member diminishes along with the ability of the combinatorial chemist to correctly identify it.

The constrained optimization the combinatorial chemist then faces is to make a library with sufficient complexity to possess desirable members, while also making enough copies of each member of the library to ensure the desirable members are accurately identified. In general, as the complexity of a library increases, the size of the solid support must also decrease; as that support size decreases, so does the amount of sample available for analysis and identification.

In general, given sufficient resources one could synthesize a very large combinatorial library of $10^{10}$ unique members on polystyrene beads in a one-bead-one-compound library. But if each polystyrene bead were a sphere of volume 0.1 microliters, then the volume of the $10^{10}$-member library would be >1 cubic meter—enough to fill an ordinary hot tub or spa, perhaps to overflowing. And while industrial chemical processes are often carried out on this scale, processes of this complexity are very rarely carried out on this scale. A library on this scale also brings up the question of testing such a library, and producing the molecular target for those tests. Such a test could easily require a kilogram of purified protein and the cost of producing that much drug target protein would be astronomical for many drug target proteins.

DNA-encoded combinatorial chemistry libraries seek to improve this situation. The fact that PCR can vastly amplify a single template strand of DNA with great accuracy, and the fact that amplified strands can be sequenced readily, enables the possibility of reducing the size of the solid support down to a single molecule of DNA. Thus, the ability to both make extremely vast libraries (e.g., $10^6$-$10^{14}$ unique members), and also identify successful molecules from that population could be achieved by tethering a combinatorial chemistry library member to a strand of DNA in a way that establishes a correspondence between the DNA sequence and the identity of the library member. A selection experiment is then performed. A "selection" being an experiment physically isolating those members of the library population possessing desired traits from those members that do not. DNA encoding trait-positive library members is then amplified by PCR, and sequencing of the DNA identifies the trait-positive library member. In this manner libraries of vast complexity can be synthesized, and trait-positive individuals identified from vanishingly small sample sizes.

New DNA sequencing technologies capable of returning $10^6$-$10^8$ unique sequences facilitates markedly improved analysis of DNA-encoded libraries. "Deep sequencing" data enables robust statistical analysis of very complex chemical libraries. These kinds of analysis not only identify specific individual members of the library appropriate for the chosen application, but can also reveal previously unknown general traits that confer 'fitness' for the application on library members. Typically, a DNA library is deep sequenced prior to a selection experiment designed to physically separate individuals that are more fit for the application at hand from individuals that are less fit. The population after the experiment is deep sequenced and comparison of the two data sets shows which individuals are more fit because their relative frequency in the population increases. Those individuals that are less fit will be identified because their relative frequency in the population diminishes. However, DNA-encoded combinatorial chemistry methods can make libraries with complexities that far outstrip the most powerful current deep sequencing technologies. Although deep sequencing enables a vast improvement in the utility and success of DNA-encoded combinatorial libraries, it still only provides a statistical under-sampling of the data that is theoretically available.

The problem of this data under-sampling is compounded by the fact that not every step in the combinatorial chemistry process proceeds with perfect efficiency. A loss of fidelity is observed because some reactions do not go to completion, and some reactions form by-products. Therefore, there is not always perfect clarity that the DNA sequence returned by deep sequencing represents the actual molecule it encoded, but may on occasion represent a truncation product or a product altered by side reactions.

Compounding the problem of under sampling is the problem of synthetic fidelity. Not every reaction used in making a combinatorial library will be perfectly efficient. This means that some DNAs in a DNA encoded library are not tethered to the molecule they encode, but are rather tethered to truncation products resulting from incomplete incorporation of one or more building blocks, or they are tethered to analogous compounds resulting from the incorporation of a by-product or side reaction. Data analysis thus suffers because some of the genotypes observed to be surviving selection represent molecules other than the ones they encode.

Directed Evolution

An object of the present disclosure is to identify molecules fit for desired applications through the production of DNA-encoded libraries with vast complexity and high fidelity, to maximize current sequencing technologies, and to overcome under-sampling problems through multi-generational selections. Another object of the present disclosure is to enable more accurate synthesis by allowing a first step of the synthesis of a library to be purified.

Generally, the method of the present disclosure works as follows. A population of molecules is encoded in a pool of DNA genes (oligonucleotides G or G'). The DNA sequences (oligonucelotides G or a copy thereof) then template the synthesis, or translation, of the small molecule library members (the encoded portions), establishing a covalent tether (linker) between the DNA genotypes and their corresponding small molecule phenotypes. The population of genotype-phenotype fusions (a library of molecules of formula (I)) can then be subjected to a selection pressure, and the DNA (at least two coding regions and at least two terminal coding regions) of those individuals surviving selection is amplified by PCR. This second generation population of survivors (copy sequence) can be (a) subjected to deep sequencing and analysis to identify fit individuals (encoded portions with desirable properties), and/or (b) the population is re-translated, subjected to a second round of more stringent selection for the same property, or for a different property. Survivors of the second generation of selection are then (a) deep sequenced and analyzed to identify fit individuals and/or (b) re-translated and subjected to more rounds of selection, sequencing and analysis, until a molecule of suitable fitness is acquired.

The ability of the method of the present disclosure to produce a library for molecules of formula (I) that can be re-translated and re-selected in multiple generations is a marked advantage, because it allows for directed, multi-generation "evolution." Although both an initial population of sufficient complexity and the population of survivors after the first round of selection may be under-sampled by the best current, affordable, deep sequencing methods, and although statistical analysis of the sequencing data to identify fit individuals may suffer from that under-sampling, multi-generational selections can enable full analysis of the population. Because many unique, less fit individuals will be eliminated from the population with each successive round of selection, the actual complexity of the population will diminish as it is enriched with more fit individuals. Therefore, each round of sequencing will acquire an increasingly significant sampling, and will enable very robust computational analyses. The ability to perform multiple generations of selection vastly improves this sort of analysis.

The DNA 'genes', or oligonucleotides G, comprising the library have a somewhat familiar architecture. Like genes in a cell, the information is arranged along a linear sequence. However, unlike a typical gene, in this synthetic biological system, 'codons' or, coding regions, are typically about 20 bases long. In a natural system, codons are read in a linear order starting at one end of the gene and proceeding to the other. In an embodiment of the present disclosure, the coding regions comprising the gene can be read in any order so long as (a) the order begins with a terminal codon, (b) is predetermined, and (c) the predetermined order is maintained in all successive generations of that selection campaign. In addition, the genes also optionally incorporate non-coding regions between each coding region. These non-coding regions facilitate accurate translation of the library, and mutagenesis or gene-shuffling of the library if the non-coding regions possess unique restriction sites. Oligonucleotides G in a given library will typically all possess the same number of codons in a similar arrangement.

In certain embodiments, for a given library of oligonucleotides G, there will typically be a pre-determined set and number of sequences used at each coding region. In certain embodiments, no coding sequence used at one coding region is used at any other coding region. In some embodiments, the coding sequences are assembled into genes in a combinatorial way, such that all possible combinations of coding sequences are represented. In other embodiments, the number of combinations of coding sequences will be significantly diminished in the initial gene library, and after selection events, a portion of the population will undergo a gene-shuffling or crossing-over procedure to enable evolution and selection of new phenotypes.

In certain embodiments, these 'crossing-over' events are facilitated by placement of unique restriction sites within non-coding regions. Partial digest of the population at one or more of the non-coding regions followed by re-ligation, will allow a combinatorial re-assortment of coding sequences between the two coding regions where the digests were performed. This shuffling or crossing over event can be performed between a single pair of coding regions, or between multiple pairs of coding regions, or the library can be split into pools and each pool undergo crossing over events between different combinations of coding regions. In certain embodiments, this capacity in effect allows two individuals that have demonstrated fitness by surviving selection, to genetically recombine to encode an offspring phenotype different from either parent. Generally, by recombination of fit genotypes, new, more fit offspring phenotypes are produced for selection.

Identification of Encoded Portions

In some embodiments, the present disclosure provides multifunctional molecules that are molecular probes having a correspondence between the DNA gene sequence in oligonucleotide G and the identity of the encoded portion or molecule the gene encodes.

In some embodiments, the correspondence is established as follows. The gene library is prepared in a manner that makes the coding regions single-stranded and any non-coding regions double-stranded.

Separately, a reaction site adapter is prepared. Reaction site adapters (hairpin structures) will be described in greater detail below. Briefly, in certain embodiments, reaction site adapters are typically DNA hairpins functionalized with a reactive functional group, and comprising a stem region and an anti-coding region. In certain embodiments, as many reaction site adapters with as many different anti-coding sequences will be provided and prepared as there are terminal coding regions in the library. In certain embodiments, a reaction site adapter will be prepared with an anti-coding sequence complementary to each of the terminal coding region sequences. In certain embodiments, the reactive functional group reactive site on each reaction site adapter with its own sequence will be reacted with a first building block to produce a charged reaction site adapter (charged carrier anti-codon) and will be optionally purified to remove unreacted reaction site adapters, providing a marked advantage in translational fidelity. The anti-coding sequence of a reaction site adapter will thus correspond to a particular building block. This chemistry will be described in more detail below. A pool of charged reaction site adapters can be incubated with the gene library to allow charged reactive site adapters (charged carrier anti-codons) to specifically anneal to the terminal coding sequences for which they are the complement. The annealed adapter/library complex can then be ligated together, for example using T4 DNA ligase. In this manner, a terminal coding region of the gene will correspond to a particular building block.

In certain embodiments, establishing a correspondence between the next chosen coding region sequences and the next building blocks will be accomplished by sorting the library into subpools based on the coding sequences at the chosen coding region. In certain embodiments, this sorting is accomplished by sequence specific hybridization of the single-stranded coding sequences to complementary oligos immobilized on an array of solid supports termed a hybridization array.

The construction of hybridization arrays is described below. Briefly, in certain embodiments, a hybridization array is an array of spatially separated features containing solid supports. In certain embodiments, on these supports are covalently tethered ssDNA oligos with sequences complementary to the sequences of the coding region being sorted. In certain embodiments, by flowing a library of molecules of formula (I), or formula (II) bearing a plurality of coding sequences over or through a solid support bearing a given anti-coding sequence, the members of the library having the complementary coding sequence can be specifically immobilized. In certain embodiments, flowing the library over or through an array of solid supports each of which bears a different immobilized anti-coding sequence will sort the library into subpools based on coding sequence. In certain embodiments, each sequence-specific subpool can then be independently reacted with a specific building block (positional building block) to establish a sequence to building block correspondence. This synthesis will be described in more detail below, and can be performed on the hybridization array, or after the subpools have been eluted in subpools off of the array into a suitable environment, such as separate containers, for reaction.

Establishing coding sequence to building block correspondence for all other internal, non-terminal coding regions can be accomplished in the same way, the only difference being that a different hybridization array bearing a different set of anti-coding sequences is used as appropriate.

Coding regions in the oligonucleotides G may also encode other information. In certain embodiments, after translation of the library is complete, it may be desirable to sort the library based on index coding region sequences. In certain embodiments, index coding region sequences can encode the intended purpose, or the selection history of its corresponding subpool of the library. For example, libraries for multiple targets can be translated simultaneously together, and then sorted by the index coding region into subpools. Subpools intended for different targets, and/or for selections under different conditions can be thus separated from each other and made ready for use in their respective applications. The selection history of a library member undergoing multiple rounds of selections for various properties can thus be recorded in the index region.

One intended purpose of reaction site adapters is to establish a correspondence between a sequence in the gene library of oligonucleotides G and a particular building block. Broadly this is accomplished as described above. In general, the key elements of a reaction site adapter are an anti-coding sequence that will allow the adapter to hybridize to a specific coding region of an oligonucleotide G, a reactive functional group to which a first or second building block D or E can be covalently attached, a linker that covalently tethers such building blocks to the reaction site adapter, and a means for covalently attaching the building block-laden reaction site adapter, or charged reaction site adapter, directly or indirectly to the gene (oligonucleotide G). In some embodiments, the reaction site adapter is a DNA hairpin comprising a stem, a loop, and either a 3' or a 5' overhang which itself comprises the anti-coding sequence. In some embodiments, the stem may contain one or more unique restriction sites that upon cleavage with restriction enzymes can facilitate release of very tight binders from targets, or contain a good priming sequence to enable cleaner amplification of the gene by PCR.

In certain embodiments, the loop region performs the task of creating a change in directionality of the reaction site adapter strand to match that of the oligonucleotide G strand so that it can be ligated to the terminus of oligonucleotide G. Because of the nature of DNA, a coding sequence in oligonucleotide G will have the opposite directionality of an anti-coding sequence in a reaction site adapter. DNA ligations only occur between two ends of nucleic acids strand with the same directionality. That is, a strand oriented from 5' to 3' can be ligated to another strand oriented 5' to 3'. The loop region performs the task of creating a change in directionality of the reaction site adapter strand to match that of the oligonucleotide G strand so that it can be ligated to the terminus of oligonucleotide G. In some embodiments, the loop of the hairpin structure $H_1$ and/or $H_2$ includes between 3 and 12 DNA bases. In some embodiments, it is a polyethylene glycol linker comprised of 6-12 PEG units. In some embodiments, the reaction site adapter will be ligated to oligonucleotide G enzymatically. In some embodiments, the terminus of oligonucleotide G will be functionalized with an azide or an alkyne, and the terminus of the reaction site adapter will be functionalized with an alkyne or an azide and the ligation will be achieved through copper-mediated "click" chemistry. It will be appreciated by those skilled in the art that numerous equivalent chemistries are appropriate for covalently tethering the reaction site adapter to oligonucleotide G.

In some embodiments, the reactive site comprises a free amine tethered to a modified nucleobase by a PEG linker or alkyl chain linker, or by a homopolymer or heteropolymer chain linker. The reactive site can be functional when linkered at any point on the reaction site adapter hairpin. In some embodiments, the reactive site is linkered on the stem at a location that is 5' of the loop. In some embodiments, the reactive site is linkered 3' of the loop. In some embodiments, the reactive site is linkered on the same side of the loop as the anti-coding sequence and near the initial base of the anti-coding sequence. In some embodiments, the reactive site is linkered on the opposite side of the loop from the anti-coding sequence and distal from it along the stem. In some embodiments, more than one reactive site is linkered on the adapter. One advantage of having more than one reactive site is that the probability of a correctly synthesized encoded portion is increased. Another advantage of having more than one reactive site is that during selections, the multiplicity of encoded portions may engender avidity, allowing weaker binders to be found in selection. In some embodiments with two or more reactive sites, the reactive sites will be linkered on the same side of the loop and near opposite ends of the stem. In some embodiments the reactive sites will be positioned on opposite sides of the loop and near opposite ends of the stem. In some embodiments with more than one reactive site, both reactive sites will be in the loop region. In some embodiments, the reaction site adapter will comprise more than one stem and more than one loop. In such embodiments, multiple reactive sites may be linkered along the stems, or on the loops or in combinations of both. In some embodiments, the arrangement and positioning of reactive sites will be designed to facilitate better results in selections by tailoring the distance between reactive sites to facilitate better avidity based on the size of the targets in question.

In some embodiments, the reaction site adapter will possess a means of being readily broken into smaller fragments. Such fragmentation may facilitate better downstream processing of the library, for example, the presence of a ligated hairpin at one or both ends of a template library strand may complicate PCR amplification by interfering with the ability of primers to correctly anneal to molecules of formula (I). In another example, fragmentation of the charged reaction site adapter after ligation may decrease the steric bulk near reactive sites and improve chemistry, or improve yields during hybridization. The means of fragmentation include, but are not limited, to restriction digestion at a unique restriction site in the stem region, or incorporation of dU bases in the synthesis of the reaction site adapter followed by treatment with uracil DNA glycosylase to create an apyrimidinic site and subsequent alkaline hydrolysis of the strand. The means of fragmentation may leave a reactive site tethered directly or indirectly to the template strand or it may remove it from the template strand.

In some embodiments, charged reaction site adapters will be specifically hybridized and ligated to terminal coding regions at both ends of the template strand. In the case where the terminal coding regions encode a first and second building block that are the same, these embodiments have the advantages of providing multiple possibilities for the correct encoded portion to be synthesized. In addition, these embodiments can provide the opportunity for a multiplicity of encoded portions to engender avidity and improve selection efficiency, especially for weaker binders. In the case where the first and second building blocks are different, these embodiments allow twice as many unique encoded portions to be synthesized for the same number of gene template strands. In cases where the first and second building block are the same for some molecules of formula (I), and different for other molecules of formula (I), it allows analysis of the relative contribution to overall fitness the two different building blocks confer on the whole encoded portion.

Many kinds of chemistry are available for use in this invention. In theory, any chemical reaction could be used that does not chemically alter DNA. Reactions that are known to be DNA compatible include but are not limited to: Wittig reactions, Heck reactions, homer-Wads-worth-Emmons reactions, Henry reactions, Suzuki couplings, Sonogashira couplings, Huisgen reactions, reductive aminations, reductive alkylations, peptide bond reactions, peptoid bond forming reactions, acylations, SN2 reactions, SNAr reactions, sulfonylations, ureations, thioureations, carbamoylations, formation of benzimidazoles, imidazolidinones, quinazolinones, isoindolinones, thiazoles, imidazopyridines, diol cleavages to form glyoxals, Diels-Alder reactions, indole-styrene couplings, Michael additions, alkene-alkyne oxidative couplings, aldol reactions, Fmoc-deprotections, trifluoroacetamide deprotections, Alloc-deprotections, Nvoc deprotections and Boc-deprotections. (See, Handbook for DNA-Encoded Chemistry (Goodnow R. A., Jr., Ed.) pp 319-347, 2014 Wiley, New York. March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Coltman et al., Principles and Applications of Organotransition Metal Chemistry, University Science Books, Mill Valley, Calif. (1987), Chapters 13 to 20; each of which is incorporated herein by reference in its entirety.)

It will be understood by one skilled in the art that a vast assortment of different combinatorial scaffolds can be incorporated into multifunctional molecules of the present disclosure. Examples of the kinds of general classes of scaffolds include but are not limited to the following: (a) chains of bifunctional building blocks connected end to end, peptides and peptoids are two examples of this kind of scaffold; it will be appreciated that not every bifunctional building block in the chain will have the same pair of functional groups, and that some building blocks may have only one functional group, e.g. terminal building blocks, (b) branching chains of bifunctional building blocks that include some tri-functional building blocks, and may or may not include mono-functional building blocks, (c) molecules comprised of a single polyfunctional building block, and a set of monofunctional building blocks; in one embodiment, such a molecule may have a polyfunctional building block that acts as a central core, to which other mono-functional building blocks are added as diversity elements, (d) molecules comprised of two or more polyfunctional building blocks to which are connected a set of monofunctional or bifunctional building blocks as diversity elements, (e) any of the above scaffolds that includes formation of ring by reacting a moiety on the linker or a building block installed at an earlier step with a moiety on a building block or the linker installed at a later step. Other scaffolds or chemical structural phyla can also be incorporated, and these general structural scaffolds are only limited by the ingenuity of the practitioner in designing the chemical pathways to synthesize them.

In certain embodiments, ion-exchange chromatography facilitates the chemical reactions performed on substrates tethered to DNA in two ways. For reactions conducted in aqueous solvent, purification can be readily accomplished by pouring the reaction over an ion exchange resin like DEAE-SEPHAROSE®, or TOYOPEARL® SuperQ 650M. In certain embodiments, the DNA will be bound to the resin by ion exchange, and unused reactants, by-products and other reaction components can be washed away with aqueous buffers, organic solvents or mixtures of both. For reactions that work best in organic solvent, a real problem exists: DNA has very poor solubility in organic solvents, and such reactions suffer from low yields. In these cases, library DNA can be immobilized on ion exchange resin, residual water washed away by a water miscible organic solvent, and the reaction performed in an organic solvent that may or may not be water miscible. See, for example, R. M. Franzini, et.al. Bioconjugate Chemistry 2014 25 (8), 1453-1461, and references therein. Many types and kinds of ion exchange media exist, all having differing properties that may be more or less suited to different chemistries or applications, and which are commercially available from numerous companies like THERMOFISHER, SIGMA ALDRICH, DOW®, DIAION® and TOYOPEARL® to name only a few. It will be appreciated that there are many possible means and media by which library DNA might be immobilized or solubilized for the purpose of conducting a chemical reaction to install a building block, or remove a protecting group, or activate a moiety for further modification, that are not listed here.

In certain embodiments, a hybridization array comprises a device for sorting a heterogeneous mixture of ssDNA sequences by sequence specific hybridization of those sequences to complementary oligos that are immobilized in a position-addressable format. See, for example, U.S. Pat. No. 5,759,779. It will be appreciated that hybridization arrays may take on many physical forms. In certain embodiments, hybridization arrays possess the ability for a heterogenous sample or ssDNAs (i.e. a library of compounds of formula (I)) to come into contact with complementary oligos that have been immobilized on a surface of the array. The complementary oligos will be immobilized on a surface of the array in a manner that enables, allows or facilitates sequence-specific hybridization of the ssDNA to the immobilized oligo, thereby immobilizing the ssDNA as well. In certain embodiments, ssDNAs that have been immobilized through a common sequence can be independently removed from the array to form a subpool.

In some embodiments, the hybridization array will be a chassis comprising a rectangular sheet of plastic between 0.1 and 100 mm thick into which has been cut a series of holes, termed 'features'. In certain embodiments, on the underside and top of the sheet will be adhered filter membranes. In certain embodiments, in the features, trapped between the filter membranes, will be a solid surface or collection of solid surfaces, termed 'solid support.' In certain embodiments, a single sequence of oligo will be immobilized on the solid support in any given feature.

In certain embodiments, a library of molecules of formula (I or II) can be sorted on the array by allowing an aqueous solution of the library to flow over and through the features. In certain embodiments, as members of the library come in contact with oligos in features bearing complementary sequences, they become immobilized within the feature. In certain embodiments, after hybridization is complete, the features of the array can be positioned over a receiver vessel, like a 96-well plate or a 384-well plate. In certain embodiments, addition of an alkaline solution that causes the de-hybridization of DNA can be added to each feature and the solution will carry the library, now mobile, into the receiver vessel. Other methods of de-hybridizing are also possible, like the use of hot buffer, or denaturing agents. Thus, in certain embodiments, a library of molecules can be sorted into subpools in a sequence specific manner.

It will be appreciated, that the chassis described above could be comprised of plastic, ceramic, glass, polymer or metal. It will be appreciated that the solid supports can be comprised of a resin, glass, metal, plastic, polymer or ceramic, and that the supports can be porous or non-porous. It will be appreciated that higher surface areas on the solid supports allow for larger amounts of complementary oligos to be immobilized and larger amounts of library subpools can be captured in the feature. It will be appreciated that the solid supports can be held in their respective features by filter membranes made of nylon, plastic, cloth, polymer, glass, ceramic or metal. It will be appreciated that the solid supports can be held within their respective features by means other than filter membranes, like glue, adhesives, or covalent bonding of the support to the chassis and/or to other supports. It will be appreciated that the features may or may not be holes in a chassis, but independent constructs which can be taken out of or placed in a chassis. It will be appreciated that the shape of the chassis need not be rectangular with features arranged in 2 dimensions, but could be cylinder or rectangular prism with features arranged in one dimension or 3 dimensions. See, for example, U.S. Pat. No. 5,759,779.

Libraries of molecules of formula (I) can be thought of as populations of phenotypes tethered to their respective genotypes. Such a population can be subjected to a selection pressure that removes less fit individuals from the population, and allows more fit members to survive. The oligonucleotide G genotypes of the second generation population—those surviving selection—can be amplified by PCR, re-translated, and subjected to another, more stringent selection for the same trait, or selected for some orthogonal trait. The subpopulation surviving a selection can also be sequenced, typically using deep sequencing or next-generation sequencing techniques, and the sequencing data can be analyzed to identify the encoded portions (phenotypes) that are the most fit.

Numerous kinds of selection can be performed. The most typical selection is performed to find individuals in the population that are capable of binding to a target protein. In certain embodiments, a method of performing such a selection is to immobilize the target protein on a solid support, like the surface of a well in a NUNC MAXISORP® plate, or by biotinylating the target and immobilizing on streptavidin-coated magnetic beads. In certain embodiments, after immobilization of the target, the population of molecules of formula (I) is incubated with the target on the support. All those individuals capable of binding the target will do so, and become immobilized themselves. Washing the solid support with an appropriate buffer, removes the non-binders. In certain embodiments, the DNA encoding the binders can be amplified by PCR and either sent for sequencing for re-translated and subjected to another round of selection.

In certain embodiments, selections can be performed in a way that selects individuals that bind one target protein to the exclusion of a different, anti-target, protein, or a set of anti-target proteins. In such a case, one method of selection requires both the target and the anti-target(s) be immobilized on solid supports in separate vessels. In certain embodiments, the library is first incubated with the anti-target, and individuals that can bind the anti-target do so. In certain embodiments, the non-binders are carefully removed from the vessel and transferred to the vessel containing the target. In this manner, the population being selected for the ability to bind the target is first depleted in individuals capable of binding the anti-target, and the selection produces individuals whose fitness is characterized as the ability to bind the target or the exclusion of the anti-target.

In certain embodiments, a second method of identifying encoded portions binding one target selectively over another, is to perform parallel selections for both targets, and then eliminate encoded portions demonstrating affinity to both targets during analysis of sequencing data.

In certain embodiments, selections can also be performed that select for binders with long off-rates by using a mixture of immobilized target and free target. In certain embodiments, the library is incubated with immobilized target, allowing binders to bind. Then an excess of free target is added and incubated for a predetermined amount of time. During that time, any binders that release from the immobilized target and then rebind have a high probability of rebinding to the free target. Upon washing away non-binders, the free target, and anything bound to it will also be washed away. The only binders left behind on the free target are those binders whose off-rates are longer than the pre-determined incubation time of the free target.

The methods of selection described in the preceding paragraphs can be found in the literature for phage display, ribosome display, and mRNA display. See, for example, Amstutz, Patrick, et al., Cell biology: a laboratory handbook, 3rd ed. ELSEVIER, Amsterdam (2006): 497-509, and references therein.

In principle, selections can be performed for any property, provided a means can be constructed that selectively amplifies those individuals in the population that have the property over those individuals that do not. Selections for pharmacologically relevant properties other than target binding are possible in principle and examples include, but are not limited to, selections for water-solubility, cell membrane penetrance, and non-toxicity.

It will also be appreciated, that synthesis of a library in sufficient amounts may allow for more than one selection to be performed in a given round. In certain embodiments, the subpopulation of survivors after a selection for affinity to a target, could be isolated, optionally purified, and subjected to a second selection for affinity to the same or to different targets, or selected for an orthogonal property. In certain embodiments, the subpool of survivors is then amplified by PCR and sequenced, or it is amplified and re-translated for further selections.

In certain embodiments, the sequencing data is analyzed by comparing the representation of a library member in the population before and after selection. In certain embodiments, members less represented after selection are typically deemed less fit, and those more represented after selection are deemed more fit. In addition, the data is optionally analyzed to determine which individual building blocks confer fitness, which pairs of building blocks confer fitness, and which triplets of building blocks confer fitness when coupled in the same encoded portion. In certain embodiments, the data is optionally analyzed to determine which structural elements within different building blocks and within different encoded portions confer fitness on selected members of the library. In certain embodiments, these analyses inform which members should be synthesized for independent testing, and suggest analogous molecules that should be made and tested which may not be native members of the library. In certain embodiments, three-dimensional docking algorithms can also inform these processes.

In certain embodiments, library members identified in data analysis, can be synthesized with or without the oligonucleotide portion, typically using the same or similar synthetic conditions that were used in making the library. In certain embodiments, these independently synthesized samples can then be subjected to various tests that characterize its physical and chemical properties and suggest its general fitness for a desired task. In certain embodiments, these properties include but are not limited to the dissociation constant or KD which measures the tightness of the library member's binding to its target, its water solubility as measured by a water: octanol partition, and its cell penetrance measured in CaCo cells.

In certain embodiments, identified library members that bind a biomolecule can be used to ascertain the biological function of that biomolecule. In certain embodiments, the functions of many proteins are not known, and the method of the present disclosure provides a ready path to discovery of molecule probes to aid in the elucidation of those functions. In certain embodiments, library members identified by the method of the present disclosure can be used to help determine if a biomolecule is specifically amenable to small molecule discovery and to targeting for drug intervention.

In certain embodiments, the effect on biomolecule function of binding the library member to it can be assayed in in vitro assays or in in vivo assays, in cell-based or in non-cell-based assays. For biomolecules with known function, the effect of the identified library member on that function can be assessed. If the biomolecule is an enzyme, effects on its rates of activity can be assessed. If it is a signaling protein, effects on cellular function can be assessed, including cell viability, cell gene expression, or cellular phenotype expression. If the target is a viral protein, the effect of the library member on viral proliferation and viability can be assessed.

In certain embodiments, library members identified through selections can also be evaluated for their effects on animal and human and plant health in in vivo experiments.

In certain embodiments, library members identified through selections can also be used as affinity reagents for the purification of the biomolecule target. In certain embodiments, the identified encoded portion can be immobilized on a solid support, and a heterogeneous solution containing the target can be flowed over the solid support. In certain embodiments, the target will be bound to the encoded portion, and immobilized. In certain embodiments, all other components of the mixture can be washed away, leaving a purified sample of the target behind.

This invention is illustrated by but not limited by the following examples. Those skilled in the art will recognize many equivalent techniques for accomplishing the steps or portions of the steps enumerated herein.

EXAMPLES

An embodiment of a molecule of formula (I) is constructed as follows.

Example 1

Construction of a $8 \times 10^9$—Member Gene Library

Provision of codons for the gene library. 96 double stranded DNA ("dsDNA") sequences are provided or purchased from a gene synthesis company like Genscript in Piscataway NJ, Synbio Technologies in Monmouth Junction NJ, Biomatik of Wilmington DE, Epoch Life Sciences of Sugarland TX, among others. These sequences comprise 5 coding regions of 20 bases each. Each coding region is flanked by a 20-base non-coding region (making a total of 6 non-coding regions). All of the coding region sequences are unique, and chosen to be un-cross-reactive with other coding regions and with the non-coding regions. The 5 non-coding regions in a DNA molecule have different sequences, but the sequence at each position is conserved across all the DNAs. All coding and non-coding regions are designed to have similar melting temperatures (between 58° C. and 62° C.). Coding and non-coding regions are designed in silico as follows. DNA sequences are generated randomly in silico.

Once generated, the sequence melting temperature and thermodynamic properties (delta H, delta S and delta G of melting) are calculated using the nearest neighbor method. If the calculated Tm and other thermodynamic properties are not within the predefined range desired for the library, the sequence is rejected. Acceptable sequences are subjected to analysis by sequence similarity algorithms. Sequences predicted by the algorithm to be sufficiently non-homologous are presumed to be non-cross-reactive, and are kept. Others are rejected. Coding and non-coding regions are sometimes chosen from empirical lists of oligos shown to be non-cross hybridizing. See, Giaever G, Chu A, Ni L, Connelly C, Riles L, et al. (2002) Functional profiling of the Saccharomyces cerevisiae genome. Nature 418: 387-391. This reference lists 10,000 non-cross-reactive oligos. The Tm of each is calculated and those falling within the predefined range are analyzed by sequence homology algorithms. Those which are sufficiently non-homologous are retained.

Each non-coding region contains a unique restriction site. The non-coding region at the 5' end of the template strand contains a SacI recognition site at bases 13-18 from the 5' end. The non-coding region at the 3' end of the coding strand contains an EcoRI restriction site at bases 14-19 from the 3' end of the template strand. The second, third, fourth and fifth non-coding regions from the 5' end of the template strand have HindIII, NcoI, NsiI, and SphI recognition sites respectively at bases 8-13.

DNAs are restriction digested to de-couple all codons from each other. The DNA sequences are pooled and dissolved in CUTSMART® buffer from New England Biolabs (NEB, Massachusetts) at a concentration of about 20 μg/ml. The internal restriction enzymes, HINDIII-HF®, NCOI- HF®, NSII-HF® and SPHI—HF® from NEB are added and the digestion is done for 1 hour at 37° C., following enzyme the manufacturer's protocols. The enzymes are heat inactivated at 80° C. for 20 minutes. After inactivation, the reaction is held at 60° C. for 30 minutes, then cooled to 45° C. and held for 30 minutes, and then cooled to 16° C.

The codons are combinatorially re-assorted to produce a gene library. To re-assemble the individual codons produced in the digestion reaction into full-length genes, T4 DNA Ligase from NEB is added to the reaction to 50 U/ml, dithiothreitol (DTT, Thermo Fisher Scientific, Massachusetts) is added to 10 mM, and adenosine 5'-triphosphate (ATP, from NEB) is added to 1 mM in accordance with the manufacturer's protocol. The ligation reaction is performed for 2 hours, and the product is purified by agarose gel electrophoresis. Because the sticky-ends produced by digestion at one site of a provided gene will anneal to the sticky-ends of all the other digestion products at the same site, a complete combinatorial re-assortment will occur. Thus, 96 provided genes comprised of 5 codons each would produce 965 genes. Because there are 96 coding sequences at each of 5 coding positions, there are $96^5 = 8 \times 10^9$ combinations or library members.

The gene Library is Prepared for Translation.

Amplify the Gene Library by PCR. A T7 promoter is appended to the 5' end of the non-template strand by extension PCR using these reactants for a 50 μL reaction: 5×PHUSION® High-Fidelity DNA Polymerase ("PHUSION® Polymerase", NEB), 10 μL; deoxynucleotide (dNTP) solution mix 200 μM final concentration; forward primer, final concentration 750 nM; reverse primer final concentration, 750 nM; template (enough template should be used to adequately oversample the library); dimethyl sulfoxide (DMSO), 2.5 uL; "PHUSION® Polymerase", 2 μL. Perform the PCR using an annealing temperature of 57° C., and an extension temperature of 72° C. Anneal for 5 seconds each cycle; extend for 5 seconds each cycle. Analyze the product by agarose gel electrophoresis.

Transcribe the DNA into RNA. Without purification of the PCR product, a 250 μL transcription reaction is done with the following reactants: PCR product, 25 μL; RNAse-free water, 90 μL; nucleoside triphosphate's (NTP), 6 mM final concentration in each; 5×T7 buffer, 50 μL; NEB T7 RNA polymerase 250 units; optionally, RNasin® Ribonuclease Inhibitors (Promega Corporation, WI) can be added to 200 U/ml; optionally, pyrophosphatase can be added to 10 μg/ml. 5×T7 buffer contains: 1M HEPES-KOH (4-(2-hydroxyethyl)-1-piperazineethanesulfonic acid) pH 7.5; 150 mM magnesium acetate; 10 mM spermidine; 200 mM DTT. The reaction is conducted at 37° C. for 4 hours. The RNA is purified by lithium chloride precipitation. Dilute the transcription reaction with 1 volume of water. Add LiCl to 3M. Spin at maximum g, at 4° C. for at least 1 hr. Decant the supernatant and keep it. A clean pellet will be a clear, glassy, gel that can be difficult to dissolve. Alternating gentle warming (a minute at 70° C.) and gentle vortexing will cause the pellet to re-suspend. Analyze by agarose gel electrophoresis, quantitate and freeze as soon as possible to avoid degradation. See, for example, Analytical Biochemistry 195, p 207-213. (1991), and Analytical Biochemistry 220, p 420-423, (1994).

Reverse Transcribe the RNA into DNA. The single stranded RNA ("ssRNA") is reverse transcribed in a 2 step procedure using SUPERSCRIPT III Reverse Transcriptase from Thermo Fisher Scientific and the supplied First Strand Buffer. The first step is done with these final concentrations of the following components: dNTP's, 660 μM each; RNA template, ~5 µM; primer, 5.25 µM. The Step 1 components are heated to 65° C. for 5 minutes, then iced for at least 2 min. The Step 2 components final concentrations are: First Strand Buffer, 1×; DTT, 5 mM; RNase Inhibitor (NEB), 0.01 U/uL, SUPERSCRIPV III Reverse Transcriptase, 0.2 U/µl. The Step 2 components are combined, warmed to 37° C., and after the Step 1 components have been iced 2 minutes, the Step 2 mix is added to the Step 1 mix. The combined parts are reacted at 37° C. for 12 hours. The reaction is followed by agarose gel electrophoresis. Take samples of the reaction, of known starting material RNA and of known product, or known product analog like PCR product library. Add ethylenediaminetetraacetic acid ("EDTA") to all samples, heat to 65° C., 2 minutes, flash cool, and then run on an agarose gel. ssRNA should resolve from complementary DNA ("cDNA") product. The cDNA product is purified by adding 1.5 volumes of isopropanol and ammonium acetate to 2.5 M, followed by centrifugation at 48,000 g for 1 hour. The cDNA pellet is re-suspended in distilled water ("dH₂O") and the RNA strand is hydrolyzed by adding LiOH to pH 13. The solution is heated to 95° C. for 10 minutes. 1.05 equivalents of primers specific for the non-coding regions are added, the pH is brought to neutral with tris(hydroxymethyl)aminomethane ("Tris") and acetic acid, and the reaction is allowed to cool to room temperature slowly, whereupon it is concentrated and buffer exchanged into NEB CUTSMARV buffer.

Removal of terminal non-coding regions. The ssDNA product of the reverse-transcription with complementary oligos making the non-coding regions double stranded is suspended in NEB CUTSMART® Buffer at a concentration of 100 µg/ml. Restriction enzymes. SACI-HF®, and ECORI-HF® from NEB are added to a concentration of 1 U/µg of DNA. The digestion is incubated for 1 hour at 37° C., and then the enzymes are heat inactivated at 65° C. for 20 minutes.

Reaction Site Adapters are Prepared for Translation.

Provision of Reaction Site Adapters. Two sets of 96 reaction site adapters are provided, each comprising a hairpin loop, a stem, and an overhang that comprises an anti-coding sequence. One set has a 3' overhang anti-coding sequence that specifically hybridizes to the 3' terminal coding region of the template strand as it appears after removal of the 3' terminal non-coding region; the other set has a 5' overhang anti-coding sequence that specifically hybridizes to the 5' terminal coding region of the template strand as it appears after removal of the 5' terminal non-coding region. The set bearing 3' overhangs are provided with 5' phosphoryl groups. In this example, the stem region of each set possesses the same sequence of the corresponding terminal non-coding region removed by restriction digestion previously. The loop regions of each set bear a base modified with a linkered reactive site. N4-TriGl-Amino 2'deoxycytidine (from IBA. Goettingen, Germany). Adapters as described here can be purchased from DNA oligo synthesis companies like Sigma Aldrich, Integrated DNA Technologies of Coralville, IA, or Eurofins MWG of Louisville, KY.

Charging of reaction site adapters. The two sets of 96 reaction site adapters are provided in separate wells, and dissolved in TE buffer (Promega, MA). 15 µl of TOYOPE-ARL® SuperQ-650M (Sigma-Aldrich, St. Louis, MO) ion exchange resin is placed in each well of a filter plate and washed with 100 µl of 10 mM HOAc. Aliquots of each reaction site adapter proportionate to the amount of template strand are transferred into separate wells of the filter plate wherein they are immobilized on the resin. The adapters immobilized on the resin are washed with dH₂O, then with piperidine, then with dimethylformamide ("DMF"). 96 reaction solutions are made separately, each containing: 50 µl of DMF, an Fmoc-protected amino acid at 75 mM, 4-(4,6-Dimethoxy-1,3,5-triazin-2-yl)-4-methyl morpholinium tetrafluoroborate at 75 mM, N-methyl morpholine at 90 mM. These mixtures are allowed to activate the acid for ten minutes at room temp then added to the resin and reacted for 30 minutes. The resin is then washed 4×100 µl with DMF, and the coupling step repeated with a freshly prepared reaction mixture, washed again with DMF, and the Fmoc protecting group is removed by adding 50 µl of 20% piperidine in DMF to each well and incubating for 2 hours at room temperature. The resin is washed again 4×100 µl with DMF, then 3×100 µl with dH₂O. The charged reaction site adapters are eluted off the resin with 1.5 M NaCl, 50 mM KOH, 0.01% TRITON™ X-100. The solution is neutralized by addition of Tris to 15 mM and HOAc to pH 7.4. The charged reaction site adapters are then pooled and desalted by passing over a ZEBA™ 7K MWCO (Thermo Fisher Scientific, MA) desalting cartridge.

Translation of the Library

Ligation of charged reaction site adapters to the library. The restriction digested template library is buffer exchanged using ZEBA™30K MWCO (Thermo Fisher Scientific, MA) centrifugal concentrators to 50 mM Tris-HCl, 10 mM MgCl₂, 25 mM NaCl, pH 7.5@25° C. 1.1 equivalents of charged reaction site adapters specific for the 3' end of the template strand are added; 1.1 equivalents of charged reaction site adapters specific for the 5' end of the template strand are added, and the mixture is diluted with the same buffer to a template strand concentration of 1 µM. The reaction is warmed to 65° C. for 10 min and allowed to cool to 45° C. over 1 hr, and held at 45° C. for 4 hours. After cooling to room temperature, DTT is added to 10 mM, ATP is added to 1 mM, and T4 DNA Ligase is added to 50 U/mL. The ligation reaction is run at room temp for 12 hours, then the enzyme is heat inactivated at 65° C. for 10 min, and the reaction cooled slowly to room temperature. The reaction is buffer exchanged and concentrated with a 30K molecular weight cut-off (MWCO) centrifugal concentrator into 150 mM NaCl, 20 mM citrate, 15 mM Tris, 0.02% sodium dodecyl sulfate ("SDS"), 0.05% Tween20 (from Sigma-Aldrich), pH 7.5.

Preparation of a hybridization array. Hybridization arrays are constructed of a TECAFORM™ (Acetal Copolymer) chassis ~2 mm thick, with holes cut by a computer numerical control machine. A nylon 40 micron mesh from ELKO FILTERING is adhered to the bottom of the chassis using NP200 double-sided tape from Nitto Denko. The holes are then filled with a solid support of CM SEPHAROSE® resin (Sigma Aldrich) which has been functionalized with an azido-group. The resin is functionalized using azido-PEG-amine with 8 PEG units purchased from Broadpharm (San Diego, CA). 45 ml of packed CM SEPHAROSE® is loaded into a fritted funnel and washed with DMF. The resin is then suspended in 90 ml of DMF and reacted with 4.5 mM azido-PEG-amine, 75 mM EDC, 7.5 mM HOAt, 12 hours at room temp. The resin is washed with DMF, water, isopropanol and stored in ethanol 20% at 4° C. A nylon 40 micron mesh is then adhered to the top of the chassis. The azido group allows alkyne-linked oligos to be tethered to the solid support using click chemistry. Placing the array in an array-to-well-plate adapter, and stationing the adapter over a well plate enables capture oligos to be 'clicked' onto the azido-SEPHAROSE® in register. A 30 µl solution containing 1 nmol of alkynyl oligo, copper sulfate, 625 µM tris(3- hydroxy-propyl-triazolyl-methyl)amine ("THPTA") (ligand), 3.1 mM amino-guanidine, 12.5 mM ascorbate, 12.5 mM phosphate buffer pH 7, 100 mM, is added to each well of the array-to-well-plate adapter and allowed to adsorb onto the SEPHAROSE® support. After 10 minutes, the solution is spun in a centrifuge out of the array and into the plate, whereupon it is re-pipetted in register back onto the array for a second pass at the reaction. After a second 10 minute reaction, the reaction solutions are spun into the well plate, and the well plate is set aside. The array is washed well with 1 mM EDTA, and stored in phosphate buffer solution ("PBS") with 0.05% sodium azide. The reaction solutions are each diluted to 100 µl with dH$_2$O, loaded onto diethylaminoethyl (DEAE) ion exchange resin, washed with dH$_2$O to remove all reagents and reaction by-products except for any un-incorporated oligo. These solutions are analyzed by high-performance liquid chromatography (HPLC) to ascertain the degree of incorporation by disappearance of starting material. One array bears oligos complementary to one coding position in the template library. A separate array is made for each coding position.

Sorting a library by sequence-specific hybridization. The hybridization-ready library is diluted to 13 ml in 1× Hybridization Buffer (2× saline sodium citrate (SSC), +15 mM Tris pH7.4+0.005% TRITON® X100, 0.02% SDS, 0.05% sodium azide). 10 µg of transfer RNA ("tRNA") are added to block non-specific nucleic acid binding sites. An array is chosen corresponding to the desired coding position in the template library. The array is placed in a chamber that provides 1-2 mm of clearance on either side, and the 13 ml library solution is poured in. The chamber is sealed and rocked gently for 48 hours at 37° C. Optionally, the array is placed in a device that allows the solution containing the library to be pumped in a directed fashioned though the various features in a pre-patterned path as means to sort the library on the array faster.

Eluting sorted library off of a hybridization array. The array is washed by unsealing the chamber and replacing the hybridization solution with fresh 1× hybridization buffer, followed by rocking at 37° C. for 30 minutes. The wash is repeated 3 times with hybridization buffer, then 2 times with ¼ hybridization buffer. The library is then eluted off of the array. The array is placed in an array-to-well-plate adapter, and 30 µl of 10 mM NaOH, 0.005% TRITON® X-100 is added to each well and incubated 2 minutes. The solution is spun in a centrifuge through the array into a well plate. The elution procedure is done 3 times. The sorted library solutions are neutralized by adding 9 µl of 1M Tris pH 7.4 and 9 µl of 1M HOAc, in that order, to each well.

Performing a peptoid coupling chemical step on sorted library. 15 µl aliquots of SuperQ 650M resin are added to each well of a filter plate, and washed with 100 µl of 10 mM HOAc. The sorted library is transferred in register from the well plate into which it is spun during elution off of the hybridization array into the well plate bearing the ion exchange resin. The resin and library are washed 1×90 µl with 10 mM HOAc, 2×90 µl with dH2O, 2×90 µl DMF, 1×90 µl piperidine. Separately, make a solution containing 100 mM sodium chloroacetate and 150 mM 4-(4,6-Dimethoxy-1,3,5-triazin-2-yl)-4-methyl morpholinium chloride in methanol. Add 40 µl of this solution to each well of resin and react at room temperature for 30 minutes. Wash the resin 3×90 µl methanol, then repeat the coupling and wash 3×90 µl methanol, 3×90 µl DMSO. Separately, make 2M (or saturated where necessary) solutions of primary amines in DMSO. Add 40 µl of one primary amine solution to each well of resin and react at 37° C. for 12 hrs. Wash the resin 3×90 µl DMSO, 3×90 µl 10 mM acetic acid (HOAc), 3×90 µl dH$_2$O. Elute the DNA library off of the ion exchange resin with 1.5 M NaCl, 50 mM NaOH, 0.005% TRITON® X-100 in 3×30 µl portions. Pool all the reactions, and neutralize the solution by addition of Tris to 15 mM and HOAc to pH 7.4. Concentrate and buffer exchange into 1× hybridization buffer.

Complete the synthesis of the library. Using the protocols above for sorting the library on hybridization arrays, and using the protocols above for performing peptide or peptoid chemistry, or those below in Examples 10-32 for performing other chemical steps, three more steps of sorting and synthesis are done and the library is fully translated.

Prepare the library for selection. Once translation of the library is complete, the single-stranded regions are optionally made double-stranded by combining the library as template in dH$_2$O at less than or equal to 1.0 µM, DREAMTAQ™ buffer at 1×, dNTP's at 11100× [template], DREAMTAQ™ Polymerase at 0.2 U/µl, and a supplement of an equimolar amount of MgCl$_2$ for each dNTP. Note that the reaction site adapter at the 3' end will act as the primer for this reaction. Heat the mixture to 95° C. for 2 minutes, then anneal at 57° C. for 10 seconds and extend at 72° C. for 10 minutes. Purify the reaction by ethanol precipitation.

Select ligands that bind to protein target of interest. 5 µg of streptavidin in 100 µl of PBS is immobilized in 4 wells of a MAXISORP™ plate with rocking at 4° C. overnight. The wells are washed with PBST 4×340 µl. Two of the wells are blocked with 200 µl of casein, and 2 others with BSA at 5 mg/ml for 2 hours at room temperature. The wells are washed with PBST 4×340 µl. 5 µg of a biotinylated target protein in 100 µl of PBS are added to a well blocked with casein, and to a well blocked with BSA and incubated with rocking at room temperature for 1 hour (for a protocol on the biotinylation of proteins, see Elia, G. 2010. Protein Biotinylation. Current Protocols in Protein Science. 60:3.6:3.6.1-3.6.21). A 100 µl aliquot of the translated library in PBS with Tween 20 (PBST) is added to each of the wells that did NOT receive the target protein, and 100 µl of PBST is added to the two wells that did receive target protein. The samples are incubated with rocking at room temperature for 1 hour. The buffer is carefully aspirated from the wells containing immobilized target protein and PBST only. The buffer containing library in wells without the target is carefully transferred to target-containing wells. 100 µl PBST are added to the wells without target. All are incubated for 4 hours with rocking at room temperature. The library is carefully removed with a pipette and stored. The wells are washed with 4×340 µl PBST. To elute library members binding tightly to the target protein, an excess of biotin in 100 µl of PBST is added to the wells and incubated for 1 hour at 37° C. The buffer is carefully aspirated and used as the template for a PCR reaction.

Analyze selection results. PCR products from the library before and after selection are submitted for deep sequencing using the primers and protocols required by the DNA Sequencing service provider. Providers include Seqmatic of Fremont CA, and Elim BioPharm, Hayward, CA The coding sequences at the terminal and internal coding regions of each sequenced strand are analyzed to deduce the building blocks used in synthesis of the encoded portion. The relative frequency of identified library members before selection and after suggests the degree to which the library member is enriched in the population by the selection. Analysis of the various chemical subgroups comprising the library members surviving selection shows the degree to which those moieties confer fitness on a library member and are used to evolve more fit molecules or to predict analogous molecules for independent synthesis and analysis.

Example 2

Prepare and Translate a Library with a Single Reaction Site Adapter

A library with a single reaction site adapter is prepared exactly as per Example 1 with the exception that the steps of (a) removal of one of the terminal non-coding regions, and (b) ligation of the corresponding reaction site adapter, are omitted.

Example 2a

Prepare and translate a library with a single reaction site adapter at the 5' end of G. To prepare a library with a single reaction site adapter at the 5' end of the coding strand of G, the library may be prepared exactly as per Example 1, except in the step, "removal of the terminal non-coding regions," the only restriction endonuclease added should be SacI. Doing so will remove the 5' terminal non-coding region, so that the 5' charged reaction site adapters can appropriately hybridize and ligate to the template strand. Using only the restriction endonuclease specific for a recognition site in the 5' terminal non-coding region and omitting the restriction endonuclease specific for a recognition site in the 3' terminal non-coding region will leave the 3' terminal non-coding region in place, disallowing ligation of 3' reactive site adapters to that terminus. Addition of the 5' charged reaction site adapters in the step, "ligation of charged reaction site adapters to the library," is done as in Example L Addition of the 3' charged reactive site adapters in that step is omitted. The reaction site adapter in this example may contain more than one stem, more than one loop and more than one linker as described in Example 3, Example 4a and Example 4b. It will be appreciated by one skilled in the art that removing the 5' terminal non-coding region as described above can be done using the method described in Examples 6a and 6b. It will be appreciated by one skilled in the art that other restriction sites can be designed into the 5' terminal coding region, and that different restriction enzymes can be used for this purpose.

Example 2b

Prepare and translate a library with a single reaction site adapter at the 3' end of G. To prepare a library with a single reaction site adapter at the 3' end of the coding strand of G, the library may be prepared exactly as per Example 1, except in the step, "removal of the terminal non-coding regions," the only restriction endonuclease added should be EcoRI. Doing so will remove the 3' terminal non-coding region, so that the 3' charged reaction site adapters can appropriately hybridize and ligate to the template strand. Using only the restriction endonuclease specific for a recognition site in the 3' terminal non-coding region and omitting the restriction endonuclease specific for a recognition site in the 5' terminal non-coding region will leave the 5' terminal non-coding region in place, disallowing ligation of 5' reactive site adapters to that terminus. Addition of the 3' charged reaction site adapters in the step, "ligation of charged reaction site adapters to the library," is done as in Example 1. Addition of the 5' charged reactive site adapters in that step is omitted. The reaction site adapter in this example may contain more than one stem, more than one loop and more than one linker as described in Example 3, Example 4a and Example 4b. It will be appreciated by one skilled in the art that removing the 3' terminal non-coding region as described above can be done using the method described in Example 6b. It will be appreciated by one skilled in the art that other restriction sites could be designed into the 3' terminal coding region, and that different restriction enzymes could be used for this purpose.

Example 2c

Prepare and translate a library with reaction site adapters ligated at different points during synthesis. A library with 2 reaction site adapters can be prepared in which one reaction site adapter is ligated to the template oligonucleotide G, some positional building blocks are installed on it, and a second reaction site adapter is then ligated to G. This is done by first, using either the method of Example 2a or Example 2b. Then second, installing 1 or more positional building blocks using the Example 1 steps, "Sorting a library by sequence-specific hybridization, and Eluting sorted library off of a hybridization array," and any of the chemical steps to install positional building blocks as described in Example 1, like peptide coupling or peptoid coupling, or any of the chemistry steps described in Examples 10-32. Then third, a second reaction site adapter is ligated to G. It will be appreciated by one skilled in the art that removing the second terminal non-coding region can be done immediately before ligation of a second reaction site adapter, or that chemical steps to install positional building blocks may intervene between removal of the second terminal non-coding region and ligation of a second reaction site adapter.

Example 3

Prepare and Translate a Library with 2 or More Reaction Sites Per Reaction Site Adapter A library with multiple reaction sites on a single adapter can be prepared exactly as per Example 1 or Example 4a with the exception that reaction site adapter hairpins are provided that bear 2 (or more) bases modified with reactive sites like that described in Example 1 or 4a. Several placements of the reactive site modified bases are possible, including placement of bases bearing reactive sites near either end of the stem, or both reactive sites in the loop region. Multiple reactive sites can be placed on an adapter when only one adapter is being used, or when two adapters are being used. Such reaction site adapters are synthesized or purchased from a DNA oligo synthesis company like IDT, of Coralville, IA, or Eurofins MWG of Louisville, KY.

Example 4a

Prepare and Translate a Library with Alternate Hairpins in the Reaction Site Adapter Numerous versions of the hairpins can be made and used in various contexts with the same protocols described in Example 1. In cases where a smaller hairpin is advantageous, the stem can comprise as few as 5 base pairs. Also, hairpins comprised of a 6-PEG linker between the complementary stem sequences can replace the larger DNA loop. See, Durand, M., et al. "Circular dichroism studies of an oligodeoxyribonucleotide containing a hairpin loop made of a hexaethylene glycol chain: conformation and stability." Nucleic acids research 18.21 (1990): 6353-6359). For cases where polydisplay is advantageous, the distance between multiple encoded portions on a given hairpin, and the placement of those encoded portions, can be important.

The distance between encoded portions is varied and attuned to the needs of the individual project. By installing one linker in or near the loop region of a hairpin, and a second linker in or near the anti-coding sequence, or near the anti-coding sequence in either strand of the double-stranded stem region, the distance between encoded portions is made larger or smaller by increasing or decreasing the number of bases comprising the stem. Similarly, the distance between encoded portions is made larger or smaller by placing one linker in or near the loop region, keeping the number of nucleotides in the stem constant, but varying the location of the second linker along the length of the stem. Optionally, if both linkers are placed in the stem region, the number of nucleotides separating them is varied to fit the needs of the project. Both linkers can be optionally placed in the loop region, and the number of bases between them can be varied to fit the project.

Where the placement of the encoded portion on the hairpin is important, e.g., in cases where an encoded portion placed along a stem has different access to a target molecule than an encoded portion placed in a loop, hairpins with multiple loops and stems are used. In one embodiment, a hairpin may have 2 or 3 loops and 2 stems. This hairpin may comprise an anti-coding region connected to a first strand of a first stem region which is connected to a first loop region which is connected to a first strand of a second stem region which is connected to a second loop region which is connected to a second strand of the second stem region which is connected optionally to a third loop region then to a second strand of the first stem region, or directly to a second strand of the first stem region. One or more linkers are placed in one or more of the loops, and in one or more of the stem regions as is needed for the particular project.

It will be appreciated by one skilled in the art that a great number of hairpin tertiary structures are possible which incorporate many secondary structures including, but not limited to, internal loops, bulges, and cruciform structures as described in Svoboda, P. et al. Cellular and Molecular Life Sciences CMLS, April 2006, Volume 63, Issue 7, pp 901-908, and in Bikard, et al., Microbiology And Molecular Biology Reviews, December 2010, p. 570-588, and in Kari, et al., DNA Computing Volume 3892 of the series Lecture Notes in Computer Science pp 158-170, and in Domaratzki, Theory Comput Syst (2009) 44: 432-454, Brazda, et al, BMC Molecular Biology 2011 12:33. It will be appreciated by one skilled in the art that hairpin oligo sequences incorporating such secondary and tertiary structures are synthesized by many DNA synthesis companies like Sigma-Aldrich, Integrated DNA Technologies (of Coralville, Iowa), Eurofins MWG (of Louisville, KY). It will be appreciated that a modified base bearing a reactive site for installing a linker, or bearing a linker and a reactive site can be placed at any desirable locations in the hairpin during the course of synthesis. It will be appreciated by one skilled in the art that hairpins possessing more secondary structures and/or more information will tend to be comprised of longer nucleotide sequences.

Example 4b

Prepare and Translate a Library with Alternate Hairpins in the Reaction Site Adapter Numerous versions of the hairpins are made and used in various contexts with the same protocols described in Example 1. The sequence of the stem region of the reaction site adapter can contain one or more restriction sites to allow cleavage in or near the stem region. Restriction digestion at these sites may enable release of Very tight binders to immobilized targets, and facilitate PCR amplification by removal of the loop region, which will enable proper annealing of primers. Other information may also be encoded in the reaction site adapter hairpin DNA. One example is a series of varied bases incorporated in the loop region. When amplified after selection these varied bases will help identify library members that are being enriched in selection due to amplification biases or as artefacts. Another example is a specific sequence indicating information about the selection or synthesis history of the molecule that is like an index sequence as described in Example 7. Hairpins may also comprise fluorescently-labeled bases or base analogs, radio-labeled bases or base analogs, for quantitating and analyzing various aspects of the library and its synthesis or performance. Hairpins may also contain bases or modified bases bearing functional groups that facilitate processing, like biotin. Such hairpins can be purchased from reputable vendors of custom DNA oligos like IDT of Coralville, IA, Sigma Aldrich, or Eurofins MWG of Louisville, KY.

Example 4c

Ligate a reaction site adapter to a template strand with other chemistry. A reaction site adapter is annealed to the terminal coding region of a template gene and ligated with T4 DNA Ligase as per Example 1. Other methods of covalently tethering the reaction site adapter can be used, including chemical or enzymatic methods. Charged reaction site adapters are ligated by chemical means using reagents such as water soluble carbodiimide and cyanogen bromide as done by, Shabarova, et al. (1991) Nucleic Acids Research, 19, 4247-4251), Fed-erova, et al. (1996) Nucleosides and Nucleotides, 15, 1137-1147, GryaZnov, Sergei M. et al. J. Am. Chem. Soc., vol. 115:3808-3809 (1993), and Carriero and Damlia (2003) Journal of Organic Chemistry, 68, 8328-8338. Chemical ligation is optionally done using 5M cyanogen bromide in aceto-nitrile, in a 1:10 v/v ratio with 5' phosphorylated DNA in a buffer containing 1M MES and 20 mM $MgCl_2$ at pH 7.6, the reaction being performed at 0 degrees for 5 minutes. Ligations can also be performed by topoisomerases, polymerases and ligases using manufacturer's protocols.

Example 5

Prepare and Translate a Library with Single-Stranded Terminal Coding Regions A library with less steric bulk is prepared by removing an oligonucleotide from the terminal coding region of the reaction site adapter to make the terminal coding region and optionally all or part of a stem region single-stranded. This is done exactly as per Example 1, with the following exception. Deoxy-uridine is incorporated in the provided reaction site adapters at locations in the anti-coding sequence and the stem between the terminus of the anti-coding region and the nearest linker. After sequence specific hybridization and ligation of the charged reaction site adapters to the template strand, the library is buffer exchanged into 1×UDG reaction buffer from NEB, uracil-DNA glycosylase ("UDG") is added at a concentration of 20 U/ml and incubated 30 minutes at 37° C. as per the manufacturer's protocol. Subsequent heating to 95° C. at pH 12 for 20 minutes hydrolyzed the apyrimidinic sites in the hairpin. The small ssDNA fragments produced are removed by size exclusion executed with buffer kept at 65° C.

Example 5a

Removing an oligonucleotide from the terminal coding region of the reaction site adapter is optionally performed at several points during the execution of Example 1. The oligonucleotide can optionally be removed exactly as per Example 1 with the exception that the procedure in Example 5 is performed after ligation of the charged reaction site adapter, but before addition of a first positional building block. The oligonucleotide can optionally be removed exactly as per Example 1 with the exception that the procedure in Example 5 is performed after addition of a first positional building block, but before addition of any subsequent positional building block. The oligonucleotide can optionally be removed exactly as per Example 1 with the exception that the procedure in Example 5 is performed after addition of all positional building blocks. It will be appreciated by one skilled in the art that the task of cleaving a strand of DNA at a desired location is accomplished in many ways, and that there are a large number of commercially available enzymes and published protocols facilitating this task; for example, New England Biolabs sells at least 10 nicking endonucleases and publishes protocols for their use. The specific examples given here are exemplary, and do not exclude other methods of accomplishing the task of making a terminal coding region and optionally part of the hairpin single-stranded.

Example 6a

Remove a 5' Terminal Non-Coding Region Using UDG

The restriction digestion used to remove the 5' terminal non-coding region in Example 1 is eliminated and replaced by treatment with UDG and subsequent alkaline hydrolysis of the apyrimidinic site. A library is prepared exactly as per Example 1, but wherein the oligo priming the reverse transcription incorporates a dU base at or near the 3' end of the primer. After reverse transcription, and base hydrolysis of the RNA strand, UDG can remove uracil, creating an apyrimidinic site that is subsequently cleaved by heat and alkali (see example 5 for the use of UDG and reaction conditions) producing the terminal coding region that is ready for ligation of a charged reaction site adapter. It will be appreciated by one skilled in the art that there are a number of ways of cleaving a single strand or a double strand of DNA at a desired location, and that there are a large number of commercially available enzymes and published protocols facilitating this task. The specific examples given here are exemplary, and do not exclude other methods of accomplishing the task of removing a 5' terminal non-coding region.

Example 6b

Remove a 5' Terminal Non-Coding Region or a 3' Terminal Non-Coding Region Using the Restriction Enzyme NdeI The restriction digestion used to remove the 5' terminal coding region or the 3' terminal coding region, or both, is accomplished by including the recognition site for NdeI in the terminal non-coding region, and performing restriction digestion after the reverse-transcription step. NdeI has the ability to cut RNA/DNA hybrids and also to cut single-stranded DNA. Thus, NdeI is used to cut either before or after base hydrolysis of the RNA strand, or both.

Example 6c

Remove a 5' terminal non-coding region using RNA bases in the Reverse Transcription Primer. The 5' terminal non-coding region is removed using the exact protocol of Example 1, except the primer used in the step "reverse transcribe the RNA into DNA" contains an RNA base. Upon hydrolysis of the RNA strand of the reverse transcription product as per Example 1, the RNA base in the DNA primer will also hydrolyze, removing the portion of the DNA primer that is 5' of the RNA base.

Example 7

Index Molecules of Formula (I)

A coding region is set aside or added for use as an indexing region. After preparation and translation of a library as per Example 1, the library is sorted on a hybridization array by a coding region set aside for indexing. The subpools generated by such sorting are used for different purposes, are selected for different properties, for different targets, or for the same target under different conditions. The products of the different selections are optionally amplified by PCR independently, re-pooled with the other subpools, and re-translated as in Example 1.

Example 8a

Prepare the Gene Library by an Alternate Method

Example 1 describes the combinatorial re-assortment of all codons simultaneously by restriction digestion at all internal non-coding regions of provided library gene sequences followed by ligation. This process is optionally done in a step-wise fashion instead of simultaneously. The same reaction conditions found in Example 1 in the step "the DNAs are restriction digested to de-couple all codons from each other," are used except, a single restriction endonuclease is added, instead of all the endonucleases. Then using the same reaction conditions found in Example 1 in the step, "the codons are combinatorially re-assorted to produce a gene library," the restriction digestion products are re-ligated together. The ligation product is purified by agarose gel electrophoresis, amplified by PCR, and then cut by the next restriction enzyme. The process is repeated until the gene library is complete.

Example 8b

Prepare the Gene Library by an Alternate Method

Examples 1 and 8a describe the combinatorial re-assortment of all codons by restriction digestion at all internal non-coding regions followed by ligation. In some embodiments, incomplete combinatorial re-assortment of codons to produce a population with markedly lower complexity would be advantageous. Such a gene library is produced by splitting a mixture of the 96 gene sequences described in Example 1 into several aliquots. Each aliquot is then restriction digested by a different combination of 1-3 restriction enzymes, using the reaction conditions found in Example 1 in the step "the DNAs are restriction digested to de-couple all codons from each other," or in Example 8a. After heat inactivation of the restriction enzymes, the independent digestion products are re-ligated as per the protocol in Example 1 in the step, the codons are combinatorially re-assorted to produce a gene library. The products are pooled and purified by agarose gel electrophoresis, amplified by PCR, and the rest of library preparation and translation and selection is done as per Example 1.

Example 8c

Perform a gene-shuffling or crossing-over reaction on a library. After a library like the one described in Example 1 or in Example 8a or in Example 8b is translated and selected, performing a gene-shuffling will produce new offspring phenotypes not previously extant in the library, or produce offspring phenotypes that re-sample phenotypes surviving selection. The post-selection library is amplified by PCR. The PCR product is split into a number of aliquots, and each aliquot is subjected to the protocol described in Example 8, or optionally, the protocol described in Example 1 in the steps, The DNAs are restriction digested to de-couple all codons from each other, and the codons are combinatorically re-assorted to produce a gene library. The digestion/re-ligation products are pooled, purified and amplified as described in Example 1 or 8b, and subsequent rounds of library preparation, translation and selection is done as per Example 1.

Example 9

Prepare and Translate a Library with Alternative Reactive Site Functional Groups and Linkers library using a different initial reactive site from a free amine is made in several ways. One method is to cap an existing initial reactive site functional group with a bifunctional molecule bearing the desired initial reactive site functional group. Prepare a library exactly as per Example 1, except that in the step "charging the reaction site adapters," each reaction site adapter on which a different initial reaction site is desired, a peptide bond is formed to the initial reactive site functional group amine with a bifunctional compound bearing a carboxylic acid and the desired initial reactive site functional group, using the peptide coupling reaction conditions listed in that step. For example, 5-hydroxy pentanoic acid could be reacted with the free amine to form a peptide bond, and establish the hydroxyl functional group as the initial reactive site for synthesizing the library.

A second method is to incorporate a different base modified with a different reactive site that enables or facilitates installation of other desired initial reactive site functional groups. One such base is 5-Ethynyl-dU-CE Phosphoramidite ("ethynyl-dU") sold by Glen Research in Virginia. It is optionally modified with a bifunctional linker compound bearing an azide and the desired initial reactive site functional group. For example, 5-azido pentanoic acid could be reacted with the alkynyl moiety in a "click" reaction (Huisgen reaction) with conditions found in Example 25, establishing the carboxylic acid as the initial reactive site functional group. As another representative but non-inclusive example, 5-azido 1-pentanal could be reacted with the alkynyl moiety in a "click" reaction (Huisgen reaction), establishing the aldehyde as the initial reactive site functional group. As another representative example, 4-azido, 1-bromomethylbenzene could be reacted with the alkynyl moiety in a "click" reaction (Huisgen reaction), establishing the benzyl halide as the initial reactive site functional group. This base is optionally used as an alkynyl initial reactive site for library synthesis using chemistries appropriate for alkynes chosen from Examples 10-33. Desirable initial reactive sites include, but are not limited to, amines, azides, carboxylic acids, aldehydes, alkenes, acryloyl groups, benzyl halides, halides alpha to carbonyl groups, and 1,3-dienes.

A third method is to incorporate a base modified with both a linker and an initial reactive site functional group during synthesis of the reaction site adapter hairpins. For example, incorporating 5'-Dimethoxytrityl-N6-benzoyl-N8-[6-(trifluoroacetylamino)-hex-1-yl]-8-amino-2'-deoxyAdenosine-3'-[(2-cyanoethyl)-(N,N-diisopropyl)]-phosphoramidite (also called amino-modifier C6 dA, purchased from Glen Research, Sterling VA), at strategic locations during the synthesis of the hairpin would establish a free amine as the initial reactive site functional group and a 6 carbon alkyl chain as the linker, as would incorporating 5'-Dimethoxytrityl-N2-[6-(trifluoroacetylamino)-hex-1-yl]-2'-deoxyGuanosine-3'-[(2-cyanoethyl)-(N,N-diisopropyl)]-phosphoramidite (also called amino-modifier C6 dG, purchased from Glen Research, Sterling, VA). Incorporating 5'-Dimethoxytrityl-5-[3-methyl-acrylate]-2'-deoxyUridine,3'-[(2-cyanoethyl)-(N,N-diisopropyl)]-phosphoramidite (also called Carboxy dT, purchased from Glen Research, Sterling VA) at strategic locations during the synthesis of the hairpin would establish a carboxylic acid as the initial reactive site functional group and a 2 carbon chain as the linker. Incorporating 5'-Dimethoxytrityl-5-[N-((9-fluorenylmethoxycarbonyl)-aminohexyl)-3-acrylimido]-2'-deoxyUridine, 3'-[(2-cyanoethyl)-(N,N-diisopropyl)]-phosphoramidite (also called Fmoc-amino modifier C6 dT, Glen Research, Sterling, VA) at strategic locations during the synthesis of the hairpin would establish an Fmoc-protected amine as the initial reactive site functional group and a 6 carbon alkyl chain as the linker. Incorporating 5'-Dimethoxytrityl-5-(octa-1,7-diynyl)-2'-deoxyuridine, 3'-[(2-cyanoethyl)-(N,N-diisopropyl)]-phosphoramidite (also called C6 alkyne dT, Glen Research, Sterling VA) at strategic locations during the synthesis of the hairpin would establish an alkyne as the initial reactive site functional group and an 8 carbon chain as the linker. Incorporating 5'-(4,4'-Dimethoxytrityl)-5-[N-(6-(3-benzoylthiopropanoyl)-aminohexyl)-3-acrylamido]-2'deoxyuridine, 3'[(2-cyanoethyl)-(N,N-diisopropyl)]-phosphoramidite (also called S-Bz-Thiol-Modifier C6-dT, Glen Research, Sterling VA) at strategic locations during the synthesis of the hairpin would establish a thiol as the initial reactive site functional group and a 14 atom chain as the linker. Incorporating N4-TriGl-Amino 2'deoxycytidine (from IBA GmbH, Goettingen, Germany) at strategic locations during the synthesis of the hairpin would establish an amine as the initial reactive site functional group and a 3-ethylene glycol unit chain as the linker.

Suitable linkers perform two critical functions: (i) they covalently tether the hairpin to a building block, and (ii) they do not interfere with other critical functions in the synthesis or use of molecules of formula (I). Thus, in some embodiments, the linkers are alkyl chains or PEG chains because (a) they are highly flexible, allowing appropriate and free presentation of the encoded portions to target molecules during selections, and (b) because they are relatively chemically inert and typically do not undergo side reactions during synthesis of molecules of formula (I). To adequately perform most, but not all tasks, linkers need not comprise an overall length greater than about 8 PEG units. It will be appreciated by one skilled in the art that when performing selections in which the library DNA must be kept as far from the target molecule or target structure or target surface as possible, that considerably longer linkers, and/or considerably stiffer linkers, like a peptide alpha helix, would be useful and attractive. Other desirable linkers could include polyglycine, polyalanine, or polypeptides. Linkers are also used which incorporate a fluorophore, a radiolabel, or a functional moiety used to bind a molecule of formula (I) in a manner that is orthogonal to binding to the encoded portion, or that is complementary to the binding of the encoded portion. For example, it may be necessary to incorporate a biotin in the linker to immobilize the library in some circumstances. It also may be useful to incorporate a known ligand to one binding pocket of a target molecule as a means of performing selections for an encoded portion that can bind a second binding pocket of the same target molecule.

Libraries can be optionally prepared using different linkers and different chemistries on different reactive site adapters. The linker or linkers on the 5' reaction site adapter can bear one type of linker, and one type of reactive site functional group, while the 3' reaction site adapter bears a different linker and the same reactive site functional group, or a different linker and a different reactive site functional group. Any of the linkers and functional groups named herein are appropriate for use in this example provided the chemistries required for subsequent installation of positional building blocks is compatible with the functional groups on the first building block, D and second building block E, which are reacted with the reactive site functional groups on their respective hairpins.

This compatibility has two modes. In the first mode, different chemistries are used to charge the reaction site adapters, but both the first building block D and the second building block E are capable of undergoing the same chemical transformation in the next or a subsequent downstream step. In the second mode, different chemistries are used to charge the reaction site adapters, and different chemistries are required for a subsequent down stream step. This second mode requires that the functional groups on the nascent 5' encoded portion, the functional groups on the incoming positional building block for the 5' end, and the chemistry used for that coupling, is non-reactive with the functional groups present on the nascent 3' encoded portion. Likewise, this second mode requires that the functional groups on the nascent 3' encoded portion, the functional groups on the incoming positional building block for the 3' end, and the chemistry used for that coupling, is non-reactive with the functional groups present on the nascent 5' encoded portion. The steps of installing building blocks using orthogonal chemistries on the 3' and 5' reaction site adapters can be done in any order. In addition, it will be appreciated by one skilled in the art that among the diversity building blocks installed at a given step of synthesis, that not performing an installation of any building block is an important diversity element. Appropriate chemistries for these steps include but are not limited to the chemistries described in Examples 10-32 and Example 1.

Example 10

Synthesize an Encoded Portion Using Suzuki Coupling Chemistry

A DNA library bearing an aryl-iodide, either as a reactive site on a reaction site adapter, as a building block on a charged reaction site adapter or as a partially translated molecule, is dissolved in water at 1 mM. To it is added 50 equivalents of a boronic acid as a 200 mM stock solution in dimethylacetamide, 300 equivalents of sodium carbonate as a 200 mM aqueous solution, 0.8 equivalents of palladium acetate as a 10 mM stock solution in dimethylacetamide premixed with 20 equivalents of 3,3',3" phosphanetriyltris (benzenesulfonic acid) trisodium salt as a 100 mM aqueous solution. The mixture is reacted at 65° C. for 1 hour then purified by ethanol precipitation. The DNA library is dissolved in buffer to 1 mM and 120 equivalents of sodium sulfide as a 400 mM aqueous solution is added, then reacted at 65° C. for 1 hour. The product is diluted to 200 µl with dH$_2$O and purified by ion exchange chromatography. (See Gouliaev, A. H., Franch, T. P. O., Godskesen, M. A., and Jensen, K. B. (2012) Bi-functional Complexes and methods for making and using such complexes. Patent Application WO 2011/127933 A1.)

Example 11

Synthesize an Encoded Portion Using Sonogashira Coupling Chemistry

A DNA library bearing an aryl-iodide, either as a reactive site on a reaction site adapter, as a building block on a charged reaction site adapter or as a partially translated molecule, is dissolved in water at 1 mM. To it is added 100 equivalents of an alkyne as a 200 mM stock solution in dimethylacetamide, 300 equivalents of pyrrolidine as a 200 mM stock solution in dimethylacetamide, 0.4 equivalents of palladium acetate as a 10 mM stock solution in dimethylacetamide, 2 equivalents of 3,3',3 phosphanetriyltris (benzenesulfonic acid) trisodium salt as a 100 mM aqueous solution. The reaction is run for 2 hours at 65° C., then purified by ethanol precipitation or by ion exchange chromatography. (See (1) Liang, B., Dai, M., Chen, J., and Yang, Z. (2005) Cooper-free sonogashira coupling reaction with PdCl2 in water under aerobic conditions. J. Org. Chem. 70, 391-393; (2) Li, N., Lim, R. K. V., Edwardraja, S., and Lin, Q. (2011) Copper-free Sonogashira cross-coupling for functionalization of alkyne encoded proteins in aqueous medium and in bacterial cells. J. Am. Chem. Soc. 133, 15316-15319; (3) Marziale, A. N., Schlüter, J., and Eppinger, J. (2011) An efficient protocol for copper-free palladium-catalyzed Sonogashira crosscoupling in aqueous media at low temperatures. Tetrahedron Lett. 52, 6355-6358; (4) Kanan, M. W., Rozenman, M. M., Sakurai, K., Snyder, T. M., and Liu, D. R. (2004) Reaction discovery enabled by DNA-templated synthesis and in vitro selection. Nature 431, 545-549.)

Example 12

Synthesize an Encoded Portion Using Carbamylation

A DNA library bearing an amine, either as a reactive site on a reaction site adapter, as a building block on a charged reaction site adapter or as a partially translated molecule, is dissolved in water at 1 mM. To it is added 1:4 v/v triethylamine, 50 equivalents of di-2-pyridylcarbonate as a 200 mM stock solution in dimethylacetamide. The reaction is run for 2 hours at room temp, then 40 equivalents of an amine as a 200 mM stock solution in dimethylacetamide is added at room temperature for 2 hours. The product is purified by ethanol precipitation, or ion exchange chromatography. (See (1) Artuso, E., Degani, I., and Fochi, R. (2007) Preparation of mono-, di-, and trisubstituted ureas by carbonylation of aliphatic amines with 5,5-dimethyl dithiocarbonate. Synthesis 22, 3497-3506; (2) Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 13

Synthesize an Encoded Portion Using Thioureation

A DNA library bearing an amine, either as a reactive site on a reaction site adapter, as a building block on a charged reaction site adapter or as a partially translated molecule, is dissolved in water at 1 mM. To it is added 20 equivalents 2-pyridylthionocarbonate as a 200 mM stock solution in dimethylacetamide at room temperature for 30 minutes. Then 40 equivalents of an amine are added as a 200 mM stock solution in dimethylacetamide at room temperature and slowly warmed to 60 µC and reacted for 18 hours. The product is purified by ethanol precipitation, or ion exchange chromatography. (See Deprez-Poulain, R. F., Charton, J., Leroux, V. and Deprez, B. P. (2007) Convenient synthesis of 4H-1,2,4-triazole-3-thiols using di-2-pyridylthionocarbonate. Tetrahedron Lett. 48, 8157-8162.)

Example 14

Synthesize an Encoded Portion Using Reductive Mono-Alkylation of an Amine

A DNA library bearing an amine, either as a reactive site on a reaction site adapter, as a building block on a charged reaction site adapter or as a partially translated molecule, is dissolved in water at 1 mM. To it is added 40 equivalents of aldehyde as a 200 mM stock in dimethylacetamide, and reacted at room temperature for 1 hour. Then 40 equivalents of sodium borohydride are added as a 200 mM stock solution in acetonitrile and reacted at room temperature for 1 hour. The product is purified by ethanol precipitation, or ion exchange chromatography. (See Abdel-Magid, A. F., Carson, K. G., Harris, B. D., Maryanoff, C. A., and Shah, R. D. (1996) Reductive amination of aldehydes and ketones with sodium triacetoxyborohydride. J. Org. Chem. 61, 3849-3862.)

Example 15

Synthesize an Encoded Portion Using SNAr with Heteroaryl Compounds

A DNA library bearing an amine, either as a reactive site on a reaction site adapter, as a building block on a charged reaction site adapter or as a partially translated molecule, is dissolved in water at 1 mM. To it is added 60 equivalents of a heteroarylhalide as a 200 mM stock solution in dimethylacetamide and reacted at 60° C. for 12 hours. The product is purified by ethanol precipitation, or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 16

Synthesize an Encoded Portion Using Homer-Wadsworth-Emmons Chemistry

A DNA library bearing an aldehyde, either as a reactive site on a reaction site adapter, as a building block on a charged reaction site adapter or as a partially translated molecule, is dissolved in borate buffer pH 9.4 at 1 mM. To it is added 50 equivalents of ethyl 2-(diethoxyphsopholyl) acetate as a 200 mM stock in dimetylacetamide, and 50 equivalents of cesium carbonate as a 200 mM aqueous solution and reacted at room temperature for 16 hours. The product is purified by ethanol precipitation, or ion exchange chromatography. (See Manocci, L., Leimbacher, M., Wichert, M., Scheuermann, J., and Neri, D. (2011) 20 years of DNA-encoded chemical libraries. Chem. Commun. 47, 12747-12753.)

Example 17

Synthesize an Encoded Portion Using Sulfonylation

A DNA library bearing an amine, either as a reactive site on a reaction site adapter, as a building block on a charged reaction site adapter or as a partially translated molecule, is dissolved in borate buffer pH 9.4 at 1 mM. To it is added 40 equivalents of a sulfonyl chloride as a 200 mM stock solution in dimethylacetamide and reacted at room temp for 16 hours. The product is purified by ethanol precipitation, or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 18

Synthesize an Encoded Portion Using Trichloro-Nitro-Pyrimidine

A DNA library bearing an amine, either as a reactive site on a reaction site adapter, as a building block on a charged reaction site adapter or as a partially translated molecule, is dissolved in borate buffer pH 9.4 at 1 mM. To it is added 20 equivalents of trichloro-nitro-pyrimidine (TCNP) as a 200 mM stock solution in dimethylacetamide at 5° C. The reaction is warmed to room temp over an hour and purified by ethanol precipitation. The DNA library is dissolved at 1 mM in borate buffer pH 9.4 and 40 equivalents of amine are added as a 200 mM stock solution in dimethylacetamide, 100 equivalents of neat triethylamine and reacted at room temp for 2 hours. The library is purified by ethanol precipitation. The DNA library is either immediately dissolved in borate buffer for immediate reaction, or it is pooled, re-sorted on an array and then dissolved in borate buffer, whereupon it is reacted with 50 equivalents of an amine as a 200 mM stock in dimtheylacetamide and 100 equivalents of triethylamine and reacted at room temperature for 24 hours. The product is purified by ethanol precipitation, or ion exchange chromatography. (See Roughley, S. D., and Jordan, A. M. (2011) The medicinal chemist's toolbox: an analysis of reactions used in the pursuit of drug candidates. J. Med. Chem. 54, 3451-3479.)

Example 19

Synthesize an Encoded Portion Using Trichloropyrimidine

A DNA library bearing an amine, either as a reactive site on a reaction site adapter, as a building block on a charged reaction site adapter or as a partially translated molecule, is dissolved in borate buffer pH 9.4 at 1 mM. To it is added 50 equivalents of 2,4,6 trichloropyrimidine as a 200 mM stock in DMA and reacted at room temp for 3.5 hours. The DNA is precipitated in ethanol, and then re-dissolved in borate buffer pH 9.4 at 1 mM. To it is added 40 equivalents of amine as a 200 mM acetonitrile stock and reacted at 60-80° C. for 16 hrs. The product is purified by ethanol precipitation and then the DNA library is either immediately dissolved in borate buffer for immediate reaction, or it is pooled, re-sorted on an array and then dissolved in borate buffer, whereupon it is reacted with 60 equivalents of a boronic acid as a 200 mM stock in dimethylacetamide (DMA) and 200 equivalents of sodium hydroxide as a 500 mM aqueous solution, 2 equivalents of palladium acetate as a 10 mM DMA stock and 20 equivalents of tris(3-sulfophenyl)phosphine trisodium salt (TPPTS) as a 100 mM aqueous solution, and reacted at 75° C. for 3 hours. The DNA is precipitated in ethanol, then dissolved in water at 1 mM and reacted with 120 equivalents of sodium sulfide as a 400 mM stock in water at 65° C. for 1 hour. The product is purified by ethanol precipitation, or ion exchange chromatography.

Example 20

Synthesize an Encoded Portion Using Boc-Deprotection

A DNA library bearing a Boc-protected amine, as a reactive site on a reaction site adapter, as a building block on a charged reaction site adapter, or as a partially translated molecule, is dissolved in borate buffer pH 9.4 at 0.5 mM, and heated to 90° C. for 16 hours. The product is purified by ethanol precipitation, size exclusion chromatography or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 21

Synthesize an Encoded Portion Using Hydrolysis of a t-Butyl Ester

A DNA library bearing t-butyl ester, as a reactive site on a reaction site adapter, as a building block on a charged reaction site adapter, or as a partially translated molecule, is dissolved in borate buffer at 1 mM, and reacted at 80° C. for 2 hours. The product is purified by ethanol precipitation, size exclusion chromatography or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 22

Synthesize an Encoded Portion Using Alloc-Deprotection

A DNA library bearing an Alloc-protected amine, as a reactive site on a reaction site adapter, as a building block on a charged reaction site adapter or as a partially translated molecule, is dissolved in borate buffer pH 9.4 at 1 mM. To it is added 10 equiv. of palladium tetrakis triphenylphosphine as a 10 mM DMA stock, and 10 equiv. of sodium borohydride as a 200 mM acetonitrile stock and reacted at room temperature for 2 hours. The product is purified by ethanol precipitation, or ion exchange chromatography. (See Beugelmans, R., Neuville, M. B.-C., Chastanet, J., and Zhu, J. (1995) PalladiμM catalyzed reductive deprotection of Alloc: Transprotection and peptide bond formation. Tetrahedron Lett. 36, 3129.)

Example 23

Synthesize an Encoded Portion Using Hydrolysis of a Methyl/Ethyl Ester

A DNA library bearing methyl or ethyl ester, as a reactive site on a reaction site adapter, as a building block on a charged reaction site adapter, or as a partially translated molecule, is dissolved in borate buffer at 1 mM, and reacted with 100 equiv of NaOH at 60° C. for 2 hours. The product is purified by ethanol precipitation, size exclusion chromatography or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 24

Synthesize an Encoded Portion Using Reduction of a Nitro Group

A DNA library bearing a nitro group, as a reactive site on a reaction site adapter, as a building block on a charged reaction site adapter, or as a partially translated molecule, is dissolved in water at 1 mM. To it is added 10% volume equiv. of Raney nickel slurry, 10% volume equiv. of hydrazine as a 400 mM aqueous solution and reacted at room temp for 2-24 hrs with shaking. The product is purified by ethanol precipitation, or ion exchange chromatography. (See Balcom, D., and Furst, A. (1953) Reductions with hydrazine hydrate catalyzed by Raney nickel. J. Am. Chem. Soc. 76, 4334-4334.)

Example 25

Synthesize an Encoded Portion Using "Click" Chemistry

A DNA library bearing an alkyne or an azide group, as a reactive site on a reaction site adapter, as a building block on a charged reaction site adapter or as a partially translated molecule, is dissolved in 100 mM phosphate buffer at 1 mM. To it is added copper sulfate to 625 THPTA (ligand) to 3.1 mM, amino-guanidine to 12.5 mM, ascorbate to 12.5 mM, and an azide to 1 mM (if the DNA bears an alkyne) or an alkyne to 1 mM (if the DNA bears an azide). The reaction is run at room temperature for 4 hours. The product is purified by ethanol precipitation, size exclusion chromatography or ion exchange chromatography. (See Hong, V., Presolski, Stanislav I., Ma, C. and Finn, M. G. (2009), Analysis and Optimization of Copper-Catalyzed Azide—Alkyne Cycloaddition for Bioconjugation. Angewandte Chemie International Edition, 48: 9879-9883.)

Example 26

Synthesize an Encoded Portion Incorporating a Benzimidazole

A DNA library bearing an aryl vicinal diamine, as a reactive site on a reaction site adapter, as a building block on a charged reaction site adapter or as a partially translated molecule, is dissolved in borate buffer pH 9.4 at 1 mM. To it is added 60 equiv. of an aldehyde as a 200 mM DMA stock and reacted at 60° C. for 18 hours. The product is purified by ethanol precipitation, or ion exchange chromatography. (See (1) Mandal, P., Berger, S. B., Pillay, S., Moriwaki, K., Huang, C., Guo, H., Lich, J. D., Finger, J., Kasparcova, V., Votta, B., et al. (2014) RIP3 induces apoptosis independent of pronecrotic kinase activity. Mol. Cell 56, 481-495; (2) Gouliaev, A. H., Franch, T. P.-O., Godskesen, M. A., and Jensen, K. B. (2012) Bi-functional Complexes and methods for making and using such complexes. Patent Application WO 2011/127933 A1; (3) Mukhopadhyay, C., and Tapaswi, P. K. (2008) Dowex 50W: A highly efficient and recyclable green catalyst for the construction of the 2-substituted benzimidazole moiety in aqueous medium. Catal. Commun. 9, 2392-2394.)

Example 27

Synthesize an Encoded Portion Incorporating an Imidazolidinone

A DNA library bearing an alpha-amino-amide, either as a reactive site on a reaction site adapter, as a building block on a charged reaction site adapter or as a partially translated molecule, is dissolved in 1:3 methanol:borate buffer pH 9.4 at 1 mM. To it is added 60 equiv. of an aldehyde as a 200 mM DMA stock and reacted at 60° C. for 18 hours. The product is purified by ethanol precipitation, or ion exchange chromatography. (See (1) Barrow, J. C., Rittle, K. E., Ngo, P. L., Selnick, H. G., Graham, S. L., Pitzenberger, S. M., McGaughey, G. B., Colussi, D., Lai, M.-T., Huang, Q., et al. (2007) Design and synthesis of 2,3,5-substituted imidazolidin-4-one inhibitors of BACE-1. Chem. Med. Chem. 2, 995-999; (2) Wang, X.-1, Frutos, R. P., Zhang, L., Sun, X., Xu, Y., Wirth, T., Nicola, T., Nummy, L. 1, Krishnamurthy, D., Busacca, C. A., Yee, N., and Senanayake, C. H. (2011) Asymmetric synthesis of LFA-1 inhibitor BIRT2584 on metric ton scale. Org. Process Res. Dev. 15, 1185-1191; (3) Blass, B. E., Janusz, J. M., Wu, S., Ridgeway, J. M. II, Coburn, K., Lee, W., Fluxe, A. J., White, R. E., Jackson, C. M., and Fairweather, N. 4-Imidazolidinones as KV1.5 Potassium channel inhibitors. WIPO WO2009/079624 A1, 2009.)

Example 28

Synthesize an Encoded Portion Incorporating a Quinazolinone

A DNA library bearing an 2-anilino-1-benzamide, either as a reactive site on a reaction site adapter, as a building block on a charged reaction site adapter or as a partially translated molecule, is dissolved in borate buffer pH 9.4 at 1 mM. To it is added 200 equiv. NaOH as a 1M solution in water and an aldehyde as a 200 mM stock solution in DMA and reacted at 90° C. for 14 hours. The product is purified by ethanol precipitation, or ion exchange chromatography. (See Witt, A., and Bergmann, J. (2000) Synthesis and reactions of some 2-vinyl-3H-quinazolin-4-ones. Tetrahedron 56, 7245-7253.)

Example 29

Synthesize an Encoded Portion Incorporating an Isoindolinone

A DNA library bearing an amine, either as a reactive site on a reaction site adapter, as a building block on a charged reaction site adapter or as a partially translated molecule, is dissolved in borate buffer pH 9.4 at 1 mM. To it is added a 4-bromo, 2-ene methyl ester as a 200 mM stock solution in DMA and reacted for 2 hours at 60° C. The product is purified by ethanol precipitation, or ion exchange chromatography. (See Chauleta, C., Croixa, C., Alagillea, D., Normand, S., Delwailb, A., Favotb, L., Lecronb, J.-C., and Viaud-Massuarda, M. C. (2011) Design, synthesis and biological evaluation of new thalidomide analogues as TNF-α and IL-6 production inhibitors. Bioorg. Med. Chem. Lett. 21, 1019-1022.)

Example 30

Synthesize an Encoded Portion Incorporating a Thiazole

A DNA library bearing a thiourea, either as a reactive site on a reaction site adapter, as a building block on a charged reaction site adapter or as a partially translated molecule, is dissolved in borate buffer pH 9.4 at 1 mM. To this is added 50 equiv. of a bromoketone as a 200 mM stock in DMA and reacted at room temp for 24 hours. The product is purified by ethanol precipitation, or ion exchange chromatography. (See Potewar, T. M., Ingale, S. A., and Srinivasan, K. V. (2008) Catalyst-free efficient synthesis of 2-aminothiazoles in water at ambient temperature. Tetrahedron 64, 5019-5022.)

Example 31

Synthesize an Encoded Portion Incorporating an Imidazopyridine

A DNA library bearing an aryl aldehyde, either as a reactive site on a reaction site adapter, as a building block on a charged reaction site adapter or as a partially translated molecule, is dissolved in borate buffer pH 9.4 at 1 mM. To it is added 50 equivalents of a 2-amino pyridine as a 200 mM stock solution in DMA, and 2500 equiv. of NaCN as a 1M aqueous solution and reacted at 90° C. for 10 hours. The product is purified by ethanol precipitation, or ion exchange chromatography. (See (1) Alexander Lee Satz, Jianping Cai, Yi Chen, Robert Goodnow, Felix Gruber, Agnieszka Kowalczyk, Ann Petersen, Goli Naderi-Oboodi, Lucja Orzechowski, and Quentin Strebel. DNA Compatible Multistep Synthesis and Applications to DNA Encoded Libraries Bioconjugate Chemistry 2015 26 (8), 1623-1632; (2) Beatch, G. N., Liu, Y., and Plouvier, B. M. C. PCT Int. Appl. 2001096335, Dec. 20, 2001; (3) Inglis, S. R., Jones, R. K., Booker, G. W., and Pyke, S. M. (2006) Synthesis of N-benzylated-2-aminoquinolines as ligands for the Tee SH3 domain. Bioorg. Med. Chem. Lett. 16, 387-390.)

Example 32

Synthesize an Encoded Portion Using Various Other Chemistries

Thirty-one types of compatible chemical reactions are listed with references in Handbook for DNA-Encoded Chemistry (Goodnow R. A., Jr., Ed.) pp 319-347, 2014 Wiley, N.Y. These include SNAr reactions of trichlorotriazines, diol oxidations to glyoxal compounds, Msec deprotection, Ns deprotection, Nvoc deprotection, pentenoyl deprotection, indole-styrene coupling, Diels-Alder reaction, Wittig reaction, Michael addition, Heck reaction, Henry reaction, nitrone 1,3-dipolar cycloaddition with activated alkenes, formation of oxazolidines, trifluoroacetamide deprotection, alkene-alkyne oxidative coupling, ring-closing metatheses and aldol reactions. Other reactions are published in this reference that have the potential of working in the presence of DNA and are appropriate for use.

Example 33

Use different restriction enzymes in library preparation. It will be understood that the restriction enzymes named in other Examples are representative, and that other restriction enzymes may serve the same purpose with equanimity or advantage.

Example 34

An alternative method of preparing a gene library. A library is prepared with coding regions of from about 4 to about 40 nucleotides. The library is prepared and translated as per Example 1 with the following exceptions. The library is constructed by purchasing two sets of oligos, a coding strand set of oligos and an anti-coding strand set of oligos. Each set comprises as many subsets as there are coding regions, and as many different sequences are in each subset as there are different coding sequences at a coding region. Each oligo in each subset of the coding strand oligos comprises a coding sequence and optionally a 5' non-coding region. Each oligo in each subset of the anti-coding strand oligos comprises an anti-coding sequence and optionally a 5' non-coding region complement. In order to facilitate ligations downstream in the process, all the oligos except those for the 5' termini of the coding and anti-coding strands are purchased with 5' phosphorylations, or are phosphorylated with T4 PNK from NEB as per the manufacturer's protocol. The subset of oligos possessing the coding strand 5' terminal coding sequences is combined in T4 DNA Liagse buffer from NEB with the subset possessing the 3' terminal anti-coding sequences, and the two sets are allowed to hybridize. Doing so produces a product comprising a single-stranded 5' overhang non-coding region on the coding strand, a double-stranded coding region, and an optional single stranded 5' overhang non-coding region on the anti-coding strand. This hybridization procedure is carried out separately for each coding/anti-coding pair of oligo subsets. For example, the subset of sequences encoding the second coding region from the 5' end is hybridized with its complementary anti-coding subset, the subset encoding the third coding region from the 5' end with its complementary subset, and so forth. The hybridized subset pairs are pooled and optionally purified by agarose gel electrophoresis. If the genes in the library possess non-coding regions of 1 base or more in length, and if the non-coding regions between coding regions are unique, then equimolar amounts of each hybridized subset pair are added to a single vessel. The single-stranded non-coding regions hybridize, and are ligated to each other by T4 DNA Ligase from NEB using the manufacturer's protocol. If the non-coding regions are 1 base in length or more, but are not unique, then two adjacent hybridized subsets are added to one vessel, the single-stranded non-coding regions anneal, and are ligated with T4 DNA Ligase. Upon reaction completion, the product is optionally purified by agarose gel electrophoresis, and a third hybridized subset that is adjacent to one of the ends of ligated product is added, annealed and ligated. This process is repeated until construction of the library is complete. It will be appreciated that libraries comprised of arbitrary numbers of coding regions are constructed by this method. For current purposes, libraries of more than 20 coding regions may be impractical for reasons unrelated to library construction. It will be appreciated that blunt ligations are commonly performed by those skilled in the art, and that coding regions do ligate without intervening non-coding regions, but that for hybridized subsets possessing no non-coding regions at either end, that the ligation provides both sense and anti-sense products. Products possessing the correct sense are purified away from products possessing anti-sense by preparing the library and sorting it on all hybridization arrays sequentially. The portion of the library that is captured on the array at each hybridization step possesses the correct sense. It will be appreciated that a non-coding region comprised only of a unique restriction site sequence is an attractive option of this method.

Example 34

Constructing a gene library with corresponding terminal coding regions. A library is constructed in which the 5' terminal coding region and the 3' terminal coding region encode the same building block or the same pair of different building blocks. This is accomplished if each member of the gene library possessing a given 5' terminal coding sequence only possesses one 3' terminal coding sequence. Such a library is constructed using the method of Example 33 except that the hybridized subset pairs for the 5' terminal coding region are not pooled, and the 3' terminal coding regions are not pooled. All internal coding regions are pooled and ligated as per example 33. The product of ligating all the internal coding regions is split into aliquots and one aliquot is added to each 5' terminal hybridized subset sequence and ligated. The ligation products in each well possess a single 5' terminal coding sequence but a combinatorial mixture of all sequences at all internal coding regions. These ligation products with a single 5' terminal coding sequence are transferred independently into wells containing a single 3' terminal hybridized subset sequence and ligated. The product in each well is a gene comprising a single 5' terminal coding sequence, a single 3' terminal coding sequence, and a combinatorial mixture of all sequences at all internal coding regions. It will be appreciated that there are other ways of producing the same resultant library.

Example 35

Performing selections for binding a target molecule using alternative means. Selections to identify library members capable of binding a target molecule are performed as per Example 1 with the exception that target molecules are immobilized on the surface of plastic plates like IMMU-LON® plates, MAXISORP® plates or other plates commonly used for immobilizing biological macromolecules for ELISA, or the target molecules are biotinylated and immobilized on streptavidin-coated surfaces or neutravidin-coated surfaces, or avidin-coated surfaces, including magnetic beads, beads made of synthetic polymers, beads made of polysaccharides or modified polysaccharides, plate wells, tubes, and resins. It will be understood that selections to identify library members possessing a desired trait will be performed in buffers that are compatible with DNA, compatible with keeping any target molecules in a native conformation, compatible with any enzymes used in the selection or amplification process, and compatible with identification of trait-positive library members. Such buffers include, but are not limited to, buffers made with phosphate, citrate, and TRIS. Such buffers may also include, but not be limited to, salts of potassium, sodium, ammonium, calcium, magnesium and other cations, and chloride, iodide, acetate, phosphate, citrate, and other anions. Such buffers may include, but not be limited to, surfactants like TWEEN®, TRITON™, and Chaps (3-[(3-Cholamidopropyl)dimethylammonio]-1-propanesulfonate).

Example 36

Selection for binders with long off-rates. Selections are performed to identify individuals in the library population possessing the ability to bind a target molecule as described in Example 1. Individuals that bind the target molecule with long off-rates are selected for as follows. Target molecules are immobilized by being biotinylated and incubated with a streptavidin-coated surface, or optionally immobilized without biotinylation on plastic surface like a MAXISORP® plate or some other plate suitable for binding proteins for ELISA-like assays, or by a method described in Example 35, or by another method. The library population is incubated with the immobilized target for 0.1 to 8 hours in an appropriate buffer. The duration of the incubation will depend on the estimated number of copies of each individual library member in the sample and on the number of target molecules immobilized. With higher copy numbers of individuals and higher loads of target molecule, the duration may diminish. With smaller copy numbers and/or smaller loads of a target molecule, the duration may extend. An objective is to ensure each individual in the population has the opportunity to fully interact with the target. After this incubation of the library with an immobilized target, binders in the library are presumed to be bound to the target. At this point, an excess of non-immobilized target is added to the system and the incubation is continued for about 1 to about 24 hours. Any individuals bound to an immobilized target that possesses a short off-rate, may release from the immobilized target and upon re-binding will partition into being bound by free target and immobile target. Individuals binding with long off-rates will remain bound to the immobilized target. Washing the immobilization surface preferentially removes non-binders and binders with fast off-rates, thus selecting for individuals with long off-rates. Amplification of the DNA encoding the long off-rate binders is done as per Example 1.

Example 37

Selections with mobile targets. Selections are performed in which target molecules are biotinylated, and then incubated with a library for an appropriate duration. The mixture is then immobilized for example on a streptavidin surface, whereupon the target becomes immobilized, and any library members bound to the target become immobilized as well. Washing the surface removes non-binders. Amplification of the DNA encoding the binders is done as per Example 1.

Example 38

Selections for target specificity. Selections are performed to identify individuals in the library population that bind to a desired target molecule to the exclusion of other anti-target molecules. The anti-target molecule (or molecules if there are more than one) are biotinylated and immobilized on a streptavidin-coated surface, or optionally immobilized on a plastic surface like a MAXISORP® plate or some other plate suitable for binding proteins for ELISA-like assays. In a separate container, target molecules are immobilized by being biotinylated and incubated with a streptavidin-coated surface, or optionally immobilized on plastic surface like a MAXISORP® plate or some other plate suitable binding proteins for ELISA-like assays. The library is first incubated with the anti-target. This depletes the population of individuals that bind the anti-target molecule(s). After this incubation with anti-target, the library is transferred to a container with desired target and incubated for an appropriate duration. Washing removes non-binders. Amplification of the DNA encoding the long off-rate binders is done as per Example 1. Target binders identified will have an improved probability of selectively binding the target over the anti-target(s). Optionally, the selection for affinity for a target is performed by immobilizing the target, adding free, mobile anti-target in excess, and then adding library and incubating for an appropriate duration. Under this regime, individuals with affinity for the anti-target are preferentially bound by the anti-target because it is present in excess, and can thus be removed during washing of the surface. Amplification of the DNA encoding the binders is done as per Example 1.

Example 39

Selections based on differential mobility. Selections are performed based on the ability of an individual in the library population to interact with a target molecule or polymacromolecular structure based on a difference in mobility of the library member when in a complex formed when a target molecule or polymacromolecular structure is interacting with the library member. Allowing target molecules or structures and library members to interact, and then passing the mixture through a size exclusion medium causes library members that are not interacting with a target molecule or structure to become physically separated from library members that are interacting, because the complex of the interacting library member and target molecule or structure will be larger than non-interacting library members, and therefore move through the medium with a different mobility. It will be appreciated that the difference in mobility can be a function of diffusion in the absence of a size exclusion medium, that the mobility can be induced by various means including but not limited to gravity flow, electrophoresis, and diffusion.

Example 40

General strategies for other selections. It will be appreciated by one skilled in the art that selections are performed for virtually any property provided an assay is designed that either (a) physically separates individuals in the library population that possess the desired property from individuals that do not possess it, or (b) allows DNA encoding individuals in the library population that possess the desired property to be preferentially amplified over DNA encoding library members that do not possess the property. Many methods of immobilization of target molecules are known in the art including tagging target molecules with His-tags and immobilizing on nickel surfaces, tagging target molecules with flag tags and immobilizing with anti-flag antibodies, or tagging target molecules with a linker and covalently immobilizing it to a surface. It will be appreciated that the order of the events that allow library members to bind targets and that allows targets to be immobilized is done in various orders as is dictated or enabled by the method of immobilization used. It will be appreciated that selections are performed wherein immobilization or physical separation of trait-positive individuals from trait-negative individuals is not required. For example, trait-positive individuals recruit factors enabling amplification of their DNA, where trait-negative members do not. Trait-positive individuals become tagged with a PCR primer, whereas trait-negative individuals do not. Any process differentially amplifying trait-positive individuals is suitable for use.

Example 41a

Chemistries for charging reaction site adapters. It is understood that any of the chemistries described in Examples 10-32 are appropriate for use in charging a reaction site adapter. Reaction site adapters are charged with a building block in aqueous solution, in aqueous/organic mixtures, or when immobilized on a solid support. The chemistry used to charge a reaction site adapter with a building block is not limited to reactions performed while the reaction site adapter is immobilized on a solid support like DEAE or Super Q650M; nor is it limited to reactions carried out in solution phase.

Example 41b

The absence of a building block is an encodable diversity element. In the course of library synthesis, diversity is generated when a multiplicity of building blocks are installed independently on various library subpools possessing different sequences. The absence of a building block is an optional diversity element. The absence of a building block is encoded exactly as per Example 1, except that at a desired chemical step, one or more sequence-specific subpools of the library are not treated with any chemistry to install a building block. In such case the sequence of those subpools thereby encode the absence of a building block.

Example 42

Hybridization Arrays comprised of other materials. Hybridization Arrays can accomplish 2 critical tasks: (a) they can sort a heterogeneous mixture of at least partially single-stranded DNAs through sequence specific hybridization, and (b) the arrays can enable or allow the sorted sub-pools to be removed from the array independently. The features of the array wherein anti-coding oligonucleotides are immobilized may be arranged in any three dimensional orientation that meets the above criteria, but a 2 dimensional rectangular grid array is currently most attractive because an abundance of commercially available labware is already mass produced in that format (e.g. 96-well plates, 384-well plates).

The solid supports in the features of the array upon which anti-coding oligos are immobilized can accomplish 4 tasks: (a) it can permanently affix the anti-coding oligo, (b) it can enable or allow capture of a library DNA through sequence specific hybridization to the immobilized oligo, (c) it can have low background or non-specific binding of library DNA, and (d) it can be chemically stable to the processing conditions, including a step performed at high pH. CM SEPHAROSE® has been functionalized with azido-PEG-amine (with 9 PEG units) by peptide bond formation between the amine of azido-PEG-amine and carboxyl groups on the surface of the CM SEPHAROSE® resin. Anti-coding oligos bearing an alkynyl-modifier are 'clicked' to the azide in a copper-mediated 1,3-dipolar cycloaddition (Huisgen).

Other suitable solid supports include hydrophilic beads, or polystyrene beads with hydrophilic surface coatings, polymethylmethacrylate beads with hydrophilic surface coatings, and other beads with hydrophilic surfaces which also bear a reactive functional group like a carboxylate, amine, or epoxide, to which an appropriately functionalized anti-coding oligo is immobilized. Other suitable supports include monoliths and hydrogels. See, for example, J Chromatogr A. 2002 Jun. 14; 959(1-2):121-9, J Chromatogr A. 2011 Apr. 29; 1218 (17): 2362-7, J Chromatogr A. 2011 Dec. 9; 1218(49):8897-902, Trends in Microbiology, Volume 16, Issue 11, 543-551, J. Polym. Sci. A Polym. Chem., 35: 1013-1021, J. Mol. Recognit. 2006; 19: 305-312, J. Sep. Sci. 2004, 27, 828-836. Generally, solid supports with greater surface area capture a greater amount of library DNA, and beads with smaller diameter engender far higher back pressures and resistance to flow. These constraints are in part improved by the use of porous supports or hydrogels which have very high surface areas. but lower backpressures. Generally, beads with positive charges engender greater degrees of non-specific binding of DNA.

The chassis of the hybridization array can accomplish 3 tasks: (a) it must maintain the physical separation between features, (b) enable or allow a library to flow over or through the features, and (c) enable or allow removal of the sorted library DNA from different features independently. The chassis is comprised of any material that is sufficiently rigid, chemically stable under processing conditions, and compatible with any means that are required for immobilizing supports within features. Typical materials for the chassis include plastics like DELRIN®, TECAFROM®, or polyether ether ketone (PEEK), ceramics, and metals, like aluminum or stainless steel.

Example 43

Gene library parameters. Gene libraries can comprise from 2 to 20 coding regions. The number of usable coding sequences at each internal coding region is limited only by the number of features bearing immobilized anti-coding sequences available. Because there is so much industry standard consumable labware in 24-well, 96-well, and 384-well formats, it is convenient to use these numbers of coding sequences at a coding region, but coding regions possessing for example, 768 or 1536 coding sequences would also be practical. Terminal coding sequences are not sorted on an array, so the number of sequences used at terminal coding regions has less need of complying with the numbers of wells in industry standard plates and labware. In principle, using 96 or 960 or more different coding sequences at terminal coding regions would be practical.

What is claimed is:

1. A probe molecule, wherein the probe molecule is according to formula (I), $$([(B_1)_M\text{-}D\text{-}L_1]_Y\text{—}H_1)_O\text{-}G\text{-}(H_2\text{-}[L_2\text{-}E\text{-}(B_2)_K]_W)_P, \qquad (I)$$

wherein

G is an oligonucleotide, the oligonucleotide comprising at least two coding regions encoding positional building blocks and a first terminal coding region encoding a first building block and a second terminal coding region encoding a second building block, wherein the at least two coding regions are single stranded and the first and second terminal coding regions are single or double stranded;

$H_1$ is a hairpin structure comprising oligonucleotides comprising a loop portion, a stem portion, and a 5' single stranded portion, wherein $H_1$ comprises a 5' end that is complementary to an end of the oligonucleotide G;

$H_2$ is a hairpin structure comprising oligonucleotides comprising a loop portion, a stem portion, and a 3' single stranded portion, wherein $H_2$ comprises a 3' end that is complementary to an end of the oligonucleotide G;

D is the first building block;

E is the second building block, wherein D and E are the same or different;

$B_1$ is a positional building block and M represents an integer from 1 to 20;

$B_2$ is a positional building block and K represents an integer from 1 to 20, wherein $B_1$ and $B_2$ are the same or different, wherein M and K are the same or different;

$L_1$ is a linker that covalently bonds D to the loop portion or the stem portion of $H_1$;

$L_2$ is a linker that covalently bonds E to the loop portion or the stem portion of $H_2$;

O is 1;

P is 1;

Y is an integer from 1 to 5;

W is an integer from 1 to 5; and wherein at least one of each positional building block $B_1$ at position M and $B_2$ at position K is identified by one of the coding regions, and wherein at least one of the first building block D and second building block E is identified by at least one of the first and second terminal coding regions.

2. The probe molecule of claim 1, wherein G comprises a sequence represented by the formula $(C_N\text{—}(Z_N\text{—}C_{N+1})_A)$, wherein C is a coding region, Z is a non-coding region, N is an integer from 1 to 20, and A is an integer from 1 to 20; wherein each non-coding region contains from 4 to 50 nucleotides and is optionally double stranded.

3. The probe molecule of claim 1, wherein at least one of Y and W is an integer from 1 to 2.

4. The probe molecule of claim 1, wherein each coding region contains from 6 to 50 nucleotides.

5. The probe molecule of claim 1, wherein at least one of $H_1$ and $H_2$ comprises from 20 to 90 nucleotides.

6. The probe molecule of claim 1, wherein each coding region contains from 12 to 40 nucleotides.

7. The probe molecule of claim 1, wherein Y is an integer from 1 to 2, and each coding region contains from 12 to 40 nucleotides.

8. The probe molecule of claim 1, wherein W is an integer from 1 to 2, and each coding region contains from 12 to 40 nucleotides.

9. The probe molecule of claim 1, wherein a plurality of positional building blocks at $B_1$ and $B_2$ are different.

10. A method of identifying probe molecules capable of binding or selecting for a target molecule comprising:

exposing the target molecule to a pool of probe molecules, wherein the probe molecules are according to claim 1, removing at least one probe molecule that does not bind the target molecule, amplifying at least one oligonucleotide G from the at least one probe molecule that was not removed from the target molecule to form a copy sequence, sequencing at least one oligonucleotide G of the copy sequence to identify the at least two coding regions of the probe molecule to further identify at least one of each positional building block $B_1$ at position M and $B_2$ at position K, and to identify the at least one terminal coding region of the copy molecule to further identify at least one of the first building block D and the second building block E of the probe molecule.

11. A method of forming a probe molecule, wherein the probe molecule is according to formula (I), the method comprising:

providing at least one hybridization array, the at least one hybridization array comprising at least one single stranded anti-codon oligomer immobilized on the at least one hybridization array, wherein the at least one single stranded anti-codon oligomer immobilized on the at least one hybridization array is capable of hybridizing to a coding region of a molecule of formula (II):

$$([(B_1)_{(M-1)}\text{-}D\text{-}L_1]_Y\text{—}H_1)_O\text{-}G\text{-}(H_2\text{-}[L_2\text{-}E\text{-}(B_2)_{(K-1)}]_W)_P \qquad (II)$$

wherein

G is an oligonucleotide, the oligonucleotide comprising at least two coding regions encoding positional building blocks and a first terminal coding region encoding a first building block and a second terminal coding region encoding a second building block, wherein the at least two coding regions are single stranded and the first and second terminal coding regions are single or double stranded;

$H_1$ is a hairpin structure comprising oligonucleotides comprising a loop portion, a stem portion, and a 5' single stranded portion, wherein $H_1$ comprises a 5' end that is complementary to an end of the oligonucleotide G;

$H_2$ is a hairpin structure comprising oligonucleotides comprising a loop portion, a stem portion, and a 3' single stranded portion, wherein $H_2$ comprises a 3' end that is complementary to an end of the oligonucleotide G;

D is the first building block;

E is the second building block, wherein D and E are the same or different;

$B_1$ is a positional building block and M represents an integer from 1 to 20;

$B_2$ is a positional building block and K represents an integer from 1 to 20, wherein $B_1$ and $B_2$ are the same or different, wherein M and K are the same or different;

$L_1$ is a linker that covalently bonds D to the loop portion or the stem portion of $H_1$;

$L_2$ is a linker that covalently bonds E to the loop portion or the stem portion of $H_2$;

O is 1;

P is 1;

Y is an integer from 1 to 5;

W is an integer from 1 to 5; and wherein at least one of each positional building block $B_1$ at position M and $B_2$ at position K is identified by one of the coding regions and wherein at least one of the first building block D and second building block E is identified by at least one of the first and second terminal coding regions;

sorting a pool of molecules of formula (II) into sub-pools by hybridizing a coding region of a sub-pool of molecules of formula (II) to the at least one single stranded anti-codon oligomer immobilized on the at least one hybridization array;

a step of optionally releasing the sub-pool of molecules of formula (II) from the at least one hybridization array into separate containers;

providing at least one of positional building blocks $B_1$ and $B_2$; and reacting the at least one of positional building blocks $B_1$ and $B_2$ with the molecule of formula (II) to form a sub-pool of probe molecules of formula (I):

$$([(B_1)_M\text{-}D\text{-}L_1]_Y\text{—}H_1)_O\text{-}G\text{-}(H_2\text{-}[L_2\text{-}E\text{-}(B_2)_K]_W)_P, \quad (I)$$

wherein

G is an oligonucleotide, the oligonucleotide comprising at least two coding regions encoding positional building blocks and a first terminal coding region encoding a first building block and a second terminal coding region encoding a second building block, wherein the at least two coding regions are single stranded and the first and second terminal coding regions are single or double stranded;

$H_1$ is a hairpin structure comprising oligonucleotides comprising a loop portion, a stem portion, and a 5' single stranded portion, wherein $H_1$ comprises a 5' end that is complementary to an end of the oligonucleotide G;

$H_2$ is a hairpin structure comprising oligonucleotides comprising a loop portion, a stem portion, and a 3' single stranded portion, wherein $H_2$ comprises a 3' end that is complementary to an end of the oligonucleotide G;

D is the first building block;

E is the second building block, wherein D and E are the same or different;

$B_1$ is a positional building block and M represents an integer from 1 to 20;

$B_2$ is a positional building block and K represents an integer from 1 to 20, wherein $B_1$ and $B_2$ are the same or different, wherein M and K are the same or different;

$L_1$ is a linker that covalently bonds D to the loop portion or the stem portion of $H_1$;

$L_2$ is a linker that covalently bonds E to the loop portion or the stem portion of $H_2$;

O is 1;

P is 1;

Y is an integer from 1 to 5;

W is an integer from 1 to 5; and wherein at least one of each positional building block $B_1$ at position M and $B_2$ at position K is identified by one of the coding regions, and wherein at least one of the first building block D and second building block E is identified by at least one of the first and second terminal coding regions.

12. The method of claim 11, wherein the molecule of formula (II) is prepared by:

providing an oligonucleotide G', the oligonucleotide G' comprising at least two coding regions and at least one terminal coding region, wherein the at least two coding regions are single stranded, the at least one terminal coding region is single stranded, and the at least one terminal coding region at a 5' and/or a 3' end of the oligonucleotides G' is different;

providing at least one charged carrier anti-codon, the at least one charged carrier anti-codon having the formula of $([(B_1)_{(M-1)}\text{-}D\text{-}L_1]_Y\text{-}H_1)$ and/or $(H_2\text{-}[L_2\text{-}E\text{-}(B_2)_{(K-1)}]_W)$;

combining the oligonucleotide G' and the at least one charged carrier anti-codon;

bonding the 5' end of the oligonucleotide G' to the 3' end of $H_1$, and/or bonding the 3' end of the oligonucleotide G' to the 5' end of $H_2$ to form the pool of molecules of formula (II):

$$([(B_1)_{(M-1)}\text{-}D\text{-}L_1]_Y\text{—}H_1)_O\text{-}G\text{-}(H_2\text{-}[L_2\text{-}E\text{-}(B_2)_{(K-1)}]_W)_P \quad (II)$$

wherein G, $H_1$, $H_2$, D, E, $B_1$, $B_2$, $L_1$, $L_2$, O, P, Y, and W are as defined in claim 11, and M and K are one.

13. The method of claim 11, further comprising:

removing an oligonucleotide portion from the at least one terminal coding region of a probe molecule of formula (I) or molecule of formula (II).

14. The method of claim 11, further comprising:

ligating at least one of $H_1$ to G and $H_2$ to G.

15. The method of claim 11, wherein G comprises a sequence represented by the formula $(C_N\text{—}(Z_N\text{—}C_{N+1})_A)$, wherein C is a coding region, Z is a non-coding region, N is an integer from 1 to 20, and A is an integer from 1 to 20; wherein each non-coding region contains from 4 to 50 nucleotides and is optionally double stranded.

16. The method of claim 11, wherein at least one of Y and W is an integer from 1 to 2.

17. The method of claim 11, wherein at least one of $H_1$ and $H_2$ comprises from 20 to 90 nucleotides.

18. The method of claim 11, wherein Y is an integer from 1 to 2, and each coding region contains from 12 to 40 nucleotides; and/or W is an integer from 1 to 2, and each coding region contains from 12 to 40 nucleotides.

\* \* \* \* \*